US012514700B2

(12) United States Patent
Leichner et al.

(10) Patent No.: US 12,514,700 B2
(45) Date of Patent: Jan. 6, 2026

(54) PROSTHETIC HEART VALVES WITH EXPANSION AND LOCKING ASSEMBLIES

(71) Applicant: Edwards Lifesciences Corporation, Irvine, CA (US)

(72) Inventors: Joseph Mordechai Leichner, Netanya (IL); Tamir S. Levi, Zikhron Yaakov (IL)

(73) Assignee: Edwards Lifesciences Corporation, Irvine, CA (US)

( * ) Notice: Subject to any disclaimer, the term of this patent is extended or adjusted under 35 U.S.C. 154(b) by 548 days.

(21) Appl. No.: 18/095,456

(22) Filed: Jan. 10, 2023

(65) Prior Publication Data

US 2023/0144909 A1 May 11, 2023

Related U.S. Application Data

(63) Continuation of application No. PCT/US2021/041009, filed on Jul. 9, 2021.

(60) Provisional application No. 63/050,292, filed on Jul. 10, 2020.

(51) Int. Cl.
*A61F 2/24* (2006.01)

(52) U.S. Cl.
CPC ............ *A61F 2/2418* (2013.01); *A61F 2/243* (2013.01)

(58) Field of Classification Search
CPC ...... A61F 2/2418; A61F 2/2436; A61F 2/243; A61F 2/90; A61F 2/89; A61F 2/2439; A61F 2/82; A61F 2/2427; A61F 2/24; A61F 2/2409; A61F 2002/91591; A61F 2/86; A61F 2/95; A61F 2/9517; A61F 2002/9534; A61F 2002/825; A61F 2/9522
See application file for complete search history.

(56) References Cited

U.S. PATENT DOCUMENTS

| | | | |
|---|---|---|---|
| 3,409,013 | A | 11/1968 | Berry |
| 3,548,417 | A | 12/1970 | Ronnie et al. |
| 3,587,115 | A | 6/1971 | Donald |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 4,035,849 | A | 7/1977 | Angell et al. |

(Continued)

FOREIGN PATENT DOCUMENTS

| | | | |
|---|---|---|---|
| DE | 0144167 | C | 9/1903 |
| DE | 2246526 | A1 | 3/1973 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Seema Mathew
(74) *Attorney, Agent, or Firm* — Webb & Co.; Rosie H. Kim

(57) ABSTRACT

The present disclosure relates to implantable, mechanically expandable prosthetic devices, such as prosthetic heart valves, and to assemblies and methods for facilitating change in diameter of such prosthetic devices.

17 Claims, 22 Drawing Sheets

(56) References Cited

U.S. PATENT DOCUMENTS

| | | | |
|---|---|---|---|
| 4,056,854 | A | 11/1977 | Boretos et al. |
| 4,106,129 | A | 8/1978 | Carpentier et al. |
| 4,222,126 | A | 9/1980 | Boretos et al. |
| 4,265,694 | A | 5/1981 | Boretos et al. |
| 4,297,749 | A | 11/1981 | Davis et al. |
| RE30,912 | E | 4/1982 | Hancock |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,441,216 | A | 4/1984 | Ionescu et al. |
| 4,470,157 | A | 9/1984 | Love |
| 4,535,483 | A | 8/1985 | Klawitter et al. |
| 4,574,803 | A | 3/1986 | Storz |
| 4,592,340 | A | 6/1986 | Boyles |
| 4,605,407 | A | 8/1986 | Black et al. |
| 4,612,011 | A | 9/1986 | Kautzky |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,820,299 | A | 4/1989 | Philippe et al. |
| 4,829,990 | A | 5/1989 | Thuroff et al. |
| 4,851,001 | A | 7/1989 | Taheri |
| 4,856,516 | A | 8/1989 | Hillstead |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,080,668 | A | 1/1992 | Bolz et al. |
| 5,085,635 | A | 2/1992 | Cragg |
| 5,089,015 | A | 2/1992 | Ross |
| 5,152,771 | A | 10/1992 | Sabbaghian et al. |
| 5,163,953 | A | 11/1992 | Vince |
| 5,167,628 | A | 12/1992 | Boyles |
| 5,192,297 | A | 3/1993 | Hull |
| 5,266,073 | A | 11/1993 | Wall |
| 5,282,847 | A | 2/1994 | Trescony et al. |
| 5,295,958 | A | 3/1994 | Shturman |
| 5,332,402 | A | 7/1994 | Teitelbaum |
| 5,360,444 | A | 11/1994 | Kusuhara |
| 5,370,685 | A | 12/1994 | Stevens |
| 5,397,351 | A | 3/1995 | Pavcnik et al. |
| 5,411,055 | A | 5/1995 | Kane |
| 5,411,552 | A | 5/1995 | Andersen et al. |
| 5,443,446 | A | 8/1995 | Shturman |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,185 | A | 9/1996 | Block et al. |
| 5,558,644 | A | 9/1996 | Boyd et al. |
| 5,571,175 | A | 11/1996 | Vanney et al. |
| 5,584,803 | A | 12/1996 | Stevens et al. |
| 5,591,185 | A | 1/1997 | Kilmer et al. |
| 5,591,195 | A | 1/1997 | Taheri et al. |
| 5,607,464 | A | 3/1997 | Trescony et al. |
| 5,609,626 | A | 3/1997 | Quijano et al. |
| 5,628,792 | A | 5/1997 | Lentell |
| 5,639,274 | A | 6/1997 | Fischell et al. |
| 5,665,115 | A | 9/1997 | Cragg |
| 5,716,417 | A | 2/1998 | Girard et al. |
| 5,728,068 | A | 3/1998 | Leone et al. |
| 5,749,890 | A | 5/1998 | Shaknovich |
| 5,756,476 | A | 5/1998 | Epstein et al. |
| 5,769,812 | A | 6/1998 | Stevens et al. |
| 5,800,508 | A | 9/1998 | Goicoechea et al. |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,925,063 | A | 7/1999 | Khosravi |
| 5,957,949 | A | 9/1999 | Leonhardt et al. |
| 6,027,525 | A | 2/2000 | Suh et al. |
| 6,132,473 | A | 10/2000 | Williams et al. |
| 6,168,614 | B1 | 1/2001 | Andersen et al. |
| 6,171,335 | B1 | 1/2001 | Wheatley et al. |
| 6,174,327 | B1 | 1/2001 | Mertens et al. |
| 6,210,408 | B1 | 4/2001 | Chandrasekaran et al. |
| 6,217,585 | B1 | 4/2001 | Houser et al. |
| 6,221,091 | B1 | 4/2001 | Khosravi |
| 6,231,602 | B1 | 5/2001 | Carpentier et al. |
| 6,245,102 | B1 | 6/2001 | Jayaraman |
| 6,299,637 | B1 | 10/2001 | Shaolian et al. |
| 6,302,906 | B1 | 10/2001 | Goicoechea et al. |
| 6,338,740 | B1 | 1/2002 | Carpentier |
| 6,350,277 | B1 | 2/2002 | Kocur |
| 6,352,547 | B1 | 3/2002 | Brown et al. |
| 6,425,916 | B1 | 7/2002 | Garrison et al. |
| 6,440,764 | B1 | 8/2002 | Focht et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,660 | B2 | 10/2002 | Ogle et al. |
| 6,482,228 | B1 | 11/2002 | Norred |
| 6,488,704 | B1 | 12/2002 | Connelly et al. |
| 6,527,979 | B2 | 3/2003 | Constantz et al. |
| 6,569,196 | B1 | 5/2003 | Vesely |
| 6,582,462 | B1 | 6/2003 | Andersen et al. |
| 6,605,112 | B1 | 8/2003 | Moll et al. |
| 6,652,578 | B2 | 11/2003 | Bailey et al. |
| 6,689,123 | B2 | 2/2004 | Pinchasik |
| 6,716,244 | B2 | 4/2004 | Klaco |
| 6,730,118 | B2 | 5/2004 | Spenser et al. |
| 6,733,525 | B2 | 5/2004 | Yang et al. |
| 6,767,362 | B2 | 7/2004 | Schreck |
| 6,769,161 | B2 | 8/2004 | Brown et al. |
| 6,783,542 | B2 | 8/2004 | Eidenschink |
| 6,830,584 | B1 | 12/2004 | Seguin |
| 6,878,162 | B2 | 4/2005 | Bales et al. |
| 6,893,460 | B2 | 5/2005 | Spenser et al. |
| 6,908,481 | B2 | 6/2005 | Cribier |
| 6,936,067 | B2 | 8/2005 | Buchanan |
| 7,018,406 | B2 | 3/2006 | Seguin et al. |
| 7,018,408 | B2 | 3/2006 | Bailey et al. |
| 7,096,554 | B2 | 8/2006 | Austin et al. |
| 7,225,518 | B2 | 6/2007 | Eidenschink et al. |
| 7,276,078 | B2 | 10/2007 | Spenser et al. |
| 7,276,084 | B2 | 10/2007 | Yang et al. |
| 7,316,710 | B1 | 1/2008 | Cheng et al. |
| 7,318,278 | B2 | 1/2008 | Zhang et al. |
| 7,374,571 | B2 | 5/2008 | Pease et al. |
| 7,393,360 | B2 | 7/2008 | Spenser et al. |
| 7,462,191 | B2 | 12/2008 | Spenser et al. |
| 7,510,575 | B2 | 3/2009 | Spenser et al. |
| 7,563,280 | B2 | 7/2009 | Anderson et al. |
| 7,585,321 | B2 | 9/2009 | Cribier |
| 7,618,446 | B2 | 11/2009 | Andersen et al. |
| 7,618,447 | B2 | 11/2009 | Case et al. |
| 7,655,034 | B2 | 2/2010 | Mitchell et al. |
| 7,785,366 | B2 | 8/2010 | Maurer et al. |
| 7,959,665 | B2 | 6/2011 | Pienknagura |
| 7,959,672 | B2 | 6/2011 | Salahieh et al. |
| 7,993,394 | B2 | 8/2011 | Hariton et al. |
| 8,029,556 | B2 | 10/2011 | Rowe |
| 8,075,611 | B2 | 12/2011 | Millwee et al. |

(56) References Cited

U.S. PATENT DOCUMENTS 8,128,686 B2 3/2012 Paul et al.
8,167,932 B2 5/2012 Bourang et al.
8,291,570 B2 10/2012 Eidenschink et al.
8,348,998 B2 1/2013 Pintor et al.
8,449,606 B2 5/2013 Eliasen et al.
8,454,685 B2 6/2013 Hariton et al.
8,652,203 B2 2/2014 Quadri et al.
8,685,055 B2 4/2014 VanTassel et al.
8,747,463 B2 * 6/2014 Fogarty ................ A61F 2/2409 623/2.38
9,078,781 B2 7/2015 Ryan et al.
10,874,508 B2 * 12/2020 Cartledge ............. A61F 2/2418
11,224,509 B2 1/2022 Dasi et al.
12,201,519 B2 * 1/2025 Tayeb ..................... A61F 2/243
12,268,598 B2 * 4/2025 Cohen-Tzemach .......................... A61F 2/2439
12,268,599 B2 * 4/2025 Murad .................. A61F 2/9517
12,310,847 B2 * 5/2025 Dvorsky ................. A61F 2/243
12,390,330 B2 * 8/2025 Cohen ..................... A61F 2/243
2001/0021872 A1 9/2001 Bailey et al.
2002/0026094 A1 2/2002 Roth
2002/0032481 A1 3/2002 Gabbay
2002/0138135 A1 9/2002 Duerig et al.
2002/0143390 A1 10/2002 Ishii
2002/0173842 A1 11/2002 Buchanan
2003/0014105 A1 1/2003 Cao
2003/0040791 A1 2/2003 Oktay
2003/0050694 A1 3/2003 Yang et al.
2003/0100939 A1 5/2003 Yodfat et al.
2003/0158597 A1 8/2003 Quiachon et al.
2003/0212454 A1 11/2003 Scott et al.
2004/0024452 A1 2/2004 Kruse et al.
2004/0039436 A1 2/2004 Spenser et al.
2004/0078074 A1 4/2004 Anderson et al.
2004/0186558 A1 9/2004 Pavcnik et al.
2004/0186563 A1 9/2004 Lobbi
2004/0186565 A1 9/2004 Schreck
2004/0260389 A1 12/2004 Case et al.
2005/0010285 A1 1/2005 Lambrecht et al.
2005/0075725 A1 4/2005 Rowe
2005/0075728 A1 4/2005 Nguyen et al.
2005/0096736 A1 5/2005 Osse et al.
2005/0096738 A1 5/2005 Cali et al.
2005/0137686 A1 6/2005 Salahieh et al.
2005/0188525 A1 9/2005 Weber et al.
2005/0203614 A1 9/2005 Forster et al.
2005/0203617 A1 9/2005 Forster et al.
2005/0234546 A1 10/2005 Nugent et al.
2006/0004469 A1 1/2006 Sokel
2006/0025857 A1 2/2006 Bergheim et al.
2006/0058872 A1 3/2006 Salahieh et al.
2006/0074484 A1 4/2006 Huber
2006/0108090 A1 5/2006 Ederer et al.
2006/0149350 A1 7/2006 Patel et al.
2006/0183383 A1 8/2006 Asmus et al.
2006/0229719 A1 10/2006 Marquez et al.
2006/0259136 A1 11/2006 Nguyen et al.
2006/0259137 A1 11/2006 Artof et al.
2006/0287717 A1 12/2006 Rowe et al.
2007/0005131 A1 1/2007 Taylor
2007/0010876 A1 1/2007 Salahieh et al.
2007/0010877 A1 1/2007 Salahieh et al.
2007/0112422 A1 5/2007 Dehdashtian
2007/0162102 A1 7/2007 Ryan et al.
2007/0203503 A1 8/2007 Salahieh et al.
2007/0203575 A1 8/2007 Forster et al.
2007/0203576 A1 8/2007 Lee et al.
2007/0208550 A1 9/2007 Cao et al.
2007/0213813 A1 9/2007 Segesser et al.
2007/0233228 A1 10/2007 Eberhardt et al.
2007/0260305 A1 11/2007 Drews et al.
2007/0265700 A1 11/2007 Eliasen et al.
2008/0021546 A1 1/2008 Patz et al.
2008/0114442 A1 5/2008 Mitchell et al.
2008/0125853 A1 5/2008 Bailey et al.
2008/0154355 A1 6/2008 Benichou et al.
2008/0183271 A1 7/2008 Frawley et al.
2008/0208327 A1 8/2008 Rowe
2008/0243245 A1 10/2008 Thambar et al.
2008/0255660 A1 10/2008 Guyenot et al.
2008/0275537 A1 11/2008 Limon
2008/0294248 A1 11/2008 Yang et al.
2009/0118826 A1 5/2009 Khaghani
2009/0125118 A1 5/2009 Gong
2009/0157175 A1 6/2009 Benichou
2009/0276040 A1 11/2009 Rowe et al.
2009/0281619 A1 11/2009 Le et al.
2009/0287296 A1 11/2009 Manasse
2009/0287299 A1 11/2009 Tabor et al.
2009/0299452 A1 12/2009 Eidenschink et al.
2009/0319037 A1 12/2009 Rowe et al.
2010/0004735 A1 1/2010 Yang et al.
2010/0049313 A1 2/2010 Alon et al.
2010/0082094 A1 4/2010 Quadri et al.
2010/0100176 A1 4/2010 Elizondo et al.
2010/0168844 A1 7/2010 Toomes et al.
2010/0185277 A1 7/2010 Braido et al.
2010/0198347 A1 8/2010 Zakay et al.
2010/0204781 A1 8/2010 Alkhatib
2011/0015729 A1 1/2011 Jimenez et al.
2011/0022157 A1 1/2011 Essinger et al.
2011/0066224 A1 3/2011 White
2011/0137397 A1 6/2011 Chau et al.
2011/0218619 A1 9/2011 Benichou et al.
2011/0319991 A1 12/2011 Hariton et al.
2012/0030090 A1 2/2012 Johnston et al.
2012/0089223 A1 4/2012 Nguyen et al.
2012/0101571 A1 4/2012 Thambar et al.
2012/0123529 A1 5/2012 Levi et al.
2012/0259409 A1 10/2012 Nguyen et al.
2013/0023985 A1 1/2013 Khairkhahan et al.
2013/0046373 A1 2/2013 Cartledge et al.
2013/0150956 A1 6/2013 Yohanan et al.
2013/0166017 A1 6/2013 Cartledge et al.
2013/0190857 A1 7/2013 Mitra et al.
2013/0274873 A1 10/2013 Delaloye et al.
2013/0310926 A1 11/2013 Hariton
2013/0317598 A1 11/2013 Rowe et al.
2013/0331929 A1 12/2013 Mitra et al.
2014/0194981 A1 7/2014 Menk et al.
2014/0200661 A1 7/2014 Pintor et al.
2014/0209238 A1 7/2014 Bonyuet et al.
2014/0222136 A1 8/2014 Geist et al.
2014/0277417 A1 9/2014 Schraut et al.
2014/0277419 A1 9/2014 Garde et al.
2014/0277424 A1 9/2014 Oslund
2014/0277563 A1 * 9/2014 White ..................... A61F 2/243 623/23.7
2014/0296962 A1 * 10/2014 Cartledge ................. A61F 2/95 623/1.11
2014/0330372 A1 11/2014 Weston et al.
2014/0343670 A1 * 11/2014 Bakis .................... A61F 2/2436 623/2.11
2014/0343671 A1 11/2014 Yohanan et al.
2014/0350667 A1 11/2014 Braido et al.
2015/0073545 A1 3/2015 Braido
2015/0073546 A1 3/2015 Braido
2015/0135506 A1 * 5/2015 White ....................... A61F 2/86 29/428
2015/0157455 A1 6/2015 Hoang et al.
2016/0256271 A1 * 9/2016 Backus ................. A61F 2/2418
2016/0374802 A1 12/2016 Levi et al.
2017/0014229 A1 1/2017 Nguyen-Thien-Nhon et al.
2017/0065410 A1 * 3/2017 Straubinger .......... A61F 2/2418
2018/0028310 A1 2/2018 Gurovich et al.
2018/0110618 A1 * 4/2018 Cartledge ................. A61F 2/95
2018/0153689 A1 * 6/2018 Maimon ............... A61F 2/2418
2018/0325665 A1 11/2018 Gurovich et al.
2018/0344456 A1 * 12/2018 Barash .................. A61F 2/2418
2019/0159894 A1 5/2019 Levi et al.
2019/0192288 A1 6/2019 Levi et al.
2019/0192289 A1 6/2019 Levi et al.

(56) References Cited

U.S. PATENT DOCUMENTS

| | | | | |
|---|---|---|---|---|
| 2022/0257367 A1* | 8/2022 | Neumann | ............... | A61F 2/844 |
| 2023/0144909 A1* | 5/2023 | Leichner | ................. | A61F 2/915<br>623/2.18 |
| 2023/0338140 A1* | 10/2023 | Cartledge | ............. | A61F 2/2439 |

FOREIGN PATENT DOCUMENTS

| | | | |
|---|---|---|---|
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | B1 | 5/1988 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999030646 | A1 | 6/1999 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002022054 | A1 | 3/2002 |
| WO | 2002036048 | A1 | 5/2002 |
| WO | 2002041789 | A2 | 5/2002 |
| WO | 2002043620 | A1 | 6/2002 |
| WO | 2002047575 | A2 | 6/2002 |
| WO | 2002049540 | A2 | 6/2002 |
| WO | 2003047468 | A1 | 6/2003 |
| WO | 2005034812 | A1 | 4/2005 |
| WO | 2005055883 | A1 | 6/2005 |
| WO | 2005084595 | A1 | 9/2005 |
| WO | 2005102015 | A2 | 11/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al, "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al, "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

PROSTHETIC HEART VALVES WITH EXPANSION AND LOCKING ASSEMBLIES

CROSS REFERENCE TO RELATED APPLICATION

This application is a continuation of a PCT Application No. PCT/US2021/041009, filed Jul. 9, 2021, which claims the benefit of U.S. Provisional Patent Application No. 63/050,292, filed Jul. 10, 2020, where each of above-referenced applications is incorporated herein by reference in its entirety.

FIELD OF THE INVENTION

The present disclosure relates to implantable, mechanically expandable prosthetic devices, such as prosthetic heart valves, and to assemblies and methods for facilitating change in diameter of such prosthetic devices.

BACKGROUND OF THE INVENTION

Native heart valves, such as the aortic, pulmonary and mitral valves, function to assure adequate directional flow from and to the heart, and between the heart's chambers, to supply blood to the whole cardiovascular system. Various valvular diseases can render the valves ineffective and require replacement with artificial valves. Surgical procedures can be performed to repair or replace a heart valve. Surgeries are prone to an abundance of clinical complications, hence alternative less invasive techniques of delivering a prosthetic heart valve over a catheter and implanting it over the native malfunctioning valve, have been developed over the years.

Mechanically expandable valves are a category of prosthetic valves that rely on a mechanical actuation mechanism for expansion. The actuation mechanism usually includes a plurality of actuation/locking assemblies, releasably connected to respective actuation members of the valve delivery system, controlled via the handle for actuating the assemblies to expand the valve to a desired diameter. The assemblies may optionally lock the valve's position to prevent undesired recompression thereof, and disconnection of the delivery system's actuation member from the valve actuation/locking assemblies, to enable retrieval thereof once the valve is properly positioned at the desired site of implantation.

Despite the recent advancements in prosthetic valve technology, there remains a need for improved transcatheter heart valves and delivery systems for such valves.

SUMMARY OF THE INVENTION

The present disclosure is directed toward devices and assemblies for expanding and locking prosthetic valves, as well as related methods and devices for such assemblies. In several embodiments, the disclosed assemblies are configured for delivering replacement heart valves into a heart of a patient, wherein the replacement heart valves may be expanded and locked in a desired diameter at the implantation site.

According to one aspect of the invention, there is provided a prosthetic valve comprising a frame movable between a radially compressed and a radially expanded configuration, and at least one expansion and locking mechanism. The at least one expansion and locking mechanism comprises an outer member, an inner member, and at least one plate comprising a primary aperture, disposed around the inner member. The outer member is coupled to the frame at a first location. The inner member is coupled to the frame at a second location spaced apart from the first location, the inner member extending at least partially into the outer member. The at least one plate is configured to transition between an angled locking orientation and a non-locking orientation.

The movement of the inner member in a first direction, relative to the outer member, causes the frame to foreshorten axially and expand radially in a non-locking orientation of the at least one plate. In the absence of a force applied to the plate in the first direction, movement of the inner member in a second direction, relative to the outer member, causes the at least one plate to assume the angled locking orientation.

The at least one plate is configured to inhibit advancement of the inner member in the second direction relative to the outer member, when oriented in the angled locking orientation.

According to some embodiments, the outer member further comprises a chamber comprising a proximal chamber wall and a distal chamber wall, wherein the at least one plate is disposed within the chamber.

According to some embodiments, the outer member further comprises a lateral opening exposing at least a portion of the chamber.

According to some embodiments, the at least one plate has a disc-like circular or elliptic shape.

According to some embodiments, the at least one plate has a rectangular shape.

According to some embodiments, the at least one plate comprises a rigid material.

According to some embodiments, the at least one plate comprises a plurality of plates.

According to some embodiments, the distal chamber wall comprises at least one angled portion.

According to some embodiments, the angle formed between the angled portion and the inner member is more acute than the angle formed between the plate and the inner member in the angled locking orientation.

According to some embodiments, the diameter of the primary aperture is closely matched with the outer diameter of the inner member extending therethrough, such that axial movement of the inner member frictionally engages with the primary aperture.

According to some embodiments, the diameter of the primary aperture is no more than 5 percent larger than the diameter of the inner member at the portion extending therethrough.

According to some embodiments, at least a portion of the proximal chamber wall is substantially orthogonal to a longitudinal axis of the inner member.

According to some embodiments, the outer member comprises a primary channel, configured to accommodate at least a portion of the inner member therein.

According to some embodiments, the outer member further comprises a spring disposed within the chamber, configured to urge the at least one plate in the second direction.

According to some embodiments, the spring is a helical spring coiled around the inner member.

According to some embodiments, the spring is a helical spring disposed adjacent the inner member.

According to some embodiments, the spring is a leaf spring.

According to some embodiments, the plate is coupled to the proximal chamber wall via a plate hinge, and wherein the plate is configured to pivot about the plate hinge between the angled locking orientation and the non-locking orientation.

According to some embodiments, the distal chamber wall comprises a proximally oriented protrusion.

According to some embodiments, the at least one expansion and locking mechanism further comprises a release member, extending at least partially into the outer member. The release member is coupled to the at least one plate, and configured to transition the at least one plate to the non-locking orientation, and/or retain the at least one plate in the non-locking orientation, when the release member is pulled in the second direction relative to the outer member.

According to some embodiments, the outer member further comprises a release channel, configured to accommodate the release member therein.

According to some embodiments, the plate further comprises a release aperture, wherein a distal end portion of the release member extends through the release aperture, and wherein a distal end of the release member comprises a retention feature distal to the release aperture According to some embodiments, the distal chamber wall comprises a niche dimensioned to accommodate the retention feature.

According to some embodiments, a distal end of the release member is pivotably coupled to the at least one plate via a release member distal hinge.

According to some embodiments, the outer member further comprises a first spring and a second spring, disposed within the chamber at opposite sides of the inner member, wherein the first spring is configured to bias one side of the at least one plate in a first direction, and the second spring is configured to bias an opposite second side of the at least one plate in a second direction, thereby biasing the plate to the angled locking orientation in a free state of the first and second springs.

According to some embodiments, the first spring is a compression spring, disposed between the at least one plate and the distal chamber wall, and wherein the second spring is an extension spring disposed between the at least one plate and the distal chamber wall.

According to some embodiments, the outer member further comprises an outer member fastener extending radially outward, wherein the outer member is coupled to the frame at the first location via the outer member fastener.

According to some embodiments, the inner member further comprises an inner member fastener extending radially outward, wherein the inner member is coupled to the frame at the second location via the inner member fastener.

According to some embodiments, the frame comprises intersecting struts.

According to another aspect of the invention, there is provided a prosthetic valve comprising a frame movable between a radially compressed and a radially expanded configuration, and at least one expansion and locking mechanism. The at least one expansion and locking mechanism comprises an outer member, an inner member, at least one plate comprising a primary aperture disposed around the inner member, and at least one spring disposed between the outer member and the at least one plate. The outer member is coupled to the frame at a first location. The inner member is coupled to the frame at a second location spaced apart from the first location, the inner member extending at least partially into the outer member. The at least one plate is configured to transition between an angled locking orientation and a non-locking orientation.

The movement of the inner member in a first direction, relative to the outer member, causes the frame to foreshorten axially and expand radially in a non-locking orientation of the at least one plate. In the absence of a force applied to the plate in the first direction, the at least one spring is configured to bias the at least one plate to the angled locking orientation.

The at least one plate is configured to inhibit advancement of the inner member in the second direction relative to the outer member, when oriented in the angled locking orientation.

According to some embodiments, the at least one plate has a disc-like circular or elliptic shape.

According to some embodiments, the at least one plate has a rectangular shape.

According to some embodiments, the at least one plate comprises a rigid material.

According to some embodiments, the at least one plate comprises a plurality of plates.

According to some embodiments, the diameter of the primary aperture is no more than 5 percent larger than the diameter of the inner member at the portion extending therethrough.

According to some embodiments, the outer member comprises a primary channel, configured to accommodate at least a portion of the inner member therein.

According to some embodiments, the outer member further comprises a chamber comprising a proximal chamber wall and a distal chamber wall, wherein the at least one plate and the at least one spring are disposed within the chamber.

According to some embodiments, the distal chamber wall comprises a proximally oriented protrusion.

According to some embodiments, the distal chamber wall comprises at least one angled portion.

According to some embodiments, the angle formed between the angled portion and the inner member is more acute than the angle formed between the plate and the inner member in the angled locking orientation.

According to some embodiments, at least a portion of the proximal chamber wall is substantially orthogonal to a longitudinal axis of the inner member.

According to some embodiments, the at least one spring comprises a helical spring coiled around the inner member.

According to some embodiments, the coiled spring is a compression spring disposed between the proximal chamber wall and the at least one plate.

According to some embodiments, the at least one spring comprises at least one helical spring disposed adjacent the inner member.

According to some embodiments, the at least one helical spring is a compression spring disposed between the proximal chamber wall and the at least one plate.

According to some embodiments, the at least one helical spring is an extension spring disposed between the distal chamber wall and the at least one plate.

According to some embodiments, the at least one spring is a leaf spring.

According to some embodiments, the at least one expansion and locking mechanism further comprises a release member, extending at least partially into the outer member, the release member coupled to the at least one plate, and configured to transition the at least one plate to the non-locking orientation, and/or retain the at least one plate in the non-locking orientation, when the release member is pulled in the second direction relative to the outer member.

According to some embodiments, the outer member further comprises a release channel, configured to accommodate the release member therein.

According to some embodiments, the at least one plate further comprises a release aperture, wherein a distal end portion of the release member extends through the release aperture, and wherein a distal end of the release member comprises a retention feature distal to the release aperture.

According to some embodiments, the distal chamber wall comprises a niche dimensioned to accommodate the retention feature.

According to some embodiments, a distal end of the release member is pivotably coupled to the at least one plate via a release member distal hinge.

According to some embodiments, the at least one spring comprises a first spring and a second spring, both of which are disposed within the chamber at opposite sides of the inner member, wherein the first spring is configured to bias one side of the at least one plate in a first direction, and the second spring is configured to bias an opposite second side of the at least one plate in a second direction, thereby biasing the plate to the angled locking orientation in a free state of the first and second springs.

According to some embodiments, the first spring is a compression spring, disposed between the at least one plate and the distal chamber wall, and wherein the second spring is an extension spring disposed between the at least one plate and the distal chamber wall.

According to yet another aspect of the invention, there is provided a delivery assembly comprising a prosthetic valve and a delivery apparatus. The prosthetic valve comprises a frame movable between a radially compressed and a radially expanded configuration, and at least one expansion and locking mechanism. The at least one expansion and locking mechanism comprises an outer member, an inner member, and at least one plate comprising a primary aperture, disposed around the inner member. The outer member is coupled to the frame at a first location. The inner member is coupled to the frame at a second location spaced apart from the first location, the inner member extending at least partially into the outer member. The at least one plate is configured to transition between an angled locking orientation and a non-locking orientation.

The delivery apparatus comprises a handle, a delivery shaft extending distally from the handle, and at least one actuation assembly extending from the handle through the delivery shaft, and detachably coupled to the at least one expansion and locking assembly.

The frame is movable from the radially compressed configuration to the radially expanded configuration upon actuating the at least one expansion and locking assembly by the at least one actuation assembly. The movement of the inner member in a first direction, relative to the outer member, causes the frame to foreshorten axially and expand radially in a non-locking orientation of the at least one plate.

In the absence of a force applied to the plate in the first direction, movement of the inner member in a second direction, relative to the outer member, causes the at least one plate to assume the angled locking orientation. The at least one plate is configured to inhibit advancement of the inner member in the second direction relative to the outer member, when oriented in the angled locking orientation.

According to some embodiments, the at least one actuation assembly comprises an actuation member and an actuation support sleeve disposed around the actuation member, wherein the actuation member and the actuation support sleeve are movable longitudinally relative to each other in a telescoping manner.

According to some embodiments, the at least one actuation member is chosen from: a wire, a cable, a rod, or a tube.

According to some embodiments, the actuation support sleeve is a tube or a sheath having sufficient rigidity, such that the actuation support sleeve can apply an axial force against the outer member without bending or buckling.

According to some embodiments, the at least one actuation member is threadedly engaged with the corresponding inner member.

According to some embodiments, the handle comprises a plurality of knobs.

According to some embodiments, at least one of the plurality of knobs is configured to axially move each actuation member relative to the respective actuation support sleeve.

According to some embodiments, at least one of the plurality of knobs is configured to disengage each actuation assembly from the respective expansion and locking assembly.

According to some embodiments, the outer member further comprises a chamber comprising a proximal chamber wall and a distal chamber wall, and wherein the at least one plate is disposed within the chamber.

According to some embodiments, the at least one plate has a disc-like circular or elliptic shape.

According to some embodiments, the at least one plate has a rectangular shape.

According to some embodiments, the at least one plate comprises a rigid material.

According to some embodiments, the at least one plate comprises a plurality of plates.

According to some embodiments, the distal chamber wall comprises at least one angled portion.

According to some embodiments, the angle formed between the angled portion and the inner member is more acute than the angle formed between the plate and the inner member in the angled locking orientation.

According to some embodiments, the diameter of the primary aperture is closely matched with the outer diameter of the inner member extending therethrough, such that axial movement of the inner member frictionally engages with the primary aperture.

According to some embodiments, the diameter of the primary aperture is no more than 5 percent larger than the diameter of the inner member at the portion extending therethrough.

According to some embodiments, at least a portion of the proximal chamber wall is substantially orthogonal to a longitudinal axis of the inner member.

According to some embodiments, the outer member comprises a primary channel, configured to accommodate at least a portion of the inner member and at least a portion of the actuation member therein.

According to some embodiments, the outer member further comprises a spring disposed within the chamber, configured to urge the at least one plate in the second direction.

According to some embodiments, the spring is a helical spring coiled around the inner member.

According to some embodiments, the spring is a helical spring disposed adjacent the inner member.

According to some embodiments, the spring is a leaf spring.

According to some embodiments, the plate is coupled to the proximal chamber wall via a plate hinge, wherein the plate is configured to pivot about the plate hinge between the angled locking orientation and the non-locking orientation.

According to some embodiments, the distal chamber wall comprises a proximally oriented protrusion.

According to yet another aspect of the invention, there is provided a delivery assembly comprising a prosthetic valve and a delivery apparatus. The prosthetic valve comprises a frame movable between a radially compressed and a radially expanded configuration, and at least one expansion and locking mechanism. The at least one expansion and locking mechanism comprises an outer member, an inner member, a release member, and at least one plate comprising a primary aperture, disposed around the inner member.

The outer member is coupled to the frame at a first location. The inner member is coupled to the frame at a second location spaced apart from the first location, the inner member extending at least partially into the outer member. The release member extends at least partially into the outer member, and is coupled to the at least one plate. The at least one plate is configured to transition between an angled locking orientation and a non-locking orientation.

The delivery apparatus comprises a handle, a delivery shaft extending distally from the handle, at least one actuation assembly extending from the handle through the delivery shaft, and detachably coupled to the at least one expansion and locking assembly, and at least one release assembly extending from the handle through the delivery shaft, and detachably coupled to the at least one release member.

The frame is movable from the radially compressed configuration to the radially expanded configuration upon actuating the at least one expansion and locking assembly by the at least one actuation assembly. The movement of the inner member in a first direction, relative to the outer member, causes the frame to foreshorten axially and expand radially in a non-locking orientation of the at least one plate.

In the absence of a force applied to the plate in the first direction, movement of the inner member in a second direction, relative to the outer member, causes the at least one plate to assume the angled locking orientation. The at least one plate is configured to inhibit advancement of the inner member in the second direction relative to the outer member, when oriented in the angled locking orientation.

The release member is configured to transition the at least one plate to the non-locking orientation, and/or retain the at least one plate in the non-locking orientation, when the release member is pulled by the release assembly in the first direction relative to the outer member.

According to some embodiments, the at least one actuation assembly comprises an actuation member and an actuation support sleeve disposed around the actuation member, wherein the actuation member and the support sleeve are movable longitudinally relative to each other in a telescoping manner.

According to some embodiments, the at least one actuation member is chosen from: a wire, a cable, a rod, or a tube.

According to some embodiments, the support sleeve is a tube or a sheath having sufficient rigidity, such that the support sleeve can apply an axial force against the frame without bending or buckling.

According to some embodiments, the at least one actuation member is threadedly engaged with the corresponding inner member.

According to some embodiments, the at least one release assembly comprises a release arm and a release support sleeve disposed around the release arm, and wherein the release arm and the release support sleeve are movable longitudinally relative to each other in a telescoping manner.

According to some embodiments, the at least one release arm is chosen from: a wire, a cable, a rod, or a tube.

According to some embodiments, the release support sleeve is a tube or a sheath having sufficient rigidity, such that the release support sleeve can apply an axial force against the outer member without bending or buckling.

According to some embodiments, the at least one release arm is threadedly engaged with the corresponding release member.

According to some embodiments, the handle comprises a plurality of knobs.

According to some embodiments, at least one of the plurality of knobs is configured to axially move each actuation member relative to the respective actuation support sleeve.

According to some embodiments, at least one of the plurality of knobs is configured to axially move each release arm relative to the respective release support sleeve.

According to some embodiments, at least one of the plurality of knobs is configured to disengage each actuation assembly from the respective expansion and locking assembly.

According to some embodiments, at least one of the plurality of knobs is configured to disengage each release assembly from the respective expansion and locking assembly.

According to some embodiments, the outer member further comprises a chamber comprising a proximal chamber wall and a distal chamber wall, and wherein the at least one plate is disposed within the chamber.

According to some embodiments, the at least one plate has a disc-like circular or elliptic shape.

According to some embodiments, the at least one plate has a rectangular shape.

According to some embodiments, the at least one plate comprises a rigid material.

According to some embodiments, the at least one plate comprises a plurality of plates.

According to some embodiments, the distal chamber wall comprises at least one angled portion.

According to some embodiments, the angle formed between the angled portion and the inner member is more acute than the angle formed between the plate and the inner member in the angled locking orientation.

According to some embodiments, the diameter of the primary aperture is closely matched with the outer diameter of the inner member extending therethrough, such that axial movement of the inner member frictionally engages with the primary aperture.

According to some embodiments, the diameter of the primary aperture is no more than 5 percent larger than the diameter of the inner member at the portion extending therethrough.

According to some embodiments, at least a portion of the proximal chamber wall is substantially orthogonal to a longitudinal axis of the inner member.

According to some embodiments, the outer member comprises a primary channel, configured to accommodate at least a portion of the inner member and at least a portion of the actuation member therein.

According to some embodiments, the outer member comprises a release channel, configured to accommodate at least a portion of the release member and at least a portion of the release arm therein.

According to some embodiments, the outer member further comprises a spring disposed within the chamber, configured to urge the at least one plate in the second direction.

According to some embodiments, the spring is a helical spring coiled around the inner member.

According to some embodiments, the spring is a helical spring disposed adjacent the inner member.

According to some embodiments, the spring is a leaf spring.

According to some embodiments, the plate is coupled to the proximal chamber wall via a plate hinge, wherein the plate is configured to pivot about the plate hinge between the angled locking orientation and the non-locking orientation.

According to some embodiments, the distal chamber wall comprises a proximally oriented protrusion.

According to some embodiments, the at least one plate further comprises a release aperture, wherein a distal end portion of the release member extends through the release aperture, and wherein a distal end of the release member comprises a retention feature distal to the release aperture.

According to some embodiments, the distal chamber wall comprises a niche dimensioned to accommodate the retention feature.

According to some embodiments, a distal end of the release member is pivotably coupled to the at least one plate via a release member distal hinge.

According to some embodiments, the outer member comprises a first spring and a second spring, disposed within the chamber at opposite sides of the inner member, wherein the first spring is configured to bias one side of the at least one plate in a first direction, and the second spring is configured to bias an opposite second side of the at least one plate in a second direction, thereby biasing the plate to the angled locking orientation in a free state of the first and second springs.

According to some embodiments, the first spring is a compression spring, disposed between the at least one plate and the distal chamber wall, and wherein the second spring is an extension spring disposed between the at least one plate and the distal chamber wall.

According to yet another aspect of the invention, there is provided a method of implanting a prosthetic valve, the method comprises positioning a prosthetic valve at a target site in a patient's body using a delivery apparatus. The method further comprises radially expanding the prosthetic valve from a radially compressed configuration to a radially expanded configuration; The method further comprises locking the expansion and locking assembly.

The prosthetic valve comprises at least one expansion and locking assembly, wherein the expansion and locking assembly comprising an outer member, an inner member partially disposed within, and movable axially relative to, the outer member, and at least one plate dispose within the outer member and around the inner member. The delivery apparatus comprises at least one actuation assembly, detachably coupled to the at least one expansion and locking assembly.

Radially expanding the prosthetic valve includes applying, via the at least one actuation assembly, a pull force on the inner member, configured to axially move the inner member in a first direction relative to the outer member.

Locking the expansion and locking assembly includes releasing the pull force exerted on the inner member by the actuation assembly, thereby allowing the at least one plate to assume an angled locking orientation.

According to some embodiments, the radially expanded configuration comprises partially expanded configurations and/or a fully expanded configuration, wherein the step of radially expanding the prosthetic valve is executed again after the locking step, so as to reorient the at least one plate from the angled locking orientation to a non-locking orientation, allowing further expansion of the prosthetic valve from a partially expanded configuration to another partially expanded configuration or to a fully expanded configuration.

According to some embodiments, the at least one actuation assembly comprises an actuation member detachably coupled to the inner member, and an actuation support sleeve disposed around the actuation member, wherein the step of radially expanding the prosthetic valve comprises exerting a pull force to move the actuation member in a first direction relative to the actuation support sleeve, while keeping the actuation support sleeve stationary or moved in an opposite second direction, so as to apply a counter force against the outer member.

According to some embodiments, the method further comprising a step of detaching the at least one actuation member from the at least one inner member, and retrieving the delivery apparatus from the patient's body.

According to some embodiments, the at least one actuation member is threadedly engaged with the at least one inner member, wherein detaching the at least one actuation member comprises rotating the at least one actuation member around a longitudinal axis thereof.

According to yet another aspect of the invention, there is provided a method of implanting a prosthetic valve, the method comprises positioning a prosthetic valve at a target site in a patient's body using a delivery apparatus. The method further comprises radially expanding the prosthetic valve from a radially compressed configuration to a radially expanded configuration. The method further comprises locking the expansion and locking assembly. The method further comprises unlocking the expansion and locking assembly. The method further comprises re-compressing the prosthetic valve.

The prosthetic valve comprises at least one expansion and locking assembly, wherein the expansion and locking assembly comprising an outer member, an inner member partially disposed within, and movable axially relative to, the outer member, at least one plate dispose within the outer member and around the inner member, and a release member disposed within the outer member and axially movable relative thereto. The release member is coupled to the at least one plate The delivery apparatus comprises at least one actuation assembly detachably coupled to the at least one expansion and locking assembly, and at least one release assembly detachably coupled to the release member.

Radially expanding the prosthetic valve includes applying, via the at least one actuation assembly, a pull force on the inner member, configured to axially move the inner member in a first direction relative to the outer member.

Locking the expansion and locking assembly includes releasing the pull force exerted on the inner member by the actuation assembly, thereby allowing the at least one plate to assume an angled locking orientation.

Unlocking the expansion and locking assembly includes applying, via the at least one release assembly, a pull force on the release member, configured to transition the at least one plate from the angled locking orientation to a non-locking orientation. Re-compressing the prosthetic valve is executed such that the at least one inner member is moved in a second direction relative to the at least one outer member.

According to some embodiments, any of the steps of radially expanding the prosthetic valve, locking, unlocking, and re-compressing the prosthetic valve, are repeated for any desired number of times and in any order, so as to reach a final desired expansion diameter of the prosthetic valve.

According to some embodiments, the method further comprises a step of re-positioning the prosthetic valve using the delivery apparatus, after the step of re-compressing the prosthetic valve.

According to some embodiments, the at least one actuation assembly comprises an actuation member detachably coupled to the inner member, and an actuation support sleeve disposed around the actuation member. The at least one release assembly comprises a release arm detachably coupled to the release member, and a release support sleeve disposed around the release arm.

The step of radially expanding the prosthetic valve comprises exerting a pull force to move the actuation member in a first direction relative to the actuation support sleeve, while keeping the actuation support sleeve stationary or moved in an opposite second direction, so as to apply a counter force against the outer member The step of unlocking the prosthetic valve comprises exerting a pull force to move the release arm in a first direction relative to the release support sleeve, while keeping the release support sleeve stationary or moved in an opposite second direction, so as to apply a counter force against the outer member.

According to some embodiments, the method further comprises steps of detaching the at least one actuation member from the at least one inner member, detaching the at least one release arm from the release member, and retrieving the delivery apparatus from the patient's body.

According to some embodiments, the at least one actuation member is threadedly engaged with the at least one inner member, and the at least one release arm is threadedly engaged with the at least one release member. Detaching the at least one actuation member comprises rotating the at least one actuation member around a longitudinal axis thereof, and detaching the at least one release arm comprises rotating the at least one release arm around a longitudinal axis thereof.

According to another aspect of the invention, there is provided a method for assembling an expansion and locking mechanism, comprising the steps of: (i) providing an outer member comprising a chamber and a lateral opening exposing at least a portion of the chamber; (ii) inserting at least one plate, comprising a primary aperture, into the chamber through the lateral opening; (iii) orienting the at least one plate in a substantially orthogonal orientation, relative to a longitudinal axis of the outer member; and (iv) inserting the inner member into the outer member, through the primary aperture of the at least one plate.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will become more apparent from the following detailed description, which proceeds with reference to the accompanying figures.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures.

DETAILED DESCRIPTION OF SOME EMBODIMENTS

Figure 1:
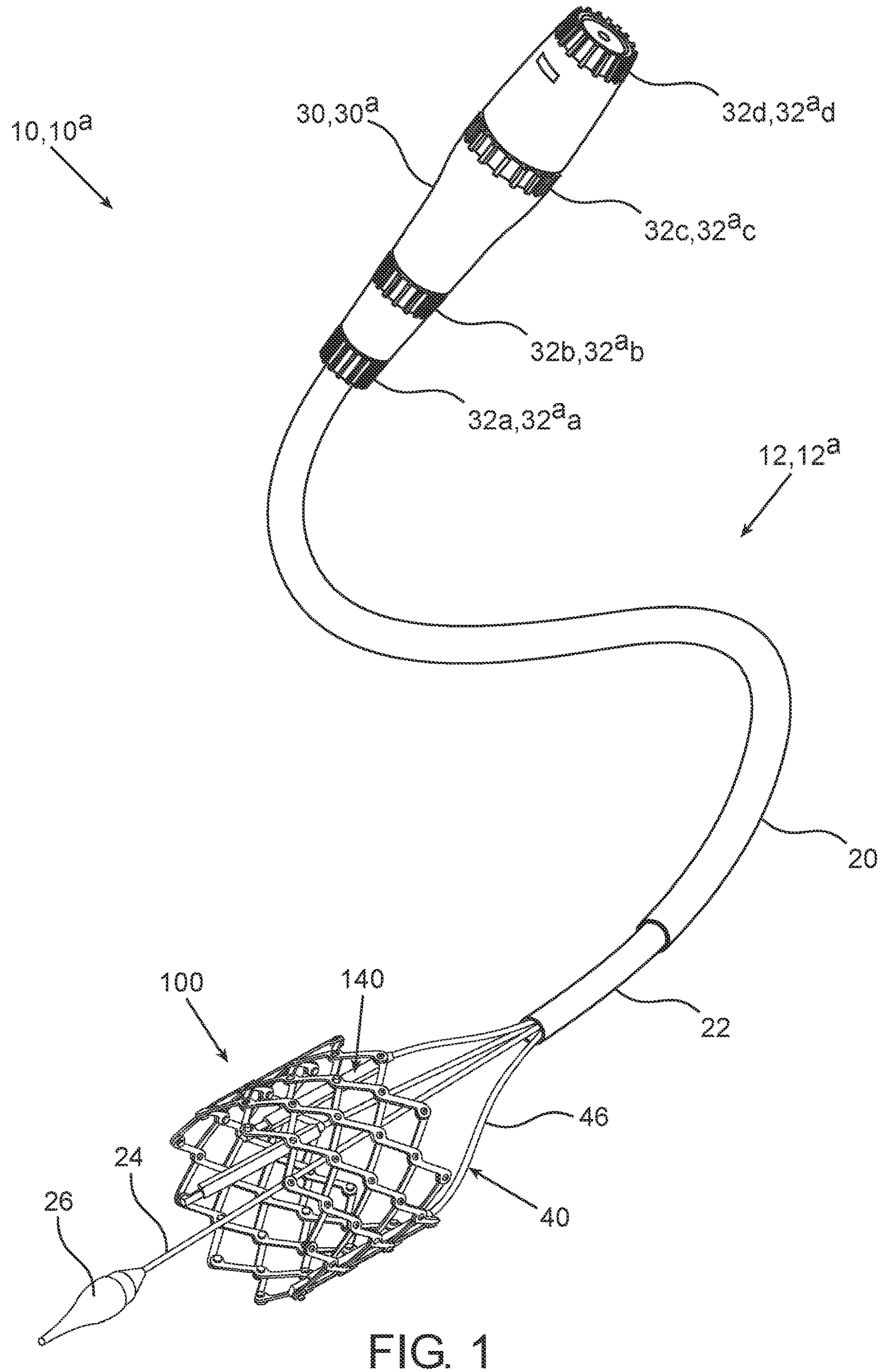
FIG. 1 shows a view in perspective of a delivery assembly comprising a delivery apparatus carrying a prosthetic valve, according to some embodiments.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present, or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the terms "have" or "includes" means "comprises." As used herein, "and/or" means "and" or "or," as well as "and" and "or".

Directions and other relative references may be used to facilitate discussion of the drawings and principles herein, but are not intended to be limiting. For example, certain terms may be used such as "inner," "outer," "upper," "lower," "inside," "outside,", "top," "bottom," "interior," "exterior," "left," right," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same.

Throughout the figures of the drawings, different superscripts for the same reference numerals are used to denote different embodiments of the same elements. Embodiments of the disclosed devices and systems may include any combination of different embodiments of the same elements. Specifically, any reference to an element without a superscript may refer to any alternative embodiment of the same element denoted with a superscript. In order to avoid undue clutter from having too many reference numbers and lead lines on a particular drawing, some components will be introduced via one or more drawings and not explicitly identified in every subsequent drawing that contains that component.

FIG. 1 shows a view in perspective of a delivery assembly 10, according to some embodiments. The delivery assembly 10 can include a prosthetic valve 100 and a delivery apparatus 12. The prosthetic valve 100 can be on or releasably coupled to the delivery apparatus 12. The delivery apparatus can include a handle 30 at a proximal end thereof, a nosecone shaft 24 extending distally from the handle 30, a nosecone 26 attached to the distal end of the nosecone shaft 24, a delivery shaft 22 extending over the nosecone shaft 24, and optionally an outer shaft 20 extending over the delivery shaft 22.

The term "proximal", as used herein, generally refers to the side or end of any device or a component of a device, which is closer to the handle 30 or an operator of the handle 30 when in use.

The term "distal", as used herein, generally refers to the side or end of any device or a component of a device, which is farther from the handle 30 or an operator of the handle 30 when in use.

The term "prosthetic valve", as used herein, refers to any type of a prosthetic valve deliverable to a patient's target site over a catheter, which is radially expandable and compressible between a radially compressed, or crimped, configuration, and a radially expanded configuration. Thus, a prosthetic valve 100 can be crimped or retained by a delivery apparatus 12 in a compressed configuration during delivery, and then expanded to the expanded configuration once the prosthetic valve 100 reaches the implantation site. The expanded configuration may include a range of diameters to which the valve may expand, between the compressed configuration and a maximal diameter reached at a fully expanded configuration. Thus, a plurality of partially expanded configurations may relate to any expansion diameter between radially compressed or crimped configuration, and maximally expanded configuration.

The term "plurality", as used herein, means more than one.

A prosthetic valve 100 of the current disclosure may include any prosthetic valve configured to be mounted within the native aortic valve, the native mitral valve, the native pulmonary valve, and the native tricuspid valve. While a delivery assembly 10 described in the current disclosure, includes a delivery apparatus 12 and a prosthetic valve 100, it should be understood that the delivery apparatus 12 according to any embodiment of the current disclosure can be used for implantation of other prosthetic devices aside from prosthetic valves, such as stents or grafts.

According to some embodiments, the prosthetic valve 100 is a mechanically expandable valve, and the delivery apparatus 12, such as the delivery apparatus 12$^a$ of a delivery assembly 10$^a$ shown in FIG. 1, further comprises a plurality of actuation assemblies 40 extending from the handle 30$^a$ through the delivery shaft 22. In the illustrated embodiment, the prosthetic valve 100 has three actuation assemblies 40, however, in other embodiments a greater or fewer number of actuation assemblies 40 can be used.

Each actuation assembly 40 can generally include an actuation member 42 (hidden from view in FIG. 1, visible in FIGS. 7A-7D) releasably coupled at its distal end 44 to respective expansion and locking assembly 140 of the valve 100, and an actuation support sleeve 46 disposed around the corresponding actuation member 42. The actuation member 42 and the actuation support sleeve 46 can be movable longitudinally relative to each other in a telescoping manner to radially expand and contract the frame 106, as further described in U.S. Publication Nos. 2018/0153689, 2018/0153689 and 2018/0325665 which are incorporated herein by reference. The actuation members 42 can be, for example, wires, cables, rods, or tubes. The actuation support sleeves 46 can be, for example, tubes or sheaths having sufficient rigidity such that they can apply a distally directed force to the frame without bending or buckling.

The prosthetic valve 100 can be delivered to the site of implantation via a delivery assembly 10 carrying the valve 100 in a radially compressed or crimped configuration, toward the target site, to be mounted against the native anatomy, by expanding the valve 100 via a mechanical expansion mechanism, as will be elaborated below.

The delivery assembly 10 can be utilized, for example, to deliver a prosthetic aortic valve for mounting against the aortic annulus, to deliver a prosthetic mitral valve for mounting against the mitral annulus, or to deliver a prosthetic valve for mounting against any other native annulus.

The nosecone 26 can be connected to the distal end of the nosecone shaft 24. A guidewire (not shown) can extend through a central lumen of the nosecone shaft 24 and an inner lumen of the nosecone 26, so that the delivery apparatus 12 can be advanced over the guidewire through the patient's vasculature.

A distal end portion of the outer shaft 20 can extend over the prosthetic valve 100 and contact the nosecone 26 in a delivery configuration of the delivery apparatus 12. Thus, the distal end portion of the outer shaft 20 can serve as a delivery capsule that contains, or houses, the prosthetic valve 100 in a radially compressed or crimped configuration for delivery through the patient's vasculature.

The outer shaft 20 and the delivery shaft 22 can be configured to be axially movable relative to each other, such that a proximally oriented movement of the outer shaft 20 relative to the delivery shaft 22, or a distally oriented movement of the delivery shaft 22 relative to the outer shaft 20, can expose the prosthetic valve 100 from the outer shaft 20. In some configurations, the prosthetic valve 100 is not housed within the outer shaft 20 during delivery. Thus, according to some optional configurations, the delivery apparatus 12 does not necessarily include an outer shaft 20.

As mentioned above, the proximal ends of the nosecone shaft 24, the delivery shaft 22, components of the actuation assemblies 40, and when present—the outer shaft 20, can be coupled to the handle 30. During delivery of the prosthetic valve 100, the handle 30 can be maneuvered by an operator (e.g., a clinician or a surgeon) to axially advance or retract components of the delivery apparatus 12, such as the nosecone shaft 24, the delivery shaft 22, and/or the outer shaft 20, through the patient's vasculature, as well as to expand or contract the prosthetic valve 100, for example by maneuvering the actuation assemblies 40, and to disconnect the prosthetic valve 100 from the delivery apparatus 12, for example—by decoupling the actuation members 42 from the expansion and locking assemblies 140 of the valve 100, in order to retract it once the prosthetic valve 100 is mounted in the implantation site.

According to some embodiments, the handle 30 can include one or more operating interfaces, such as steerable or rotatable adjustment knobs 32, levers, sliders, buttons and other actuating mechanisms, which are operatively connected to different components of the delivery apparatus 12 and configured to produce axial movement of the delivery apparatus 12 in the proximal and distal directions, as well as to expand or contract the prosthetic valve 100 via various adjustment and activation mechanisms as will be further described below.

The handle 30 may further comprises one or more visual or auditory informative elements (not shown) configured to provide visual or auditory information and/or feedback to a user or operator of the delivery apparatus 12, such as a display, LED lights, speakers and the like.

Figure 2:
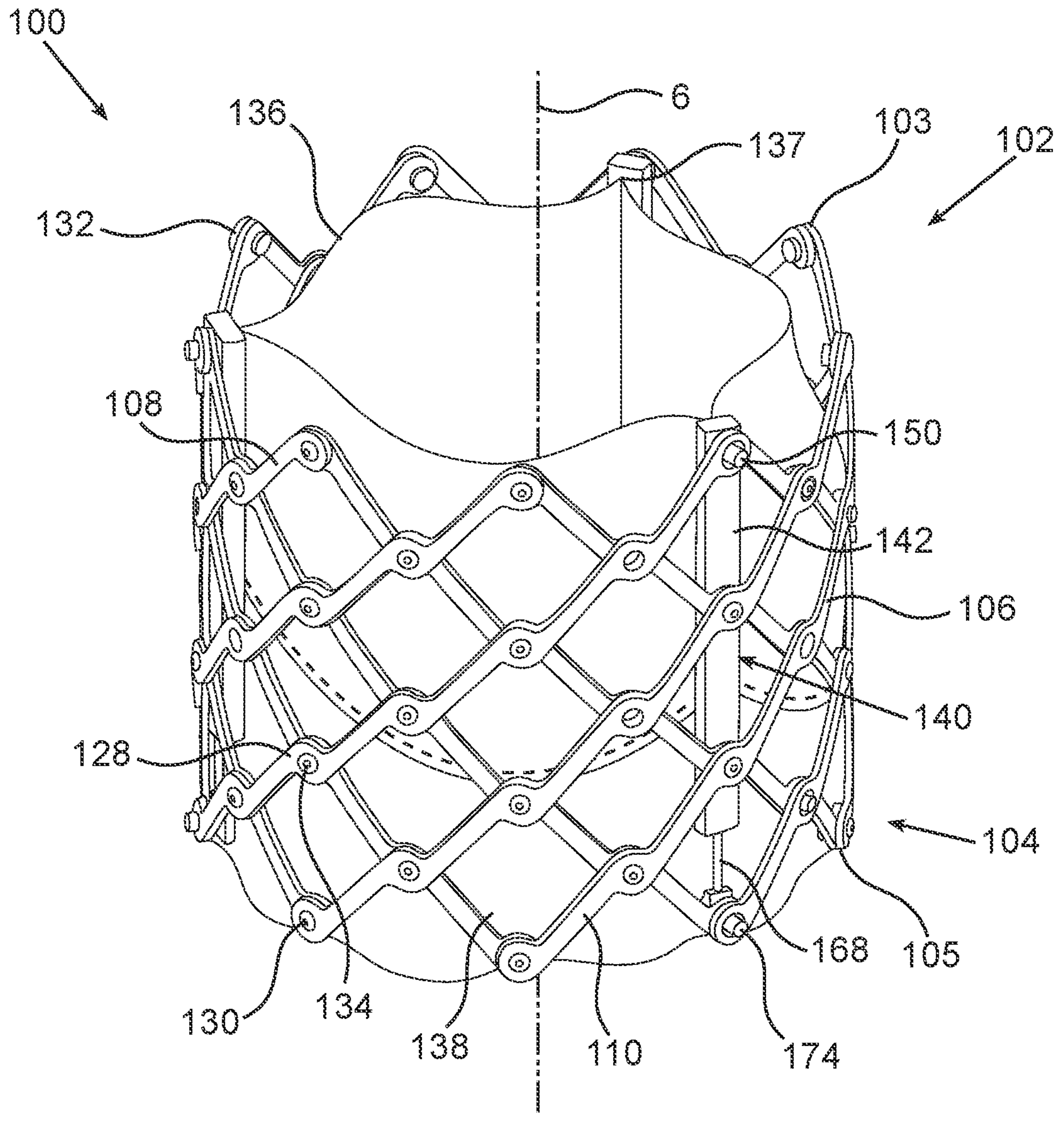
FIG. 2 shows a view in perspective of a prosthetic valve, according to some embodiments.

FIG. 2 shows an exemplary mechanically expandable prosthetic valve 100 in an expanded configuration, according to some embodiments. The prosthetic valve 100 can comprise an inflow end portion 104 defining an inflow end 105, and an outflow end portion 102 defining an outflow end 103. The prosthetic valve 100 can define a valve longitudinal axis 6 extending through the inflow end portion 104 and the outflow end portion 102. In some instances, the outflow end 103 is the distal end of the prosthetic valve 100, and the inflow end 105 is the proximal end of the prosthetic valve 100. Alternatively, depending for example on the delivery approach of the valve, the outflow end can be the proximal end of the prosthetic valve, and the inflow end can be the distal end of the prosthetic valve.

The term "outflow", as used herein, refers to a region of the prosthetic valve through which the blood flows through and out of the valve 100, for example between the valve longitudinal axis 6 and the outflow end 103.

The term "inflow", as used herein, refers to a region of the prosthetic valve through which the blood flows into the valve 100, for example between inflow end 105 and the valve longitudinal axis 6.

The valve 100 comprises a frame 106 composed of interconnected struts 110, and may be made of various suitable materials, such as stainless steel, cobalt-chrome alloy (e.g. MP35N alloy), or nickel titanium alloy such as Nitinol. According to some embodiments, the struts 110 are arranged in a lattice-type pattern. In the embodiment illustrated in FIG. 2, the struts 110 are positioned diagonally, or offset at an angle relative to, and radially offset from, the valve longitudinal axis 6, when the valve 100 is in an expanded configuration. It will be clear that the struts 110 can be offset by other angles than those shown in FIG. 2, such as being oriented substantially parallel to the valve longitudinal axis 6.

According to some embodiments, the struts 110 are pivotably coupled to each other. In the exemplary embodiment shown in FIG. 2, the end portions of the struts 110 are forming apices 132 at the outflow end 103 and apices 130 at the inflow end 105. The struts 110 can be coupled to each other at additional junctions 128 formed between the outflow apices 132 and the inflow apices 130. The junctions 128 can be equally spaced apart from each other, and/or from the apices 130, 132 along the length of each strut 110. Frame 106 may comprise openings or apertures at the regions of apices 130, 132 and junctions 128 of the struts 110. Respective hinges can be included at locations where the apertures of struts 110 overlap each other, via fasteners 134, such as rivets or pins, which extend through the apertures. The hinges can allow the struts 110 to pivot relative to one another as the frame 106 is radially expanded or compressed.

In alternative embodiments, the struts are not coupled to each other via respective hinges, but are otherwise pivotable or bendable relative to each other, so as to permit frame expansion or compression. For example, the frame can be formed from a single piece of material, such as a metal tube, via various processes such as, but not limited to, laser cutting, electroforming, and/or physical vapor deposition, while retaining the ability to collapse/expand radially in the absence of hinges and like.

The frame 106 further comprises a plurality of cells 108, defined between intersecting portions of struts 110. The shape of each cell 108, and the angle between intersecting portions of struts 110 defining the cell borders, vary during expansion or compression of the prosthetic valve 100. Further details regarding the construction of the frame and the prosthetic valve are described in U.S. Publication Nos. 2018/0153689; 2018/0344456; 2019/0060057, all of which are incorporated herein by reference.

A prosthetic valve 100 further comprises one or more leaflets 136, e.g., three leaflets, configured to regulate blood flow through the prosthetic valve 100 from the inflow end 105 to the outflow end 103. While three leaflets 136 arranged to collapse in a tricuspid arrangement, are shown in the exemplary embodiment illustrated in FIG. 2, it will be clear that a prosthetic valve 100 can include any other number of leaflets 136. The leaflets 136 are made of a flexible material, derived from biological materials (e.g., bovine pericardium or pericardium from other sources), bio-compatible synthetic materials, or other suitable materials. The leaflets may be coupled to the frame 106 via commissures 137, either directly or attached to other structural elements connected to the frame 106 or embedded therein, such as commissure posts. Further details regarding prosthetic valves, including the manner in which leaflets may be mounted to their frames, are described in U.S. Pat. Nos. 6,730,113, 7,393,360, 7,510,575, 7,993,394 and 8,252,202, and U.S. Patent Application No. 62/614,299, all of which are incorporated herein by reference.

According to some embodiments, the prosthetic valve 100 may further comprise at least one skirt or sealing member, such as the inner skirt 138 shown in the exemplary embodiment illustrated in FIG. 2. The inner skirt 138 can be mounted on the inner surface of the frame 106, configured to function, for example, as a sealing member to prevent or decrease perivalvular leakage. The inner skirt 138 can further function as an anchoring region for the leaflets 136 to the frame 106, and/or function to protect the leaflets 136 against damage which may be caused by contact with the frame 106, for example during valve crimping or during working cycles of the prosthetic valve 100. Additionally, or alternatively, the prosthetic valve 100 can comprise an outer skirt (not shown) mounted on the outer surface of the frame 106, configure to function, for example, as a sealing member retained between the frame 106 and the surrounding tissue of the native annulus against which the prosthetic valve 100 is mounted, thereby reducing risk of paravalvular leakage past the prosthetic valve 100. Any of the inner skirt 138 and/or outer skirt can be made of various suitable biocompatible materials, such as, but not limited to, various synthetic materials (e.g., PET) or natural tissue (e.g. pericardial tissue).

According to some embodiments, a prosthetic valve 100, which can be a mechanical prosthetic valve, comprises at least one expansion and locking assembly 140, and preferably a plurality of expansion and locking assemblies 140. The expansion and locking assemblies 140 are configured to facilitate expansion of the valve 100, and in some instances, to lock the valve 100 at an expanded configuration, preventing unintentional recompression thereof, as will elaborated in greater detail hereinbelow. Although FIG. 2 illustrates three expansion and locking assemblies 140, mounted to the frame 106, and optionally equally spaced from each other around an inner surface thereof, it should be clear that a different number of expansion and locking assemblies 140 may be utilized, that the expansion and locking assemblies 140 can be mounted to the frame 106 around its outer surface, and that the circumferential spacing between expansion and locking assemblies 140 can be unequal.

Figure 3A:
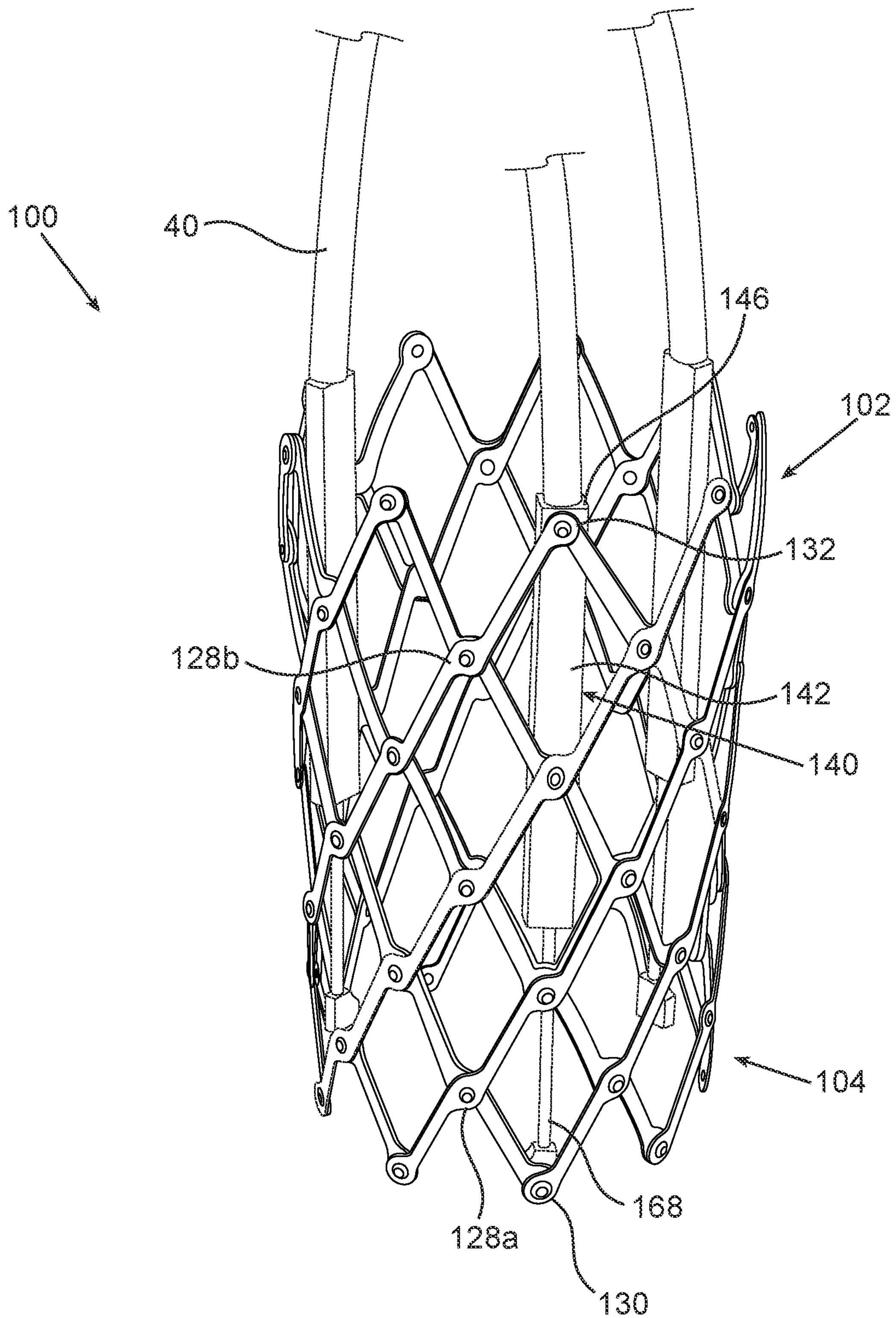
FIG. 3A shows a view in perspective of a prosthetic valve in a partially compressed configuration, having a plurality of expansion and locking assemblies attached to corresponding actuation assemblies, according to some embodiments.
Figure 3B:
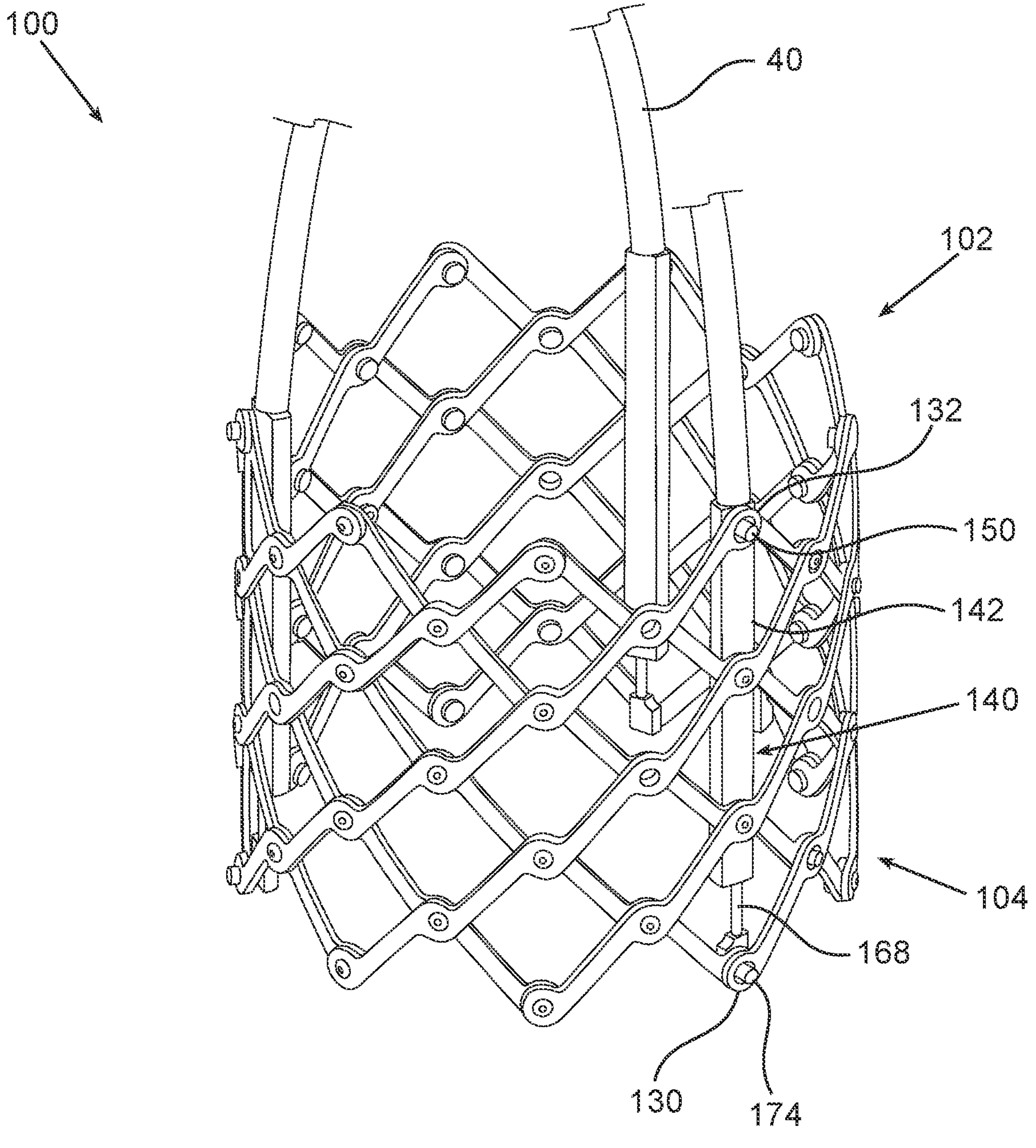
FIG. 3B shows a view in perspective of the prosthetic valve of FIG. 3A, and a fully expanded configuration.

FIGS. 3A-3B illustrate three actuation assemblies 40 coupled to corresponding expansion and locking assemblies 140 attached to a bare frame 106 of the prosthetic valve 100 (without the leaflets and other components), for purposes of illustrating expansion of the prosthetic valve from the radially compressed configuration to the radially expanded configuration. FIG. 3A shows the prosthetic valve 100 in a partially compressed configuration, and FIG. 3B shows the prosthetic valve 100 in a fully expanded configuration. The prosthetic valve 100 in the illustrated configurations can be radially expanded by maintaining the outflow end 103 of the frame 106 at a fixed position while applying a force in the axial direction against the inflow end 105 toward the outflow end 103. Alternatively, the prosthetic valve 100 can be expanded by applying an axial force against the outflow end 103 while maintaining the inflow end 105 at a fixed position, or by applying opposing axial forces to the outflow and inflow ends 103, 105, respectively.

Figure 4:
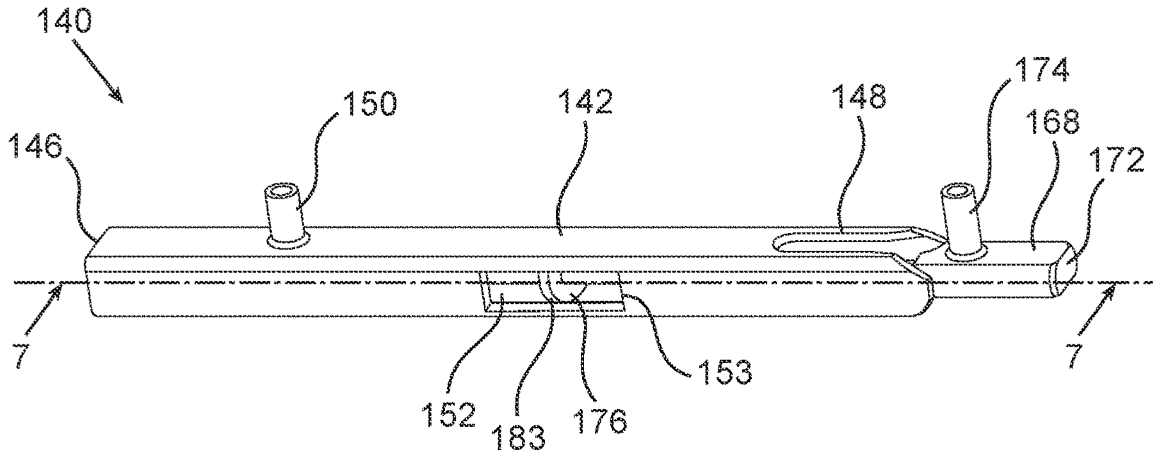
FIG. 4 shows a view in perspective of an expansion and locking assembly, according to some embodiments.
Figure 5A:
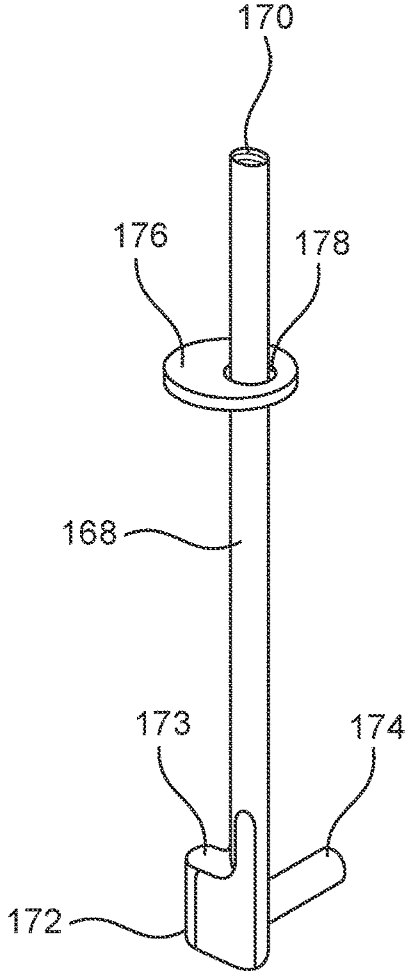
FIG. 5A shows a view in perspective of an inner member, according to some embodiments.
Figure 5B:
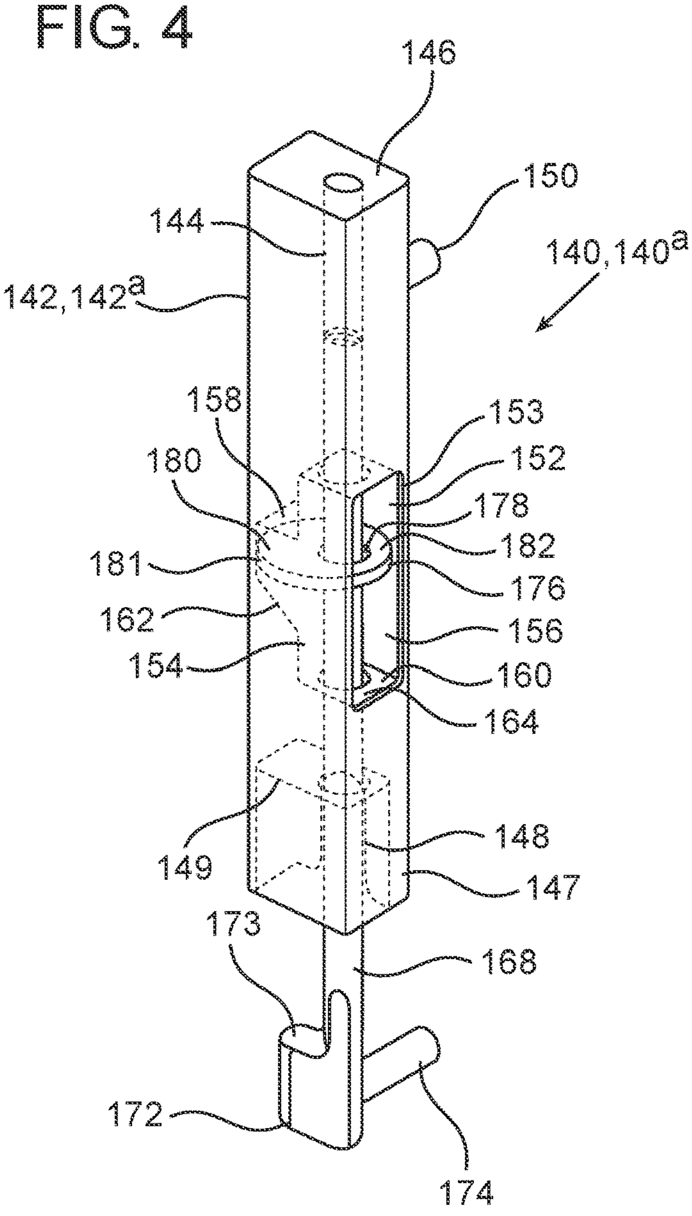
FIG. 5B shows a view in perspective of an expansion and locking assembly, according to some embodiments.

FIGS. 4-5B illustrate an expansion and locking assembly 140, according to some embodiments. FIG. 4 illustrates a view in perspective of an exemplary embodiment of an expansion and locking assembly 140. The expansion and locking assembly 140 includes an outer member 142, coupled to a component of the valve 100, such as the frame 106, at a first location, and an inner member 168 coupled to a component of the valve 100, such as the frame 106, at a second location, axially spaced from the first location. The inner member extends at least partially into the outer member, and at least one of the inner or outer member 168 or 142, respectively, is axially movable relative to the other.

The inner member has an inner member first end, which can be an inner member proximal end portion, and an inner member second end, which can be an inner member distal end portion. The outer member has an outer member first end, which can be an outer member proximal end portion, and an outer member second end, which can be an outer member distal end portion.

FIG. 5A shows a view in perspective of an exemplary inner member 168, having an inner member proximal end portion 170 and an inner member distal end portion 172. The inner member 168 comprises an inner member fastener 174 at its distal end portion 172, which may be formed as a rivet or a pin extending radially outward from the inner member 168, configured to be received within respective openings or apertures of struts 110 intersecting at a junction 128 or an apex 130, 132. The inner member 168 may be provided in the form of a rod having a uniform cross-section between the proximal end portion 170 and the distal end portion 172. While an exemplary embodiment of a rod having a uniform circular cross section is illustrated, it will be clear that the cross-section can be provided with other shapes, including square, rectangular, triangular, pentagonal, hexagonal, octagonal, elliptical, star-shaped, and the like.

FIG. 5B shows the inner member 168 disposed within a lumen of the outer member 142, and more specifically, extending through a primary channel 144 of the outer member 142. The outer member 142 is shown with partial transparency in FIG. 5B to reveal the underlying structures. The outer member 142 comprises an outer member proximal end 146 defining a proximal opening, and an outer member distal end portion 147 defining a distal opening. The outer member 142 can further comprise an outer member fastener 150 proximate to its proximal end 146, which may be formed as a rivet or a pin extending radially outward from the external surface of the outer member 142, configured to be received within respective openings or apertures of struts 110 intersecting at a junction 128 or an apex 132, 130.

It will be understood that while the inner member first end and the inner member second end are exemplified throughout the figures as the inner member proximal end portion 170 and the inner member distal end portion 172, respectively, and while the outer member first end and the outer member second end are exemplified throughout the figures as the outer member proximal end portion 146 and the outer member distal end portion 147, respectively, in alternative configurations, the inner member first end and the inner member second end may be the inner member distal end portion 172 and the inner member proximal end portion 170, respectively, and the outer member first end and the outer member second end may be the outer member distal end portion 147 and the outer member proximal end portion 146, respectively.

The outer member 142 may further comprise a chamber 152 continuous with the primary channel 144, such that one portion of the primary channel 144 extends between the outer member proximal end 146 and the chamber 152, and another portion of the primary channel 144 extends between the chamber 152 and the outer member distal end portion 147.

The chamber 152 comprises a proximal chamber wall 158 and a distal chamber wall 160, and in some implementations, may be exposed to the external environment via a lateral opening 153 formed at a sidewall of the outer member 142 at the region of the chamber 158.

According to some embodiments, the inner member proximal end portion 170 further comprises a threaded bore, configured to receive and threadedly engage with a threaded portion of a distal end portion 44 (shown for example in FIGS. 7A-7D) of a corresponding actuation member 42.

The expansion and locking assembly 140 can include, in some embodiments, one or more engagement surfaces configured to prevent over-expansion of the prosthetic valve 100. For example, in the embodiment illustrated in FIGS. 4-5B, the outer member distal end portion 147 can include a bore having an outer member engagement surface 149. The outer member engagement surface 149 can be configured to engage a corresponding inner member engagement surface 173 to prevent further proximal movement of the inner member 168 relative to the outer member 142, so as to prevent over expansion of the prosthetic valve 100. As shown in the illustrated embodiment, the inner member distal end portion 172 can be formed as a wider portion, relative to the remaining portion of the inner member 168 extending proximally therefrom, defining the inner member engagement surface 173 as the proximally-facing surface of the inner member distal end portion 172.

As shown in FIGS. 4 and 5B, the outer member 142 can further comprise a recess 148 in the wall of the outer member distal end portion 147. The recess 148 can extend through a thickness of the wall of the outer member distal end portion 147 and can extend to its distal edge. In the illustrated exemplary embodiment, the recess is substantially U-shaped, however, in other embodiments the recess can have any of various shapes. The recess 148 can be configured to limit the proximal advancement of the inner member 168 within the outer member 142. For example, as the prosthetic valve 100 expands, the inner member 168 can slide relative to the outer member 142 until the inner member fastener 174 enters the recess 148. The inner member 168 can continue moving relative to the outer member 142 until the inner member fastener 174 abuts a proximal edge of the recess 148, restraining further motion of the inner member 168.

Optionally, and in some embodiments preferably, the expansion and locking assembly 140 further comprises at least one plate 176 having a primary aperture 178, wherein the at least one plate 176 is disposed around the inner member 168, which extends through the primary aperture 178, and is disposed within the chamber 152 of the outer member 142.

Figure 6A:
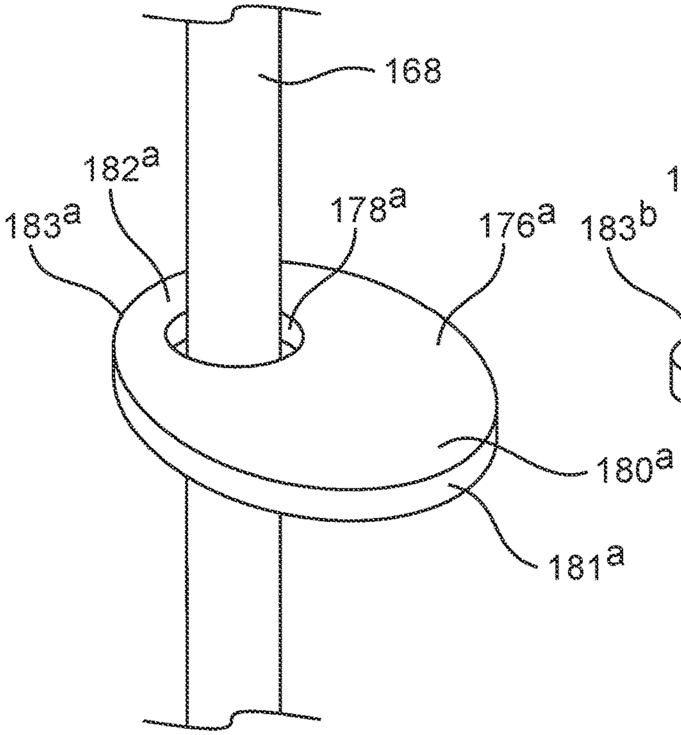
FIGS. 6A-6C show various types and configurations of plates, according to some embodiments.
Figure 6B:
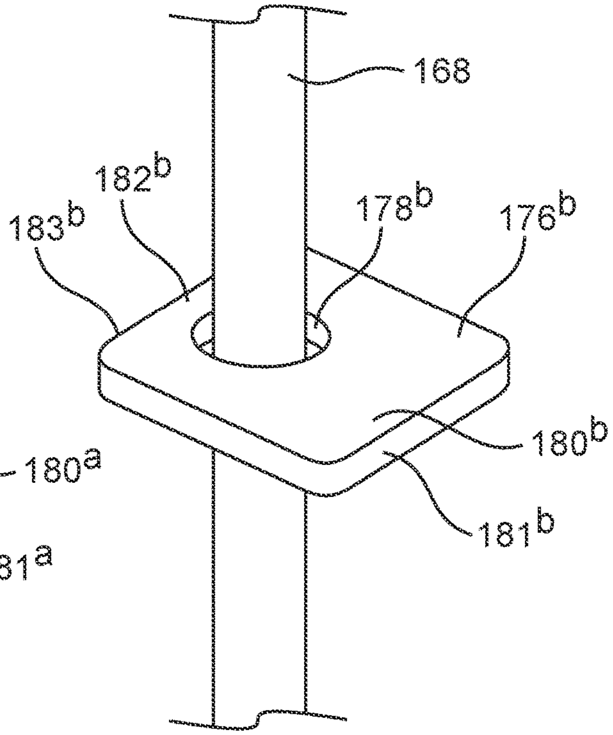
Figure 6C:
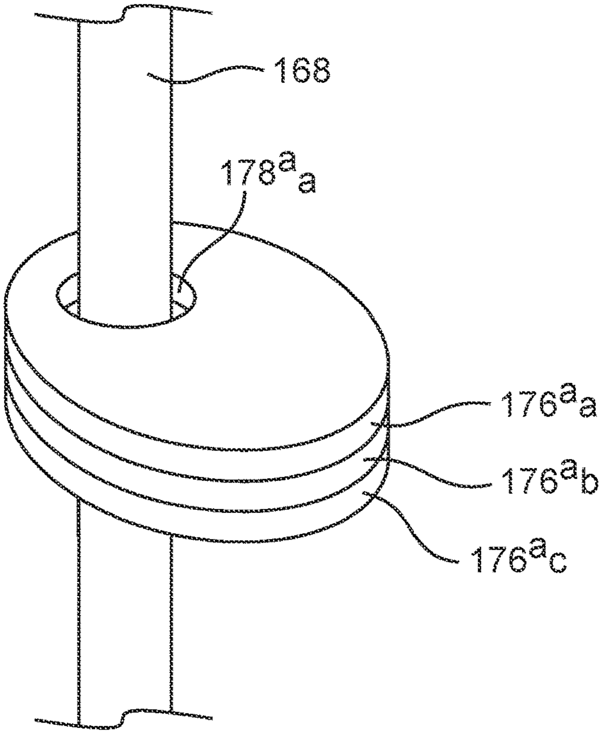

FIGS. 6A-6C illustrate different optional shapes and arrangements of the at least one plate 176. In some embodiments, the plate 176 may have a disc-like circular or elliptic shape, such as plate $\mathbf{176}^{a}$ illustrated in FIG. 6A. In other embodiments, the plate 176 may have a rectangular shape, such as plate $\mathbf{176}^{b}$ illustrated in FIG. 6B. While circular and rectangular shapes are illustrated, it will be clear that the plate 176 may have any other shape, such as a hexagon, other regular-polygon, or any irregular shape, in plan view. The at least one plate 176 typically comprises a rigid biocompatible material. In some applications, the at least one plate 176 comprises a biocompatible metal such as nitinol or stainless steel. In some applications, the at least one plate 176 comprises a plastic.

According to some embodiments, the at least one plate 176 comprises a plurality of plates, such as plates $\mathbf{176}^{a}a$, $\mathbf{176}^{a}b$ and $\mathbf{176}^{a}c$ shown in FIG. 6C. While three plates are illustrated in FIG. 6C, it will be clear that any other number of plates is contemplated, such as two plates, four plates, and so on.

The lateral opening 153 can extend through a thickness of a side wall of the outer member 142, exposing at least a portion of the chamber 152. In the illustrated embodiment, the lateral opening 153 is disposed on a side wall of the outer member 142. However, in other embodiments, the lateral opening 153 can be disposed in any other wall of the outer member 142. In some implementations, the opening 153 can have an elongated rectangular shape as shown in the illustrated embodiment. In other implementations, the lateral opening 153 can have any other shape, such as a circular, ovular, trapezoid and the like. Advantageously, the lateral opening 153 may assist in the process of assembling the expansion and locking assembly 140, by providing access for insertion of the at least one plate 176 there-through into the chamber 152.

According to some embodiments, a method of assembling an expansion and locking assembly 140 includes insertion of at least one plate 176 into the chamber 152 through the opening 153. The plate 176 may be inserted in an inclined orientation, or in a substantially parallel orientation to the longitudinal axis of the outer member 142. Once inside the chamber, the plate can be re-oriented to being substantially orthogonal to the longitudinal axis of the outer member, followed by insertion of the inner member 168 into the outer member 142, through the primary channel 144 of the outer member 142 and through the primary aperture 178 of the at least one plate 176.

The term "longitudinal axis of the outer member", as used herein, refers to an axis which is substantially parallel to the valve longitudinal axis 6 shown in FIG. 2, and extends through the outer member 142.

Figure 7A:
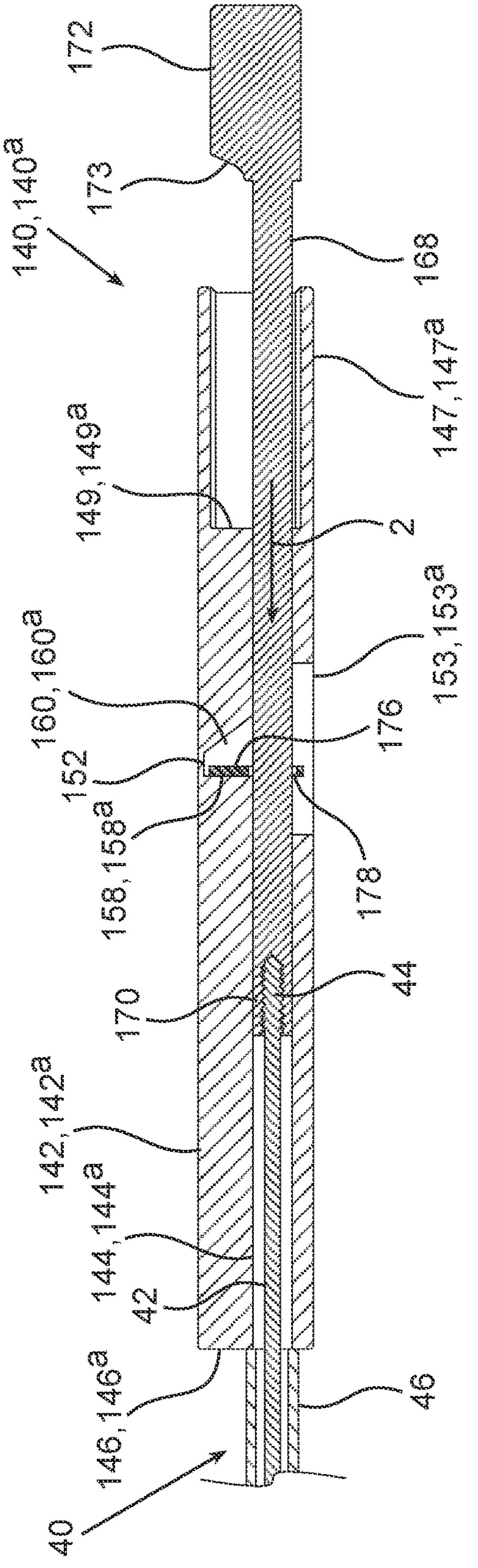
FIGS. 7A-7D show cross-sectional views of an expansion and locking assembly in different operational states thereof, according to some embodiments.

FIGS. 7A-7D show cross-sectional views, taken along line 7-7 of FIG. 4, in various stages of actuating an exemplary embodiments of an expansion and locking assembly 140 to facilitate valve expansion, and potentially lock the valve it in an expanded configuration. FIG. 7A shows an initial state in which the actuation member distal end portion 44 is threaded into a threaded bore of the inner member proximal end portion 170. The inner member 168 extends through the primary channel 144 and the chamber 152 of the outer member 142, such that the inner member fastener 174 is distanced from the outer member fastener 150 at a distance that may be associated with a compressed, or a partially compressed, configuration of the valve 100. In this state, the inner member 168 may extend distally from the outer member 142 such that the inner member fastener 174 is distanced distally away from the outer member distal end 147.

While the outer member fastener 150 and the inner member fastener 174 are not visible in FIGS. 7A-7D, the illustrated configurations show the relative position of the inner member 168 and the outer member 142 when the outer member proximal end 146 is coupled, for example via the outer member fastener 150, to the frame 106 at a first location, and the inner member distal end portion 172 is coupled, for example via the inner member fastener 174, to the frame 106 at a second location.

According to some embodiments, the first location can be positioned at an outflow end portion 102, and the second location can be positioned at the inflow end portion 104. In the embodiment illustrated in FIGS. 2-3B, the outer member 142 is secured to an outflow apex 132 via outer member fastener 150, and the inner member 168 is secured to an inflow apex 130 via inner member fastener 174. In some applications, the outer members 142 may further serve as commissure posts to which commissures 137 may be attached (see FIG. 2).

The chamber 152 may be generally divided into a first zone 154 and a second zone 156, defined as two opposite zones or volumes from both sides of the inner member 168, such that each of the first and second zones 154 and 156, respectively, is defined between the inner member 168 and an opposite inner sidewall of the chamber 152. For example, the second zone 156 may be defined as the space volume between the inner member 168 and the lateral opening 153 (if present), while the first zone 154 may be defined as the space volume between the inner member 168 and the chamber wall opposite to the lateral opening (153). In some implementations, the distal chamber wall 160 may comprise a distal wall first side 162, defined as the portion of the distal chamber wall 164 disposed within the first zone (154), and a distal wall second side 164, defined as the portion of the distal chamber wall 164 disposed within the second zone (156).

According to some embodiments, the distal chamber wall 160 comprises at least one angled portion, defined as a portion which is angled relative to a longitudinal axis of the inner member 168. FIGS. 5B and 7A-7D illustrate an embodiment of an outer member 142$^a$ comprising a distal wall first side 162$^a$ which is angled at proximally-oriented acute angle, relative to a longitudinal axis of the inner member 168.

While the distal chamber wall 160$^a$ is illustrated as having a step-like configuration, wherein the distal wall first side 162$^a$ is angled and the distal wall second side 164$^a$ is substantially orthogonal relative to the longitudinal axis of the inner member 168, it will be clear that in other configurations, the distal wall second side may be continuous with the distal wall first side, such that the entire distal chamber wall may be angled relative to the longitudinal axis of the inner member 168.

The term "longitudinal axis of the inner member", as used herein, refers to an axis which is substantially parallel to the valve longitudinal axis 6 shown in FIG. 2, and extends through the inner member 168.

The plate 176 may also include a plate first side 180 and an opposite plate second side 183, wherein the plate first side 180 is defined as the portion of the plate 176 residing within the first zone 154 of the chamber 152, between the primary aperture 178 and a plate first end 181, and the plate second side 182 is defined as the portion of the plate 176 residing within the second zone 156 of the chamber 152, between the primary aperture 178 and a plate second end 183.

As mentioned with respect to the configuration shown in FIG. 7A, the actuation member distal end portion 44 is threadedly engaged with the threaded bore at the inner member proximal end portion 170. According to some embodiments, as shown in FIGS. 7A-7D, the actuation member distal end portion 44 includes external threads, configured to engage with internal threads of a proximal bore of the inner member proximal end portion 170. According to alternative embodiments, an inner member may include a proximal extension provided with external threads, configured to be received in and engage with internal threads of a distal bore formed within the actuation member (embodiments not shown).

The actuation support sleeve 46 surrounds the actuation member 42 and may be connected to the handle 30. The actuation support sleeve 46 and the outer member 142 are sized such that the distal lip of the actuation support sleeve 46 can abut or engage the outer member proximal end 146, such that the outer member 142 is prevented from moving proximally beyond the actuation support sleeve 46.

In order to radially expand the frame 106, and therefore the valve 100, the actuation support sleeve 46 can be held firmly against the outer member 142. The actuation member 42 can then be pulled in a first direction, such as a proximally oriented direction 2, as shown in FIG. 7A. Since the actuation support sleeve 46 is being held against the outer member 142, which is connected, in the exemplary embodiment, to an outflow apex 132, the outflow end 103 of the frame 106 is prevented from moving relative to the actuation support sleeve 46. As such, movement of the actuation member 42 in the first direction, which is shown to be in the illustrated non-binding example as the proximally oriented direction 2, can cause movement of the inner member 168 in the same direction, thereby causing the frame 106 to foreshorten axially and expand radially.

More specifically, as shown for example in FIG. 3A, the inner member fastener 174 extends through openings in two struts 110 interconnected at an inflow apex 130, while the outer member fastener 150 extends through openings in two struts 110 interconnected at an outflow apex 132. As such, when the inner member 168 is moved axially, for example in a proximally oriented direction 2, within the outer member 142, the inner member fastener 174 moves along with the inner member 168, thereby causing the portion to which the inner member fastener 174 is attached to move axially as well, which in turn causes the frame 106 to foreshorten axially and expand radially.

The struts 110 to which the inner member fastener 174 is connected, are free to pivot relative to the inner member fastener 174 and to one another as the frame 106 is expanded or compressed. In this manner, the inner member fastener 174 serves as a coupling means that forms a pivotable connection between those struts 110. Similarly, struts 110 to which the outer member fastener 150 is connected, are also free to pivot relative to the outer member fastener 150 and to one another as the frame 106 is expanded or compressed. In this manner, the outer member fastener 150 also serves as a coupling means that forms a pivotable connection between those struts 110.

According to some embodiments, the diameter of the primary aperture 178 of the plate 176 is closely matched with the outer diameter of the inner member 168 extending therethrough, such that axial movement of the inner member 168 may frictionally engage with the boundaries of the primary aperture 178 and facilitate axial translation of the plate 176 there-along. In some embodiments, the diameter of the primary aperture is no more than 10 percent larger than the diameter of the inner member 168 at the portion extending therethrough. In some embodiments, the diameter of the primary aperture is no more than 5 percent larger than the diameter of the inner member 168 at the portion extending therethrough.

Pulling the inner member 168 in a proximally oriented direction 2 (which may serve as the first directions, as shown in FIG. 7A) may pull the plate 176 along with the inner member 168, optionally (but not necessarily) until plate 176 is pressed against the proximal chamber wall 158. In some implementations, the proximal chamber wall, or at least a portion thereof, is substantially orthogonal to the longitudinal axis of the inner member, such that when the plate 176 is pressed there-against, the plate 176 also assumes an orientation which is substantially orthogonally to the longitudinal axis of the inner member. In this position, the inner member 168 may be further pulled in a proximal direction 2, slidably moving through the plate 176, which may remain pressed against the proximal surface of the proximal chamber wall 158.

Figure 7B:
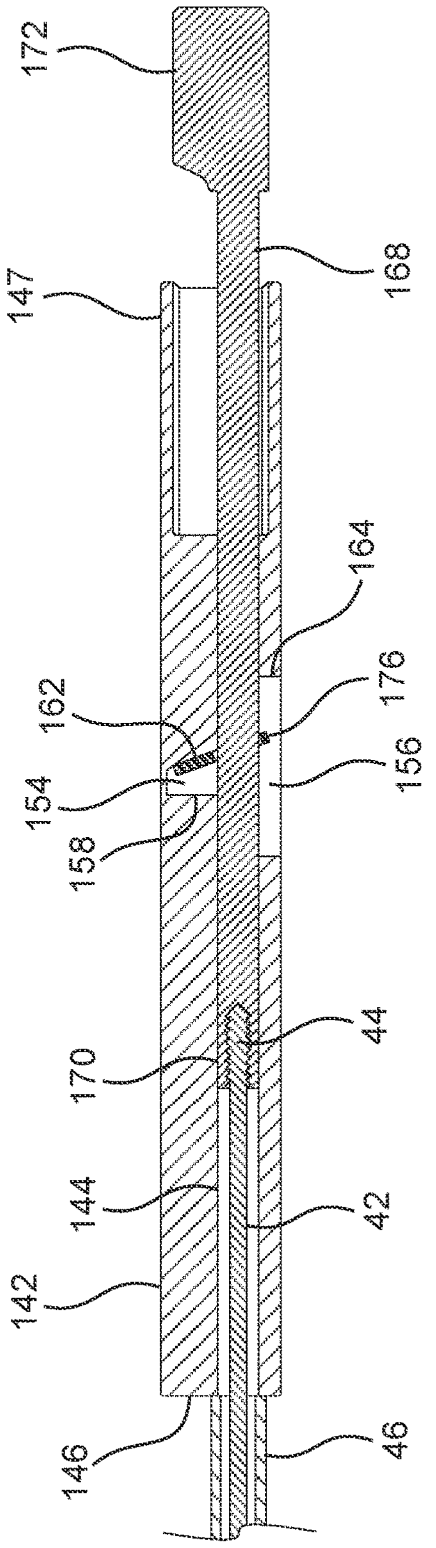

FIG. 7B shows an optional stage in which proximally oriented force is no longer applied by the actuation assembly 40 on the expansion and locking assembly 140, which may occur in a partially expanded configuration of the valve 100. Any attempt aimed at valve re-compression will require distancing the proximal and distal junctions away from each other, for example by moving the inner member 168 in a second direction, such as a distally oriented direction 4, within the outer member 142. Such attempted movement of the inner member 168 in a distal direction may result in axial translation of the plate 176 therewith, for example toward the distal chamber wall 160.

The at least one plate 176 is configured to transition between an angled locking orientation, and a non-locking orientation. Specifically, since the distal wall first side 162 is angled, when the plate first side 180 is pressed there-against—the entire plate 176 assumes an angled locking orientation relative to the longitudinal axis of the inner member 168. Generally, in some implementation, the distal wall first side 162 includes at least one point of contact configured to contact the plate 176, which is proximal relative to any region of the distal wall second side 164 between the primary aperture 178 and the plate second end 183. In this manner, when the plate 176 is pushed in the distal direction to contact the distal chamber wall 160, it assumes an angled locking orientation such that the plate first end 181 is more proximal than the plate second end 183.

Once the plate contacts the distal chamber wall 160, it is tilted to an angled orientation over the inner member 168 until it reaches a self-friction lock angle, inhibiting further advancement of the inner member 168 in the second direction (e.g., the distal direction), which is defined as the angled locking orientation. Thus, the proposed mechanism enables a one-directional axial movement of the inner member 168 in the first direction (e.g., the proximal direction) for valve expansion, while the self-friction lock angle of the at least one plate 176 is configured to lock the valve in the expanded or partially expanded diameter, and prevent unintentional re-compression.

For the sake of simplicity, the first direction will be described in the following exemplary embodiments as the proximally oriented directions 2, and the second direction will be described as the distally oriented direction 4, though in alternative implementations, the expansion and locking assemblies may be designed to operate in reverse, such that the first direction will be the distally oriented direction 4, and the second direction will be the proximally oriented direction 2, mutatis mutandis.

Figure 7C:
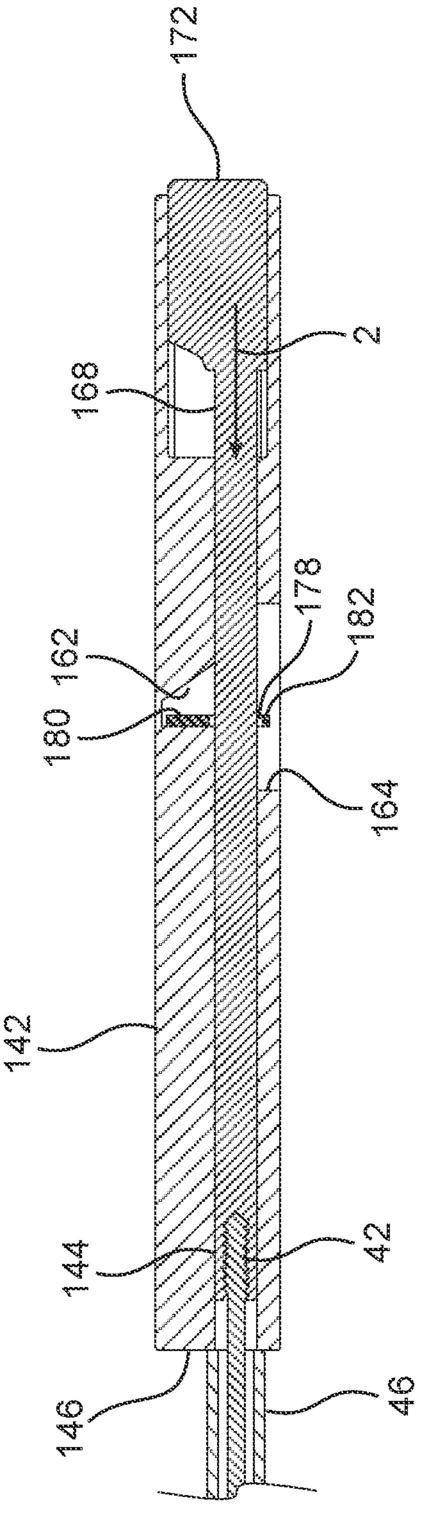

As shown in FIG. 7C, the angled locking orientation of the at least one plate 176 over the inner member 168, prevents movement of the inner member 168 only in the distal direction 4, while further valve expansion is enabled by further pulling the inner member 168 relative to the outer member 142 in the proximal direction 2, for example via the actuation assembly 40 in a similar manner to that described in conjunction with FIG. 7A. When the inner member 168 is pulled in a proximal direction, the at least one plate 176 may transition to a non-locking orientation, which allows free axial movement of the inner member 168 through the primary aperture 178. The non-locking orientation may be either a substantially orthogonal orientation of the at least one plate 176 relative to the longitudinal axis of the inner member, or any other angled orientation of the at least one plate 176 relative to the inner member 168 at an angle which is between the self-friction lock angle and an obtuse angle with respect to the longitudinal axis of the inner member, and may thus allow axial movement of the inner member 168 there-through.

While the plate 176 is shown in FIGS. 7A and 7C pressed against the proximal chamber wall 158, for example due to frictional forces formed between the inner wall of the primary aperture 178 and the outer surface of the inner member 168, it will be clear that in practice this may not necessarily be the case, and that the plate 176 may be otherwise positioned elsewhere between the proximal chamber wall 158 and the distal chamber wall 160, oriented in either a substantially orthogonal orientation relative to the inner member 168, or angled relative thereto in another orientation which is not the angle-locking orientation. For example, the plate 176 can be angled at any angle between the angle-locking orientation shown in FIG. 7B and the orthogonal orientation shown in FIG. 7A, as long as such orientation of the plate 176 allows the inner member 168 to translate axially, for example in the proximally oriented direction 2, through the primary aperture 178.

Figure 7D:
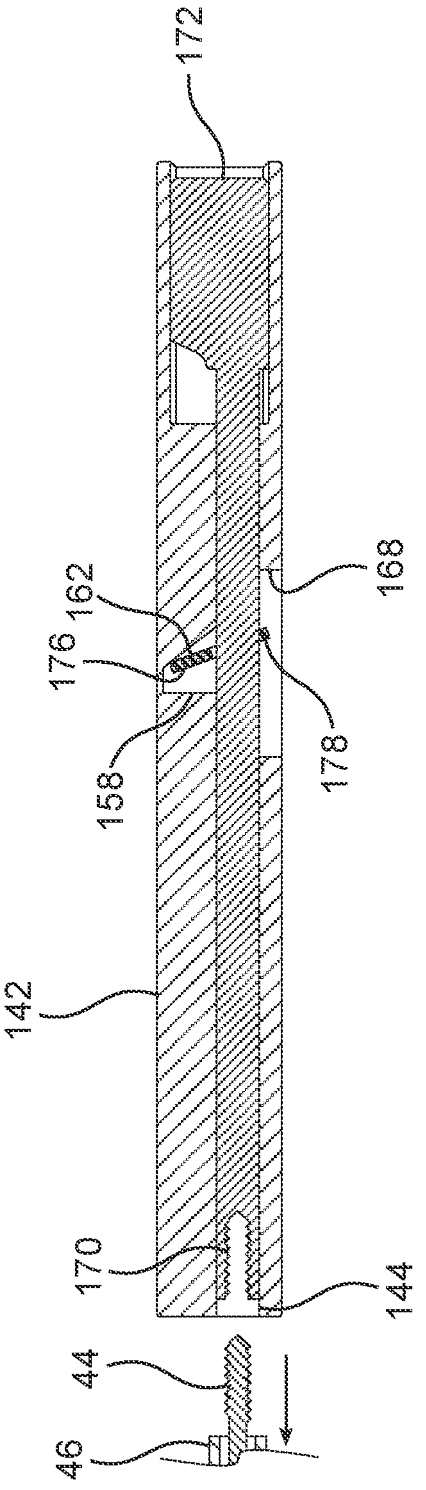

FIG. 7D shows the inner member 168 positioned at a more proximal position relative to its position within the outer member 142 shown in FIGS. 7A-7B, which may represent a fully expanded configuration of the valve in FIG. 7D. In the illustrated state, pulling force in the proximal direction is no longer applied to the inner member 168. When an external force (e.g., applied by the surrounding anatomy) strives to re-compress the valve (100), thereby distancing the proximal and distal junctions away from each other, the plate 176 may be once again pushed against the distal chamber wall 160, assuming an angled locking orientation which serves to lock the expansion and locking assembly 140 and retain the valve 100 in the expanded configuration.

Once the desired diameter of the prosthetic valve 100 is reached, the actuation member 42 may be rotated about its axis to unscrew the actuation member 42 from the inner member 168, as shown in FIG. 7D. This rotation serves to disengage the threaded actuation member distal end portion 44 from the threaded bore of the inner member proximal end portion 170, enabling the actuation assemblies 40 to be pulled away, and retracted, together with the delivery apparatus 12, from the patient's body, leaving the prosthetic valve (100) implanted in the patient.

The patient's native anatomy, such as the native aortic annulus in the case of transcatheter aortic valve implantation, may exert radial forces against the prosthetic valve 100 that would strive to compress it. However, the self-friction lock angle assumed by the plate 176 in the angled locking orientation, causes the inner borders of the primary aperture to press against and/or frictionally engage with the outer surface of the inner member 168, so as to prevent such forces from compressing the frame 106, thereby ensuring that the frame 106 remains locked in the desired radially expanded configuration.

Thus, the prosthetic valve 100 is radially expandable from the radially compressed configuration shown in FIG. 7A to the radially expanded configuration shown in FIG. 7D, upon actuation of the actuator assemblies 40, wherein such actuation includes approximating the second locations (e.g., inflow apices 130) to the first locations (e.g., outflow apices 132) of the valve. The prosthetic valve 100 is further releasable from the delivery apparatus 12 by decoupling each of the actuation members 42 from each corresponding expansion and locking assembly 140 that was attached thereto.

The terms coupled, engaged, connected and attached, as used herein, are interchangeable. Similarly, the term decoupled, disengaged, disconnected and detached, as used herein, are interchangeable.

According to some embodiments, as illustrated, the angled portion of the distal chamber wall 160, e.g. the distal wall first side 162, is oriented at an angle which is more acute, with respect to the longitudinal axis of the inner member (168), relative to the self-friction lock angle, formed between the plate 176 and the longitudinal axis of the inner member (168) at the angled locking orientation. In such embodiments, the plate first end 181 may contact the distal wall first side 162 in the angled locking orientation, while the remainder of the plate 176 may remain offset from the distal chamber wall 160. In alternative implementations, the angled portion of the distal chamber wall 160 may be angled at an angle which is substantially equal to the self-friction lock angle, such that a larger portion of the plate 176, e.g. the complete distal surface of the plate first side 180, may contact the distal wall first side 162 in the angled locking orientation.

It is to be understood that any reference to angles throughout the current disclosure, refers to angles facing the first direction, i.e., angled facing the proximal direction 2 in the illustrated embodiments.

While the inner member 168 and the outer member 142 are shown in the illustrated embodiment of FIGS. 2-3B connected to an inflow apex 130 and an outflow apex 132, respectively, it should be understood that they can be connected to other junctions 128 of the frame 106. For example, the inner member fastener 174 can extend through openings formed in interconnected struts at a junction 128 at the inflow end portion 104, proximal to the inflow apices 130. Similarly, the outer member fastener 150 can extend through openings formed in interconnected struts at a junction 128 at the outflow end portion 102, distal to the outflow apices 132.

While the frame is shown in the illustrated examples to expand radially outward by axially moving the inner member 168 in a proximally oriented direction 2, relative to the outer member 142, it will be understood that similar frame expansion may be achieved by axially pushing an outer member 142 in a distally oriented direction, relative to an inner member 168. Moreover, while the illustrated embodiments in FIGS. 2-3B show the outer member 142 affixed to an outflow end portion 102 of the frame 106, and an inner member 168 affixed to an inflow end portion 104 of the frame 106, in alternative embodiments, the outer member 142 may be affixed to the inflow end portion 104 of the frame 106, while the inner member 168 may be affixed to the outflow end portion 102 of the frame 106.

According to some embodiments, the inner surface of the primary aperture 178 of the plate 176, and/or the outer surface of the inner member 168 extending through the primary aperture 178, further comprises a texture and/or friction-enhancement features (not shown), configured to promote or enhance frictional engagement there-between.

The outer member 142 in the illustrated embodiments is shown to have a rectangular shape in cross-section, and the inner member 168 is shown to have a circular shape in cross-section corresponding to the shape of the primary channel 144. As shown in FIGS. 2-3A, a rectangular cross-section of the outer members 142 can advantageously minimize the distance that the expansion and locking assemblies extend into the lumen of the frame 106, which can reduce the overall crimp profile of the valve 100. However, in other embodiments the outer member 142 and/or the inner member 168 can have any of various corresponding shapes in cross-section, for example, circular, ovular, triangular, rectangular, square, or combinations thereof.

According to some embodiments, the handle 30 can comprise control mechanisms which may include steerable or rotatable knobs 32, levers, buttons and such, which in some implementation may be manually controllable by an operator to produce axial and/or rotatable movement of different components of the delivery apparatus 12. For example, the embodiment of handle $\mathbf{30}^a$ illustrated in FIG. 1 comprises first, second, third and fourth knobs $\mathbf{32}^a a$, $\mathbf{32}^a b$, $\mathbf{32}^a c$ and $\mathbf{32}^a d$, respectively.

Knob $32^a a$, shown in FIG. 1, can be a rotatable knob configured to produce bi-directional axial translation of the outer shaft 20 relative to the prosthetic valve 100 in the distal and/or proximal directions, for example to retract the outer shaft 20 and expose the prosthetic valve 100 once it is positioned at or adjacent the desired site of implantation within the patient's body. For example, rotation of the knob $32^a a$ in a first direction (e.g., clockwise) can retract the outer shaft 20 proximally relative to the prosthetic valve 100, and rotation of the knob $32^a a$ in a second direction (e.g., counterclockwise) can advance the outer shaft 20 distally.

Knob $32^a b$, shown in FIG. 1, can be a rotatable knob configured to steer the outer shaft 20 as it advances through the curvatures of the patient's vasculature. Particularly, the handle 30 may comprise, in some embodiments, a steering mechanism, which may include at least one pull wire (not shown) attached at its distal end to the outer shaft 20 (or other shafts of the delivery apparatus 12), such that rotation of the knob $32^a b$ may vary the tension of the pull wire, which is effective to vary the curvature of the outer shaft 20.

Knob $32^a d$, shown in FIG. 1, can be a rotatable knob configured to produce radial expansion and/or contraction of the prosthetic valve 100. For example, rotation of the knob $32^a d$ can move the actuation member 42 and the actuation support sleeve 46 axially relative to one another. Rotation of the knob $32^a d$ in a first direction (e.g., clockwise) can radially expand the prosthetic valve 100, and rotation of the knob $32^a d$ in a second direction (e.g., counterclockwise) can radially contract or re-compress the prosthetic valve 100.

Knob $32^a c$, shown in FIG. 1, can be a rotatable knob configured to release the prosthetic valve 100 from the delivery apparatus 12. For example, rotation of the knob $32^a c$ in a first direction (e.g., clockwise) can disengage the actuation assemblies 40 from the expansion and locking assemblies 140 of the prosthetic valve 100.

The handle 30 may include more or less than the four knobs 32 described herein above, configured to fulfill only some of the functionalities described for knobs 32*a*, 32*b*, 32*c* and 32*d*, and/or additional functionalities. Any of the knobs 32*a*, 32*b*, 32*c* and 32*d* may be implemented, in alternative embodiments, as other types of buttons, levers, knobs and the like, such as push/pull knobs which may be actuated by sliding or moving the knobs axially.

According to other embodiments, control mechanisms in the handle 30 and/or other components of the delivery apparatus 12 can be electrically, pneumatically and/or hydraulically controlled. According to some embodiments, the handle 30 can house one or more electric motors which can be actuated by an operator, such as by pressing a button or a switch on the handle 30, to produce movement of components of the delivery apparatus 12. For example, the handle 30 may include one or more motors operable to produce linear movement of components of the actuation assemblies 40, and/or one or more motors operable to produce rotational movement of the actuation members 42 to disconnect the threaded actuation member distal end portion 44 from the inner member proximal end portion 170. According to some embodiments, one or more manual or electric control mechanism is configured to produce simultaneous linear and/or rotational movement of all of the actuation members 42.

Optionally, but in some embodiments preferably, the expansion and locking assembly 140 further comprises at least one spring 186 disposed within the chamber 152, configured to urge the at least one plate 176 in a second direction so as to assume an angled locking orientation, for example by urging it against the distal chamber wall 160. The spring constant may be chosen to exert a force sufficient to press the at least one plate 176 against the distal chamber wall 160 in the absence of an external proximally oriented force applied to the at least one plate 176, resulting in a transition of the at least one plate 176 to the angled locking orientation, and to allow transition of the at least one plate 176 to a non-locking orientation upon application of an external proximally oriented force either directly to the plate 176, or indirectly by pulling the inner member 168 in the proximal direction, for example via the actuation assembly 40.

For sake of simplicity, the term "plate", as used throughout the current specification, may refer to either a single plate (as shown, for example, in FIGS. 6A-6B), or a plurality of plates (as shown, for example, in FIG. 6C).

Figure 8A:
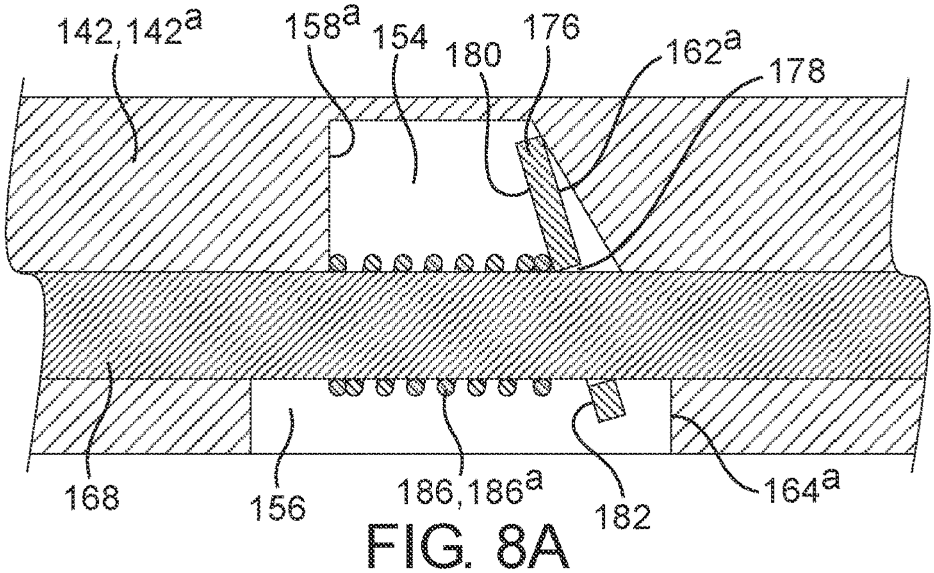
FIGS. 8A-8C show cross-sectional views of a portion of an expansion and locking assembly containing the chamber, provided with various types and arrangements of a helical spring, according to some embodiments.
Figure 8B:
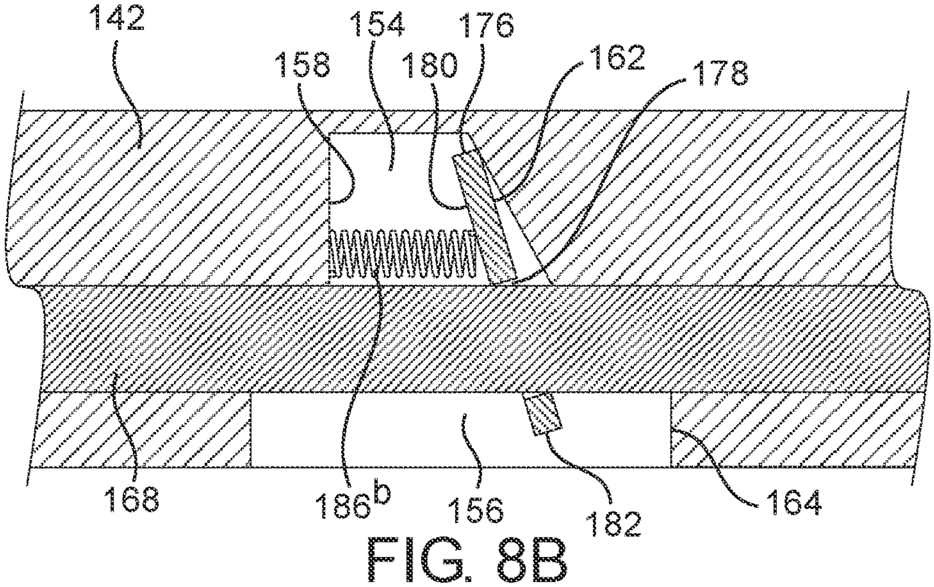
Figure 8C:
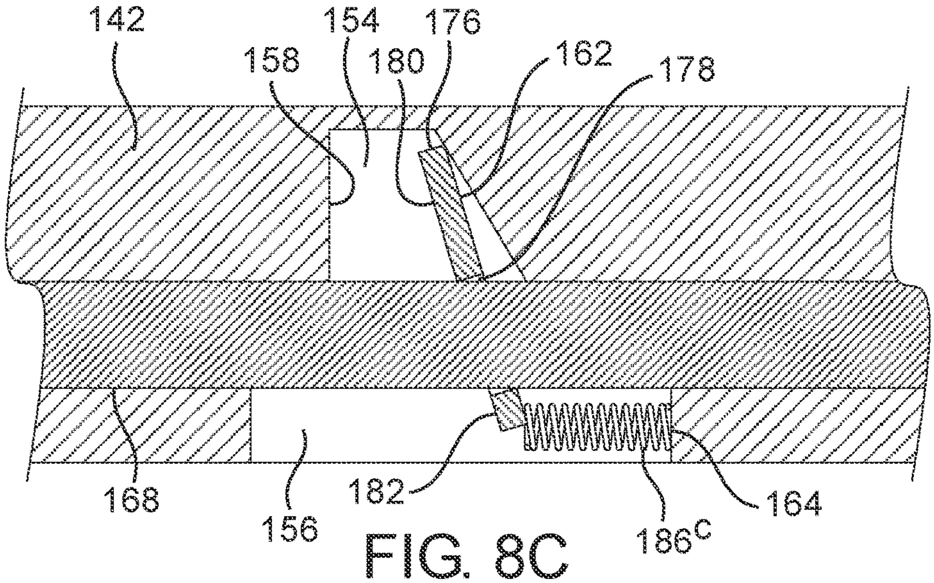

The spring 186 may be disposed between the plate 176 and either one of: the proximal chamber wall 158 or the distal chamber wall 160. According to some embodiments, the spring 186 is a helical spring. FIGS. 8A-8C show various exemplary types and arrangements of a helical spring 186. FIG. 8A shows an exemplary embodiment of a helical spring $186^a$ coiled around the inner member 168, such that the inner member 168 extends through the coils of the spring $186^a$. The spring $186^a$ shown in FIG. 8A is a compression spring disposed between the proximal chamber wall 158 and the plate 176, and may be affixed to either the proximal chamber wall 158 and/or the plate 176, configured to push the plate 176 toward the distal chamber wall 160, so as to orient it in the illustrated angled locking orientation.

FIG. 8B shows an exemplary embodiment of a helical spring $186^b$ adjacent the inner member 168. The spring $186^b$ shown in FIG. 8B is a compression spring disposed between the proximal chamber wall 158 and the plate 176, and more specifically, disposed within the first zone 154 between the proximal chamber wall 158 and the plate first side 180, and may be affixed to either the proximal chamber wall 158 and/or the plate 176 (for example, to the plate first side 180), configured to push the plate 176 toward the distal chamber wall 160, so as to orient it in the illustrated angled locking orientation.

FIG. 8C shows another exemplary embodiment of a helical spring $186^c$ adjacent the inner member 168. The spring $186^c$ shown in FIG. 8C is an extension spring disposed between the distal chamber wall 160 and the plate 176, and more specifically, disposed within the second zone 156 between the distal wall second side 164 and the plate second side 182, and may be affixed to either the distal chamber wall 160 (for example, to the distal wall second side 164) and/or the plate 176 (for example, to the plate second side 182), configured to pull the plate 176 toward the distal chamber wall 160, so as to orient it in the illustrated angled locking orientation. The proximal end of the spring $186^c$ may be coupled to the plate 176 (for example, to the plate second side 182), and the distal end of the spring may be coupled to the distal chamber wall 160 (for example, to the distal wall second side 164).

It will be clear that the embodiments illustrated in FIGS. 8A-8C are merely exemplary, and that other arrangements and embodiments are contemplated, such as a helical spring 186 coiled around the inner member 168, in a similar manner to that shown in FIG. 8A, but implemented as an extension spring disposed between the distal chamber wall 160 and the plate 176, configured to pull the plate 176 toward the distal chamber wall 160.

Figure 9A:
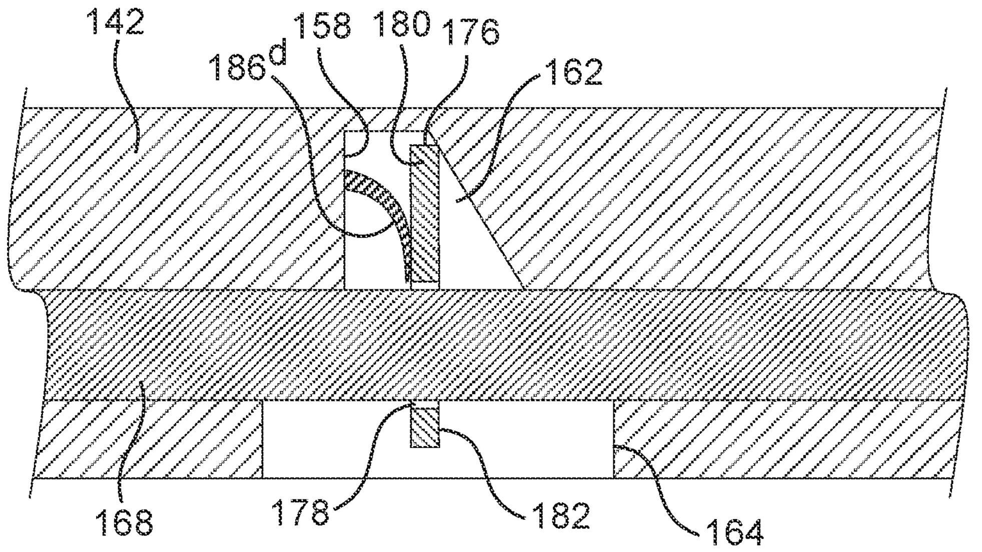
FIGS. 9A-9B show cross-sectional views of an expansion and locking assembly containing the chamber, provided with a leaf spring shown in two states thereof, according to some embodiments.
Figure 9B:
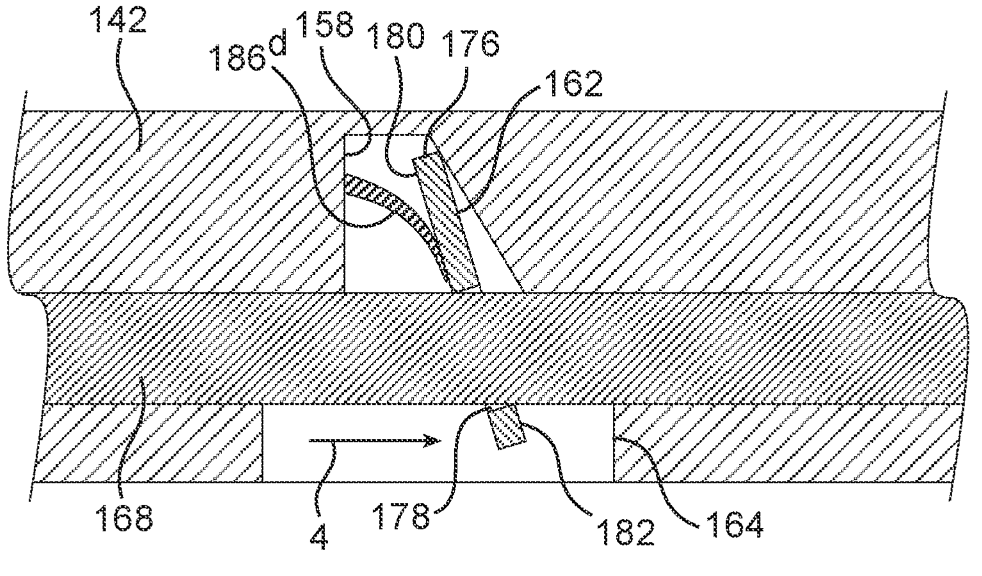

According to some embodiments, the spring 186 is a leaf spring. FIGS. 9A-9B shows a leaf spring $186^d$ disposed between the proximal chamber wall 158 and the plate 176.

FIG. 9A shows the plate 176 in a non-locking orientation, for example during application of a proximally oriented pull-force on the inner member 168, while FIG. 9B shows the plate 176 pushed by the leaf spring 186$^d$ toward the distal chamber wall 160, so as to orient it in the illustrated angled locking orientation. The leaf spring 186$^d$ may be attached, at its proximal end, to the proximal chamber wall 158.

While FIGS. 9A-9B illustrate an embodiment of the leaf spring 186$^d$ configured to contact the plate first side 180 to urge it toward the distal wall first side 162, other embodiments are contemplated, such as a leaf spring provided with an aperture through which the inner member 168 can extend, configured to contact portions of the plate 176 that may be in the vicinity of the primary aperture 178, so as to urge it toward the distal chamber wall 160 (embodiments not shown).

Figure 10A:
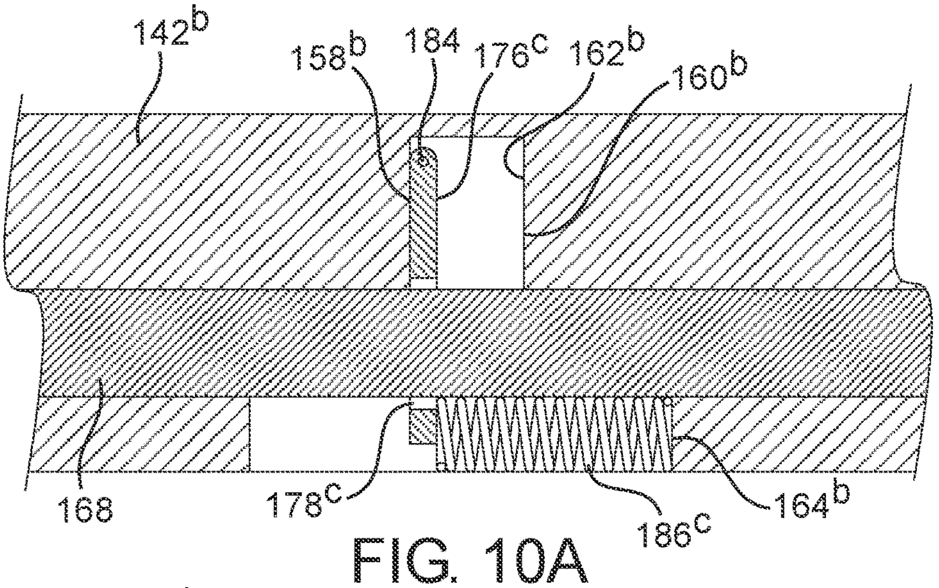
FIGS. 10A-10B show cross-sectional views of an expansion and locking assembly containing the chamber, provided with a plate pivotably attached to a proximal chamber wall shown in two states thereof, according to some embodiments.
Figure 10B:
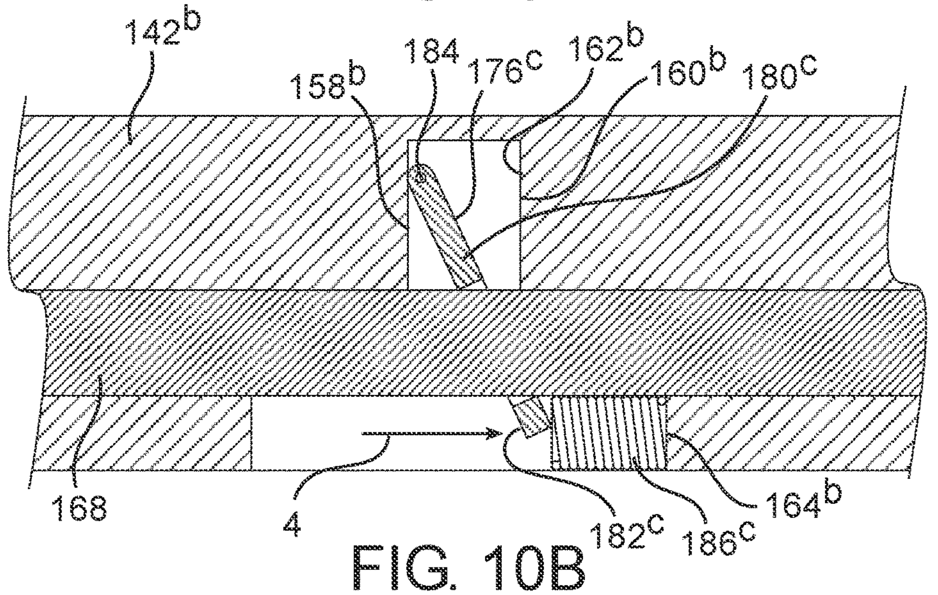

According to some embodiments, the plate 176 is coupled to a wall of the chamber 158 via a plate hinge 184, configured to pivot about the hinge 184 between the non-locking orientation and the angled locking orientation. FIGS. 10A-10B show a plate 176$^c$, coupled to the proximal chamber wall 158$^b$ of the outer member 142$^b$ at a plate hinge 184. Optionally, a spring 186 may be added to urge the plate 176$^c$ toward the distal chamber wall 160.

FIG. 10A shows the plate 176$^c$ in a non-locking orientation, for example during application of a proximally oriented pull-force on the inner member 168, while FIG. 10B shows the plate second side 182$^c$ pulled in the distal direction 4 by a spring 186$^c$ (similar to the arrangement illustrated and described in conjunction with FIG. 8C), thereby pivoting the plate 176$^c$ about the hinge 184 to the angled locking orientation.

As shown in FIGS. 10A-10B, when a plate 176$^c$ is attached to a wall of the chamber 152 via a plate hinge 184, the distal chamber wall 160 does not necessarily need to include a feature configured to orient the plate 176$^c$ in the angle locking orientation. For example, the distal chamber wall 160$^c$ illustrated in FIGS. 10A-10B does not include any angled portions, since the plate 176$^c$ does not even need to contact the distal chamber wall 160$^c$ at any point to transition to the angled locking orientation of FIG. 10B. In fact, in some implementations, the chamber may include a proximal chamber wall, but may be open ended in the distal direction, without any distal chamber wall.

Figure 11:
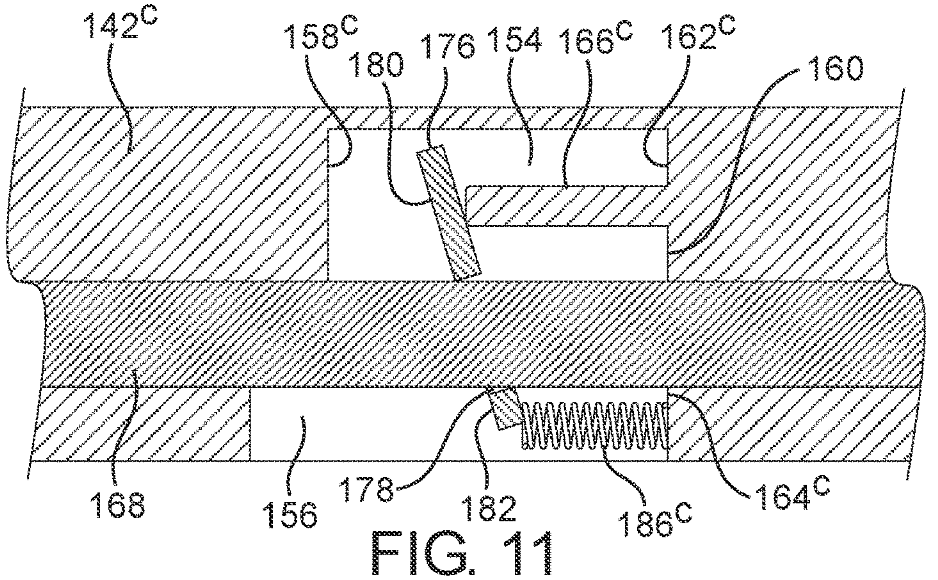
FIG. 11 shows a cross-sectional view of a portion of an expansion and locking assembly containing the chamber, provided with a proximally oriented protrusion extending from the distal chamber wall, according to some embodiments.

According to some embodiments, the distal chamber wall 160 may include features other than an inclined distal wall first side 162, configured to transition the plate 176 in the angled locking position when pressed there-against, such as a proximally oriented protrusion 166 extending proximally from the distal wall second side 164. FIG. 11 shows an embodiments of an outer member 142$^c$ comprising a proximally oriented protrusion 166$^c$ extending from the distal chamber wall 160$^d$, and more specifically, from the distal wall first side 162$^c$. Optionally, a spring 186 may be added to urge the plate 176$^c$ toward the distal chamber wall 160.

As shown in FIG. 11, when the plate 176, and more specifically, the plate first side 180, is pressed against the proximally oriented protrusion 166$^c$, the plate 176 transitions to the angled locking orientation, optionally by the plate second side 182 being pulled in the distal direction 4 by a spring 186$^c$ (similar to the arrangement illustrated and described in conjunction with FIG. 8C).

Figure 12A:
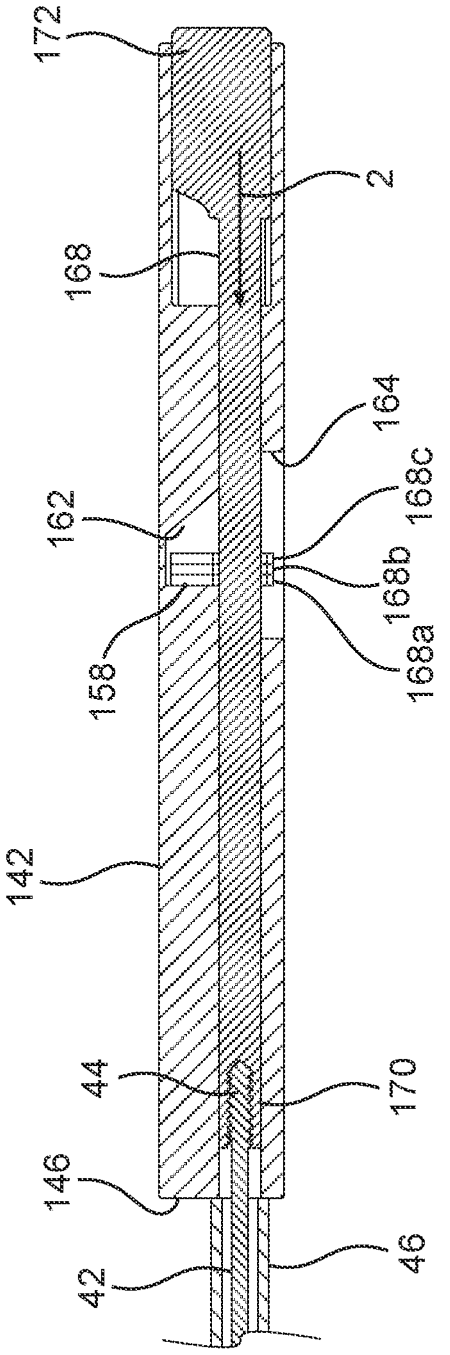
FIGS. 12A-12B show cross-sectional views of an expansion and locking assembly provided with a plurality of plates, in different operational states thereof, according to some embodiments.
Figure 12B:
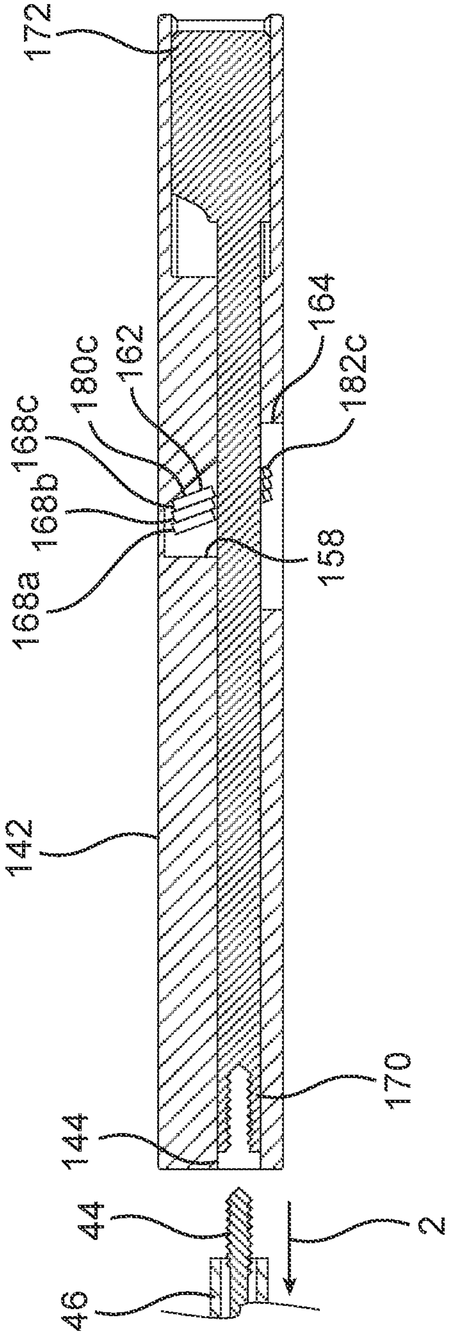

FIGS. 12A-12B show cross-sectional views of different phases during and after actuation of an actuating the expansion and locking assembly which comprises a plurality of plates 176, such as three plates 176*a*, 176*b* and 176*c*, instead of a single plate 176 shown for example in FIGS. 7A-7D. In the actuation state shown in FIG. 12A, the actuation member distal end portion 44 is threadedly engaged with the threaded bore at the inner member proximal end portion 170. The actuation member 42 may be pulled in a proximally oriented direction 2, while the actuation support sleeve 46 is held firmly against the outer member 142 so as to prevent the outflow end 103 of the frame 106 from moving relative to the actuation support sleeve 46. As such, movement of the actuation member 42 in a proximally oriented direction 2 causes movement of the inner member 168 in the same direction, thereby causing the frame 106 to foreshorten axially and expand radially.

Pulling the inner member 168 in a proximally oriented direction 2 (as shown in FIG. 12A) may pull at least one of the plurality of plates 176, and potentially all of the plurality of plates 176, along with the inner member 168, optionally (but not necessarily) until at least the most proximal plate 176 is pressed against the proximal chamber wall 158.

FIG. 12B shows the inner member 168 positioned at a more proximal position relative to its position within the outer member 142 shown in FIG. 12A. In the illustrated state, pulling force in the proximal direction is no longer applied to the inner member 168. When an external force (e.g., applied by the surrounding anatomy) strives to re-compress the valve (100), thereby distancing the proximal and distal junctions away from each other, at least one of the plurality of plates 176, and potentially all of the plates 176, are pushed against the distal chamber wall 160, assuming an angled locking orientation which serves to lock the expansion and locking assembly and retain the valve (100) in the expanded configuration. Thereafter, the actuation member 42 may be rotated about its axis to unscrew it from the inner member 168, enabling the actuation assemblies 40 to be pulled away and retracted, together with the delivery apparatus 12, from the patient's body, leaving the prosthetic valve (100) implanted in the patient.

Advantageously, a plurality of plates 176, comprised within a single chamber 152, may provide several points of contact between the inner boundaries of the corresponding primary aperture 178 and the inner member 168 in the angled locking state of the plates 176, thereby providing a higher friction-force there-between to improve reliability of the locked state of the expansion and locking assemblies. While three plates 176*a*, 176*b* and 176*c* are shown in FIGS. 12A-12B, it will be clear that any other number of plates is contemplated. Moreover, the plurality of plates 176 can be of any type disclosed herein, such as a plurality of disc-like circular or oval-shaped plates 176$^a$ shown in FIG. 6C, a plurality of rectangularly shaped plates 176$^b$, or any other type of plates.

Prior to implantation, the prosthetic valve 100 can be crimped onto the delivery apparatus 12. This step can include placement of the radially compressed valve 100 within the outer shaft 20. Once delivered to the site of implantation, such as a native annulus, the valve 100 can be radially expanded within the annulus, for example, by the expansion and locking assemblies 140 in the manner described herein above. However, during such implantation procedures, it may become desirable to re-compress the prosthetic valve 100 in situ in order to reposition it. Valve re-compression may be achievable only if the inner members 168 are allowed to axially translate in a distally oriented direction 4 (i.e., in the second direction), relative to the outer members 142, which in turn can occur only if the plates 176 are released from the angled locking orientations to the non-locking orientations.

According to some embodiments, the delivery assembly comprises at least one release assembly 50, and preferably a plurality release assemblies 50, detachably attached to corresponding release members 188 extending through the outer members 142 of expansion and locking assemblies 140, and configured to transition the plates 176 from an angled locking orientation to a non-locking orientation, so as to allow re-compression of the prosthetic valve 100.

Figure 13:
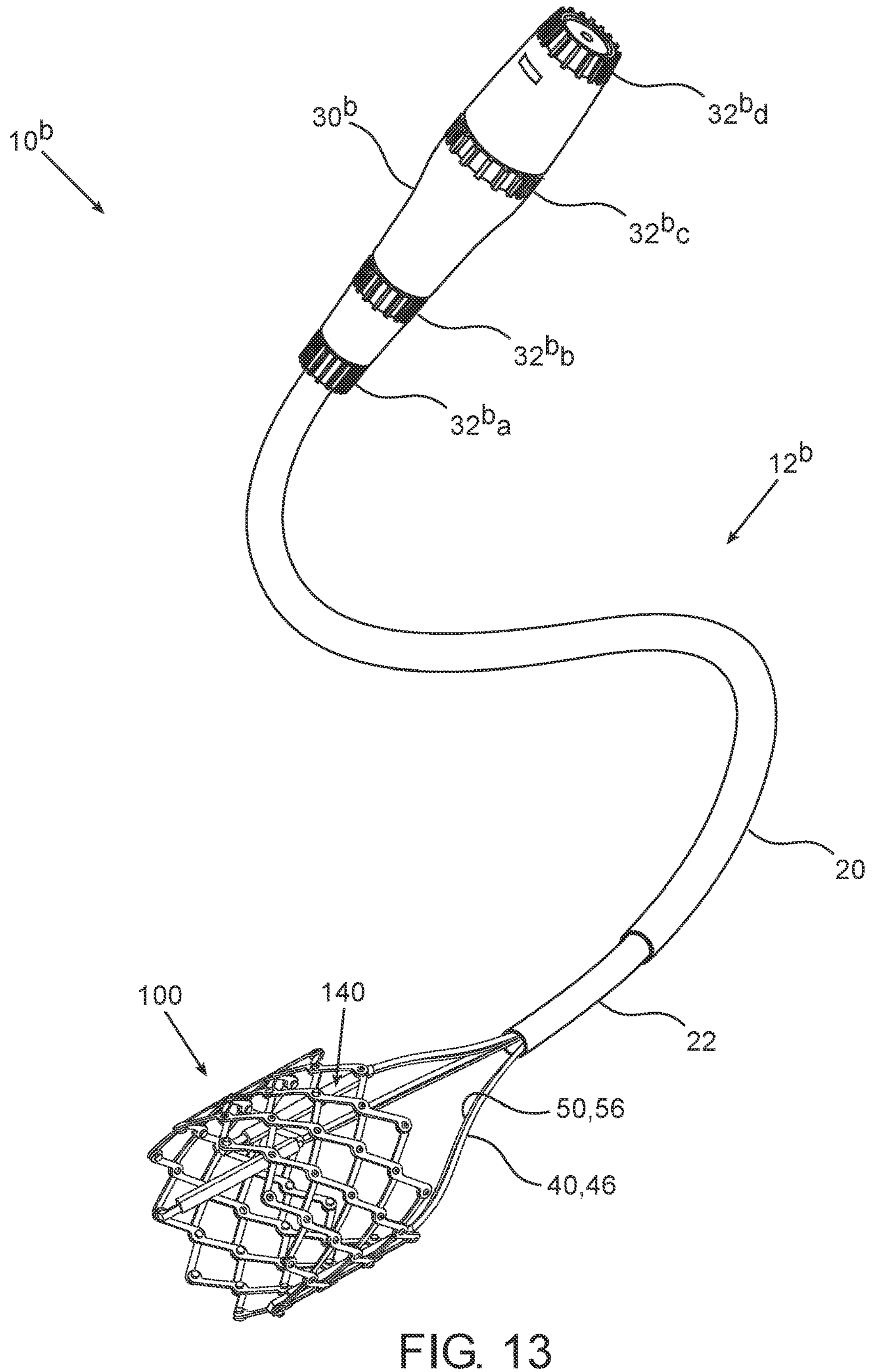
FIG. 13 shows a view in perspective of a delivery assembly comprising a delivery apparatus carrying a prosthetic valve, wherein the delivery apparatus further comprises a plurality of release assemblies, according to some embodiments.

FIG. 13 shows a view in perspective of a delivery assembly 10$^b$, which is similar to the delivery assembly 10$^a$ shown in FIG. 1, except that it further comprises a plurality of release assemblies 50. The prosthetic valve 100 can be on or releasably coupled to the delivery apparatus 12$^b$, which can include a handle 30$^b$ at a proximal end thereof, a delivery shaft 22 extending therefrom, and optionally an outer shaft 20 extending over the delivery shaft 22. The delivery apparatus 12$^b$ can further include a nosecone 26 attached to the distal end of the nosecone shaft 24, which are removed from view in FIG. 13 for clarity.

As further shown in FIG. 13, the delivery apparatus 12$^b$ further comprises a plurality of actuation assemblies 40 and a plurality of adjacent release assemblies 50, extending from the handle 30$^a$ through the delivery shaft 22. In the illustrated exemplary embodiment, the prosthetic valve 100 has three actuation assemblies 40 and three adjacent release assemblies 50, however, in other embodiments a greater or fewer number of actuation assemblies 40 and/or release assemblies 50 can be used.

Each release assembly 50 can generally include a release arm 52 (hidden from view in FIG. 13, but visible for example in FIGS. 16A-16D) releasably coupled at its distal end 54 to respective expansion and locking assembly 140 of the valve 100, and a release support sleeve 56 disposed around the corresponding release arm 52. The release arm 52 and the release support sleeve 56 can be movable longitudinally relative to each other in a telescoping manner. The release arms 52 can include, for example, wires, cables, rods, or tubes. The release support sleeves 56 can include, for example, tubes or sheaths having sufficient rigidity such that they can apply a distally directed force to the frame without bending or buckling.

The proximal ends of the delivery shaft 22, components of the actuation assemblies 40, components of the release assemblies 50, and when present—the outer shaft 20, can be coupled to the handle 30$^b$. During delivery of the prosthetic valve 100, the handle 30$^b$ can be maneuvered by an operator (e.g., a clinician or a surgeon) to axially advance or retract components of the delivery apparatus 12$^b$, such as the delivery shaft 22 and/or the outer shaft 20, through the patient's vasculature, as well as to expand or contract the prosthetic valve 100, for example by maneuvering the actuation assemblies 40 and/or the release assemblies 50, and to disconnect the prosthetic valve 100 from the delivery apparatus 12, for example—by decoupling the actuation members 42 and the release arms 52 from the expansion and locking assemblies 140 of the valve 100, in order to retract it once the prosthetic valve 100 is mounted in the implantation site.

According to some embodiments, the delivery apparatus 12$^b$ further comprises a re-compression mechanism (not shown), configured to facilitate re-compression of the prosthetic valve 100 upon expansion thereof. Further details regarding various configurations and types of prosthetic valve re-compression mechanisms can be found, for example, in International Application Publication No. WO 2020/081893, and U.S. application No. 62/928,320, both of which are incorporated herein by reference.

Figure 14:
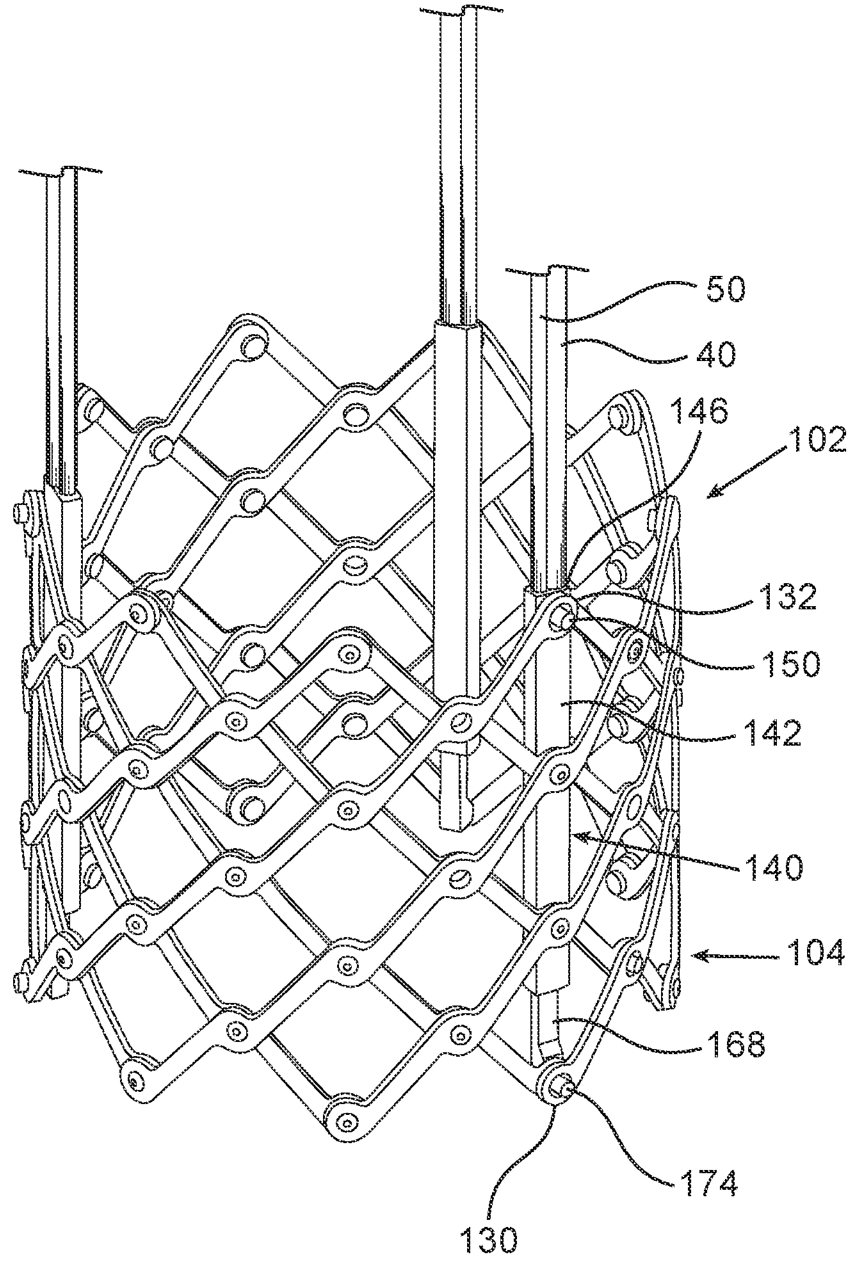
FIG. 14 shows a view in perspective of a prosthetic valve having a plurality of expansion and locking assemblies, attached to corresponding actuation assemblies and release assemblies, according to some embodiments.

FIG. 14 shows the valve 100 (without the leaflets and other components) in a radially expanded configuration, equipped with three expansion and locking assemblies 140 coupled to corresponding actuation assemblies 40 and to release assemblies 50. As shown, each expansion and locking assemblies 140 can be releasably coupled to a single actuation assembly 40, and to a single release assembly 50 adjacent the actuation assembly 40.

Figure 15A:
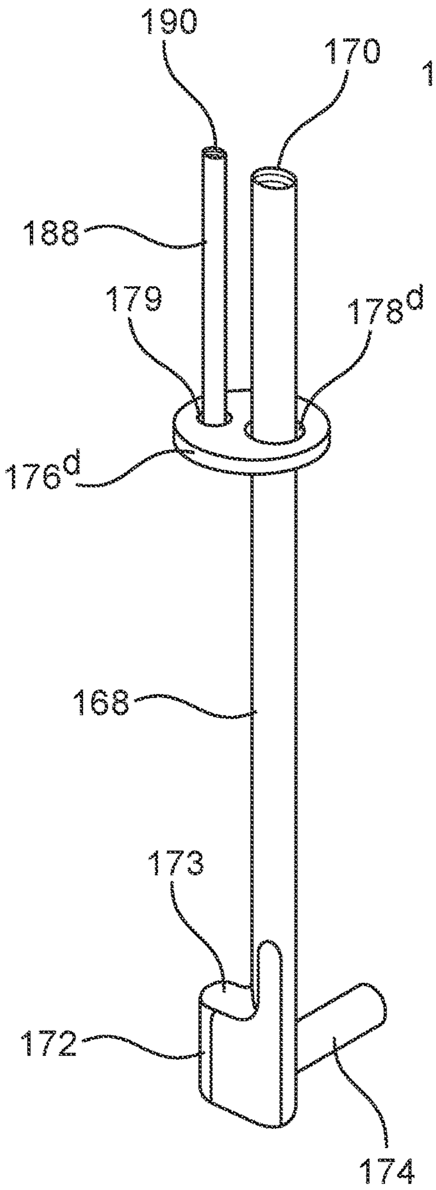
FIG. 15A shows a view in perspective of an inner member and a release member, extending through apertures of a plate, according to some embodiments.
Figure 15B:
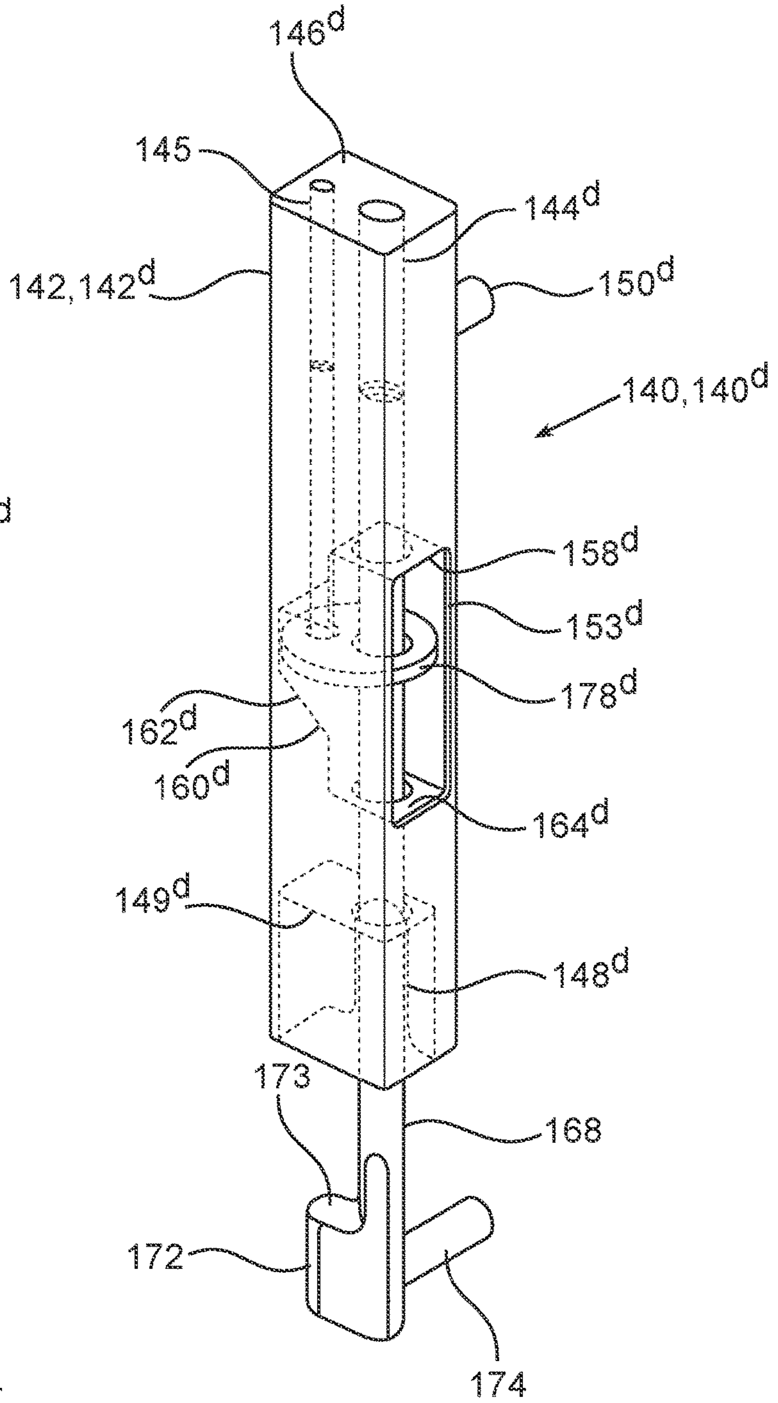
FIG. 15B shows a view in perspective of an expansion and locking assembly comprising a release member, according to some embodiments.

FIG. 15A-15B illustrate an expansion and locking assembly 140$^d$, which can be similar to any of the previous embodiments disclosed herein above for expansion and locking assemblies 140, further comprising a release member 188 at least partially extending into the expansion and locking assembly 140$^d$. Optionally, but in some embodiments preferably, the outer member 142$^d$ further comprises a release channel 145, configured to accommodate the release member 188 therein.

According to some embodiments, the plate 176$^d$ comprises a primary aperture 178$^d$ and a release aperture 179. FIG. 15A shows a view in perspective of an inner member 168 extending through the primary aperture 178$^d$, and an exemplary release member 188 extending through the release aperture 179. The release member 188 comprises a release member proximal end portion 190 and a release member distal end portion 192, terminating at a release member distal end 193 (shown, for example, in FIG. 17A). The release member 188 may be provided in the form of a rod having a uniform cross-sectional profile along its length. While an exemplary embodiment of a rod having a uniform circular cross section is illustrated, it will be clear that the cross-section can be provided with other shapes, including square, rectangular, triangular, pentagonal, hexagonal, octagonal, elliptical, star-shaped, and the like.

FIG. 15B shows both the inner member 168 and the release member 188 disposed within lumens of the outer member 142$^d$, and more specifically, extending through a primary channel 144$^d$ and a release channel 145, respectively, of the outer member 142$^d$. The outer member 142$^d$ is shown with partial transparency in FIG. 15B to reveal the underlying structures. The outer member 142$^d$ comprises an outer member proximal end 146$^d$ defining two proximal openings for the primary channel 144$^d$ and a release channel 145, and an outer member distal end portion 147$^d$ defining a distal opening for the inner member 168. As shown, the release channel 145 extends between the outer member proximal end 146$^d$ and the chamber 152$^d$, enabling the release member 188 to extend there-through, into the chamber 152$^d$.

According to some embodiments, the release member proximal end portion 190 further comprises a threaded bore, configured to receive and threadedly engage with a threaded portion of a distal end portion 54 (shown for example in FIGS. 16A-16D) of a corresponding release arm 52.

Figure 16A:
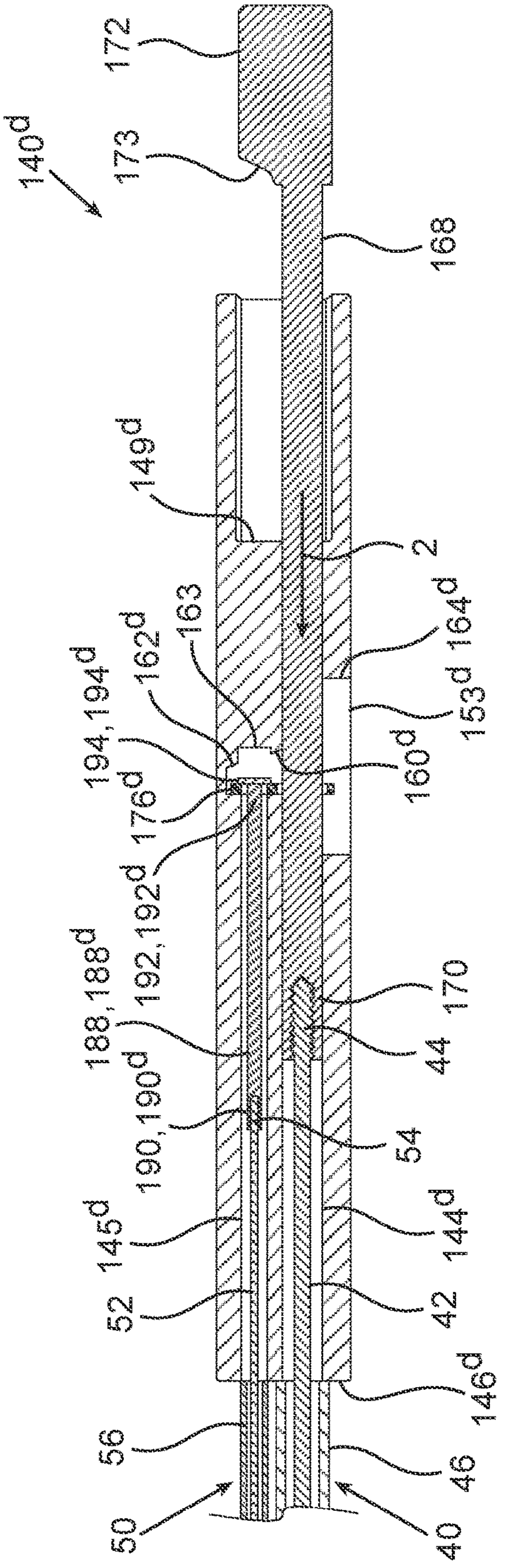
FIGS. 16A-16D show cross-sectional views of an expansion and locking assembly in different operational states thereof, according to some embodiments.

FIGS. 16A-16D show cross-sectional views in various stages of actuating the expansion and locking assembly 140$^d$ to facilitate valve expansion and lock the valve it in an expanded configuration, as well as to allow re-compression of a locked valve. FIG. 16A shows an initial state in which the actuation member distal end portion 44 is threaded into a threaded bore of the inner member proximal end portion 170, and the release arm distal end portion 54 is threaded into a threaded bore of the release member proximal end portion 190. The inner member 168 extends through the primary channel 144$^d$ and the chamber 152$^d$ of the outer member 142$^d$, such that the inner member fastener (174) is distanced from the outer member fastener (150$^d$) at a distance that may be associated with a compressed, or a partially compressed, configuration of the valve (100). In this state, the inner member 168 may extend distally from the outer member 142$^d$ such that the inner member fastener (174) is distanced distally away from the outer member distal end 147$^d$. The release member 188 extends through the release channel 145$^d$, and may partially extend into the chamber 152$^d$, wherein the release member distal end portion 192 is coupled to the plate 176.

According to some embodiments, as shown in FIGS. 16A-16D, the release arm distal end portion 54 includes external threads, configured to engage with internal threads of a proximal bore of the release member proximal end portion 190. According to alternative embodiments, a release member may include a proximal extension provided with external threads, configured to be received in and engage with internal threads of a distal bore formed within the release arm (embodiments not shown).

In the actuation state shown in FIG. 16A, the actuation member 42 may be pulled in a proximally oriented direction 2, while the actuation support sleeve 46 is held firmly against the outer member 142$^d$ so as to prevent the outflow end 103 of the frame 106 from moving relative to the actuation support sleeve 46. As such, movement of the actuation member 42 in a proximally oriented direction 2 causes movement of the inner member 168 in the same direction, thereby causing the frame 106 to foreshorten axially and expand radially. Pulling the inner member 168 in a proximally oriented direction 2 (as shown in FIG. 16A) may pull the plate 176$^d$ there-along, optionally (but not necessarily) until the plate 176$^d$ is pressed against the proximal chamber wall 158$^d$.

In some implementations, the release arm 52 may be pulled in the proximal direction 2, simultaneously with the pulling of the actuation member 42, thereby pulling the release member 188 therewith in the proximal direction 2. Alternatively, the release arm 52 may remain free or even pushed in the distal direction 4, thereby either retaining the release member 188 in an axially movable free state, or pushed distally toward the distal chamber wall 160, during actuation of the actuation assembly 40, enabling bi-directional free axial movement of the inner member 168 through the primary aperture 178, without interfering with such relative movement by the release member 188.

Figure 16B:
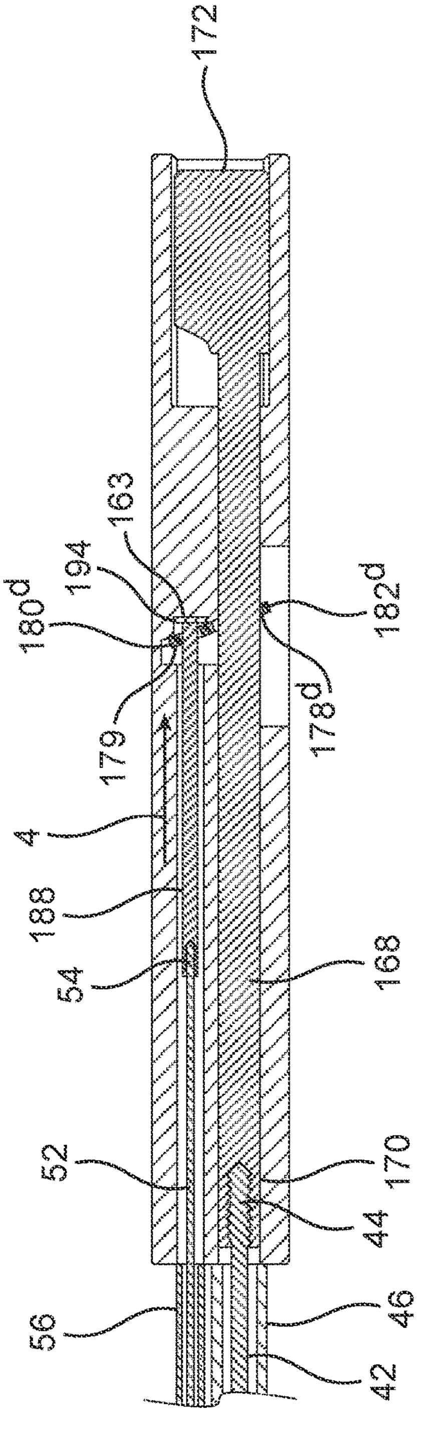

FIG. 16B shows the inner member 168 positioned at a more proximal position relative to its position within the outer member 142$^d$ shown in FIG. 16A. In the illustrated state, pulling force in the proximal direction is no longer applied to the inner member (168). When an external force (e.g., applied by the surrounding anatomy) strives to re-compress the valve 100, thereby distancing the proximal and distal junctions away from each other, the plate 176$^d$ assumes an angled locking orientation which serves to lock the expansion and locking assembly 140$^d$ and retain the valve (100) in the expanded configuration, for example by being pushed against the distal chamber wall 160$^d$.

Figure 16C:
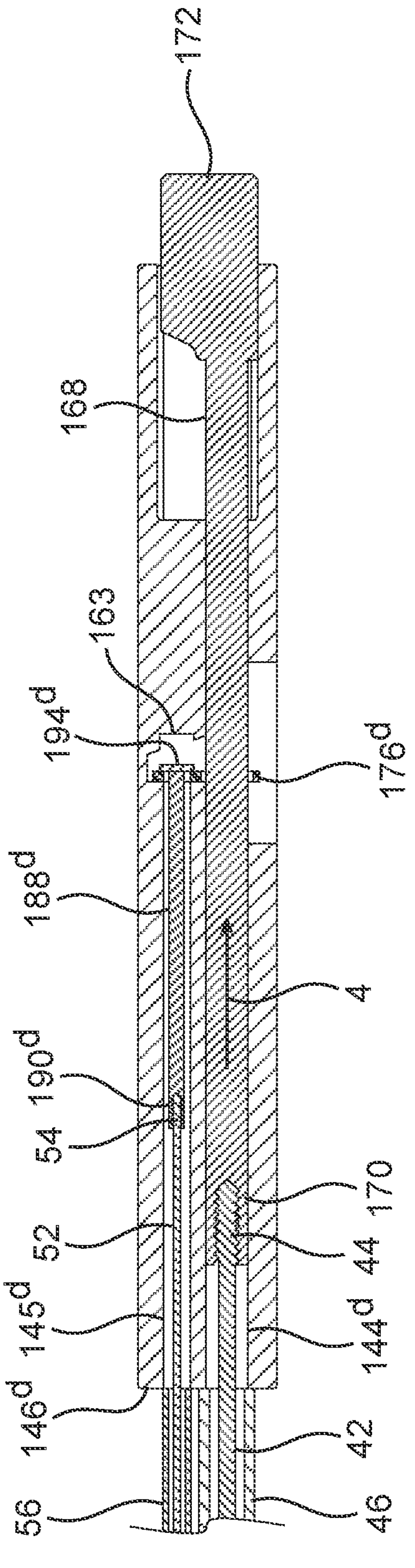
Figure 16D:
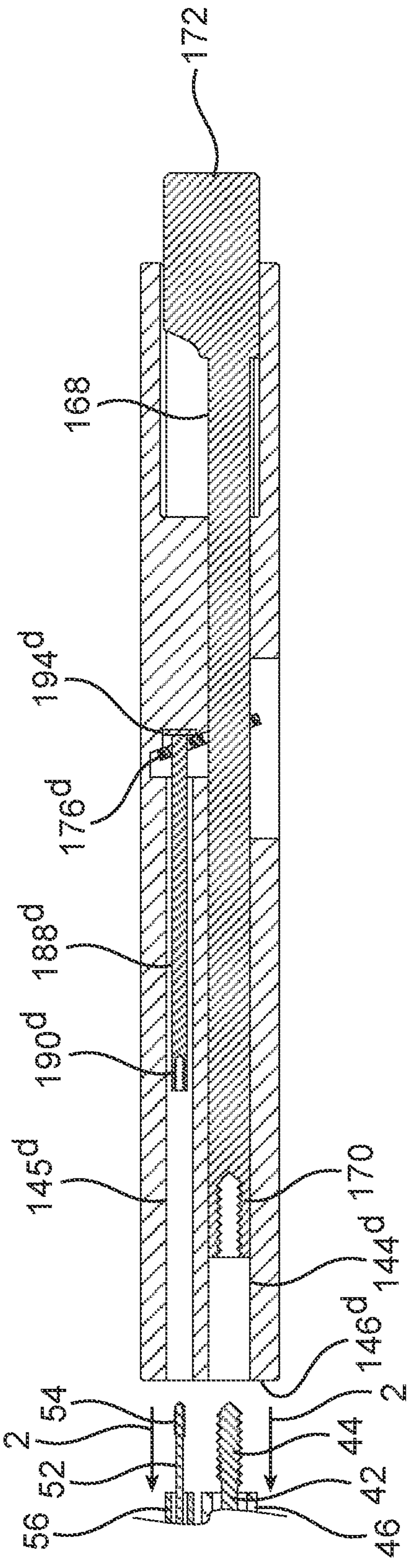
Figure 17A:
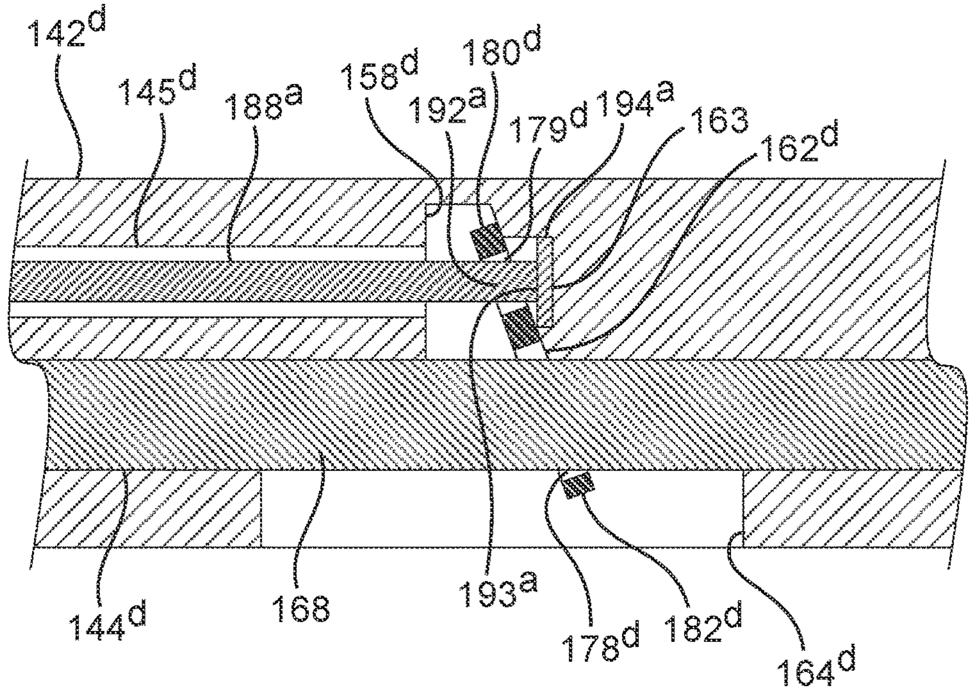
FIG. 17A shows an enlarged cross-sectional view of a portion of an expansion and locking assembly containing the chamber, corresponding to the state shown in FIG. 16B or 16D.

FIG. 17A shows an enlarged partial view of the expansion and locking assembly 140$^d$ around the chamber 152$^d$, which may correspond to the state shown in FIG. 16B. According to some embodiments, the plate 176$^d$ comprises a release aperture 179, disposed within the first zone 154, through which the release member 188$^a$, and more particularly, its distal end portion 192$^a$, extends. The release member distal end 193$^a$ may be attached to a retention feature 194, extending radially outward from the release member distal end 193$^a$. In the exemplary embodiment illustrated in FIGS. 16A-17A, the retention feature 194$^a$ is in the form of a disc or plate, attached to the release member distal end 193$^a$. In alternative implementations, the retention feature 194 may be an attachable or integral flange extending radially outward from the release member distal end 193.

The diameter of the release member distal end portion 192$^a$ is smaller than the diameter of the release aperture 179, allowing it to extend therethrough, while the diameter of the retention feature 194$^a$, positioned distal to the release aperture 179, is greater than the diameter of the release aperture 179.

As shown in FIGS. 16B and 17A, when the plate 176$^d$ is in the angled locking orientation, the release member 188 is free to be moved axially in any direction, enabling the plate first side 180$^d$ to push the retention feature 194$^a$, and the release member 188$^a$ therewith, in the distal direction 4, if the plate 176$^d$ is pushed, for example, toward the distal chamber wall 160$^d$. In this manner, the release member 188$^a$ does not interfere with the transition of the plate 176$^d$ from the non-locking orientation to the angled locking orientation, and the optional translation of the plate 176$^d$ toward the distal chamber wall 160$^d$.

While FIG. 16B illustrates the expansion and locking assembly 140$^d$ retained in a locked state, preventing re-compression of the prosthetic valve (100) by preventing advancement of the inner member 168 in the distal direction 4, it may be desirable in some instances to allow valve re-expansion for the purpose of valve repositioning or re-crossing, for example. In such cases, the inner member 168 should be allowed to translate in the distal direction 4, which is accomplished by actuation of a release assembly 50. FIG. 16C shows a state in which the release assembly 50 is actuated so as to allow valve re-compression.

The release support sleeve 56 surrounds the release arm 52 and may be connected to the handle 30. The release support sleeve 56 and the outer member 142$^d$ are sized such that the distal lip of the release support sleeve 56 can abut or engage the outer member proximal end 146$^d$, such that the outer member 142$^d$ is prevented from moving proximally beyond the release support sleeve 56.

In order to re-compress the frame 106, and therefore the valve 100, the release support sleeve 56 can be held firmly against the outer member 142$^d$, while the release arm 52 is pulled in a proximally oriented direction 2. Since the release support sleeve 56 is being held against the outer member 142$^d$, which is connected to an outflow apex (132), the outflow end (103) of the frame (106) is prevented from moving relative to the release support sleeve 56. As such, movement of the release arm 52 in a proximally oriented direction 2 can cause movement of the release member 188$^a$ in the same direction.

As Further shown in FIG. 16C, the retention feature 194$^a$, which is attached to the release member distal end 193$^a$, positioned distal to the plate 176$^d$, is consequently pulled in a proximal direction 2 as well, pressing the proximal surface of the retention feature 194$^a$ against the distal surface of the plate 176$^d$ around the release aperture 179, thereby pulling the plate first side 180$^d$ in the same proximal direction, resulting in transitioning of the plate 176$^d$ from an angled locking orientation to a non-locking orientation, optionally pressing the 176$^d$ against the proximal chamber wall 160$^d$ to assume a substantially orthogonal orientation relative to the longitudinal axis of the inner member 168.

Once the plate 176$^d$ assumes the non-locking orientation, the inner member 168 is free to axially move through the primary aperture 178$^d$ in any direction. In some embodiments, to facilitate valve re-compression in the state shown in FIG. 16C, the actuation member 42 may be pushed in a distally oriented direction 4, pushing the inner member 168 therewith, thereby causing radial re-compression of the frame (106). FIG. 16C shows the inner member proximal end portion 170 positioned distal to its position in FIG. 16B, as a result of simultaneously pushing of the actuation member 42 in a distal direction 4, while pulling the release arm 52 in the proximal direction 2.

In alternative embodiments, valve re-compression is not facilitated by directly applying a pushing force to the actuation members 42, but rather by utilization of a re-compression mechanism of the type disclosed, for example, in International Application Publication No. WO 2020/081893, and U.S. application No. 62/928,320, which basically includes a flexible loop circumscribing the valve 100, wherein loop contraction, for example operable tensioning the loop via handle 30, facilitates valve compression therewith, during which the inner member 168 may passively advance in the distal direction 4 as shown in FIG. 16C.

Once the valve 100 is re-compressed, the release assembly 50 can be either released by not applying any pulling forces thereto, or alternatively by pushing it in a distal direction 4, for example toward and/or into the niche 163 dimensioned to accommodate the retention feature 194$^{a}$, allowing the plate 176$^{d}$ to re-assume the angled locking orientation as shown in FIG. 16B. The valve 100 can be repositioned and re-expanded in the new position, by pulling the actuation member 42 in the proximal direction 2 as described in relation to FIG. 16A above. Thus, numerous cycles of valve expansion and compression can be executed by transitioning between the states shown in FIGS. 16A, 16B and/or 16C described above.

As shown in FIG. 16D, once the valve 100 assumes a final desired expansion diameter at the desired position within the site of implantation, the actuation member 42 and the release arm 52 may be rotated about their respective axes to unscrew them from the inner member 168 and the release member 188$^{a}$, respectively, enabling the actuation assemblies 40 and the release assemblies 50 to be pulled away and retracted, together with the delivery apparatus 12$^{b}$, from the patient's body, leaving the prosthetic valve (100) implanted in the patient. In some embodiments, the actuation member 42 and the release arm 52 may be rotated simultaneously, while in other embodiments, one may be rotated and release first, followed by rotation and releasing of the other.

FIG. 16A-17A illustrate a specific arrangement of a release member 188 coupled to a plate first side 180, configured to transition the plate 176 to the non-locking orientation by pulling the plate first side 180 in the proximal direction. FIG. 17B shows another embodiment of a release member 188 coupled to a plate second side 182, instead of to the plate first side 180. The outer member 142$^{f}$ shown in FIG. 17B can be similar to the outer member 142$^{d}$ (shown, for example, in FIG. 17A), wherein the difference lies in the position of the release channel 145$^{f}$ with respect to the primary channel 144$^{f}$, configured to enable the release member 188$_{c}$, to extend into the second zone 156 of the chamber 152$^{f}$. The plate 176$^{f}$ shown in FIG. 17B can be similar to the plate 176$^{d}$ (shown, for example, in FIG. 17A), except that while the release aperture 179$^{d}$ is disposed within the plate first side 180$^{d}$, the release aperture 179$^{f}$ is disposed within the plate second side 182$^{f}$.

Figure 17B:
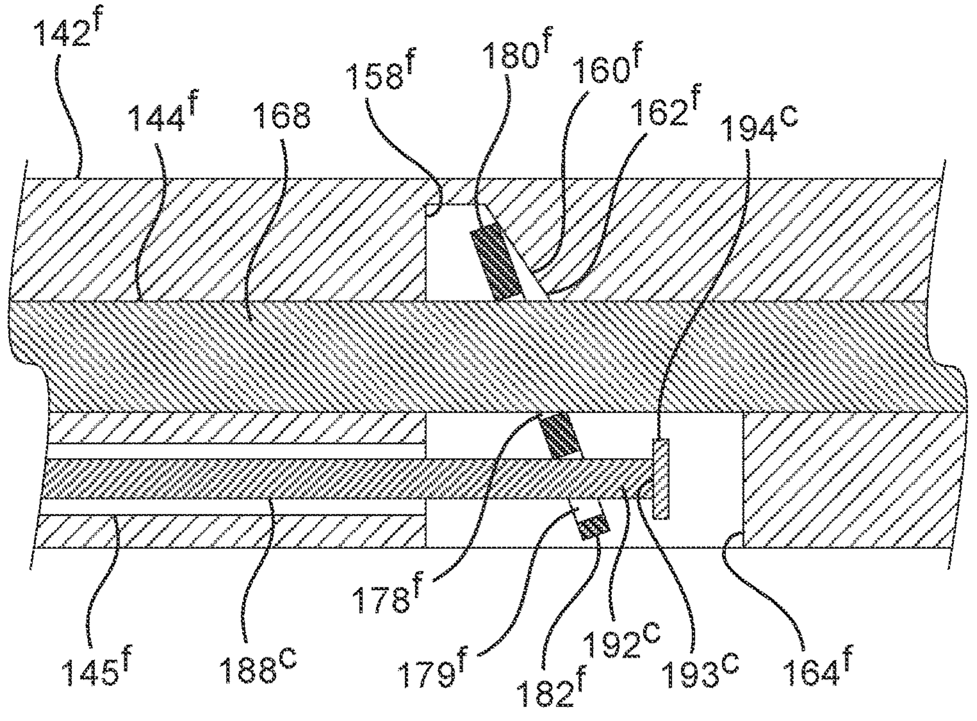
FIG. 17B shows an enlarged cross-sectional view of a portion of another embodiments of an expansion and locking assembly.

The release member 188$^{c}$ can be identical to the release member 188$^{a}$, comprising a release member proximal end portion (190$^{c}$) and a release member distal end portion 192$^{c}$, terminating at a release member distal end 193$^{c}$ which is attached to a retention feature 194$^{c}$. The retention feature 194$^{c}$, which may be identical to retention feature 194$^{a}$, is shown in FIG. 17B to be positioned distal to the release aperture 179$^{f}$, and the release member 188$^{c}$ can be releasably attached to a release assembly 50, and operable to pull the re-orient the plate 176$^{f}$ to the non-locking orientation, in the same manner described for release member 188$^{a}$ and plate 176$^{d}$ herein above and throughout FIG. 16A-17A, mutatis mutandis.

According to some embodiments, the handle 30$^{b}$ can comprise control mechanisms which may include steerable or rotatable knobs 32$^{b}$, levers, buttons and such, which in some implementation may be manually controllable by an operator to produce axial and/or rotatable movement of different components of the delivery apparatus 12$^{b}$. For example, the embodiment of handle 30$^{b}$ illustrated in FIG. 13 comprises first, second, third and fourth knobs 32$^{b}$*a*, 32$^{b}$*b*, 32$^{b}$*c* and 32$^{b}$*d*, respectively.

Knob 32$^{b}$*a*, shown in FIG. 13, can be a rotatable knob configured to produce bi-directional axial translation of the outer shaft 20 relative to the prosthetic valve 100 in the distal and/or proximal directions, for example to retract the outer shaft 20 and expose the prosthetic valve 100 once it is positioned at or adjacent the desired site of implantation within the patient's body. For example, rotation of the knob 32$^{b}$*a* in a first direction (e.g., clockwise) can retract the outer shaft 20 proximally relative to the prosthetic valve 100, and rotation of the knob 32$^{b}$*a* in a second direction (e.g., counterclockwise) can advance the outer shaft 20 distally.

Knob 32$^{b}$*b*, shown in FIG. 13, can be a rotatable knob configured to steer the outer shaft 20 as it advances through the curvatures of the patient's vasculature. Particularly, the handle 30$^{b}$ may comprise, in some embodiments, a steering mechanism, which may include at least one pull wire (not shown) attached at its distal end to the outer shaft 20 (or other shafts of the delivery apparatus 12$^{b}$), such that rotation of the knob 32$^{b}$*b* may vary the tension of the pull wire, which is effective to vary the curvature of the outer shaft 20.

Knob 32$^{b}$*d*, shown in FIG. 13, can be a rotatable knob configured to produce radial expansion and/or contraction of the prosthetic valve 100. For example, rotation of the knob 32$^{b}$*d* can move the actuation member 42 and the actuation support sleeve 46 axially relative to one another, and optionally also move the release arm 52 and the release support sleeve 56 axially relative to one another. Rotation of the knob 32$^{b}$*d* in a first direction (e.g., clockwise) can radially expand the prosthetic valve 100, for example by pulling the actuation members 42 in the proximal direction 2, and rotation of the knob 32$^{b}$*d* in a second direction (e.g., counterclockwise) can re-compress the prosthetic valve 100, for example by pulling the release arms 52 to allow such re-compression.

In alternative embodiments, two or more separate knobs may be configured to facilitate expansion and compression of the valve 100. For example, one knob may control the actuation assemblies 40, while another knob may control actuation of the release assemblies 50 (embodiments not shown).

Knob 32$^{b}$*c*, shown in FIG. 13, can be a rotatable knob configured to release the prosthetic valve 100 from the delivery apparatus 12$^{b}$. For example, rotation of the knob 32$^{b}$*c* in a first direction (e.g., clockwise) can disengage both the actuation assemblies 40 and the release assemblies 50 from the expansion and locking assemblies 140$^{d}$ of the prosthetic valve 100. In alternative embodiments, two or more separate knobs may be configured to facilitate release the prosthetic valve 100 from the delivery apparatus 12$^{b}$. For example, one knob may disengage the actuation assemblies 40 from the expansion and locking assemblies 140$^{d}$, while another knob may disengage the release assemblies 50 from the expansion and locking assemblies 140$^{d}$ (embodiments not shown).

Any of the knobs 32$^{b}a$, 32$^{b}b$, 32$^{b}c$ and 32$^{b}d$ may be implemented, in alternative embodiments, as other types of buttons, levers, knobs and the like, such as push/pull knobs which may be actuated by sliding or moving the knobs axially.

FIGS. 18A-18D show cross-sectional views in various stages of actuating the expansion and locking assembly 140$^{e}$, which are similar to the views and stages illustrated and described in conjunction with FIGS. 16A-16D above, except that the release member 188$^{b}$ is implemented in a different manner than that of release member 188$^{a}$, as will be elaborated in greater detail hereinbelow.

Figure 18A:
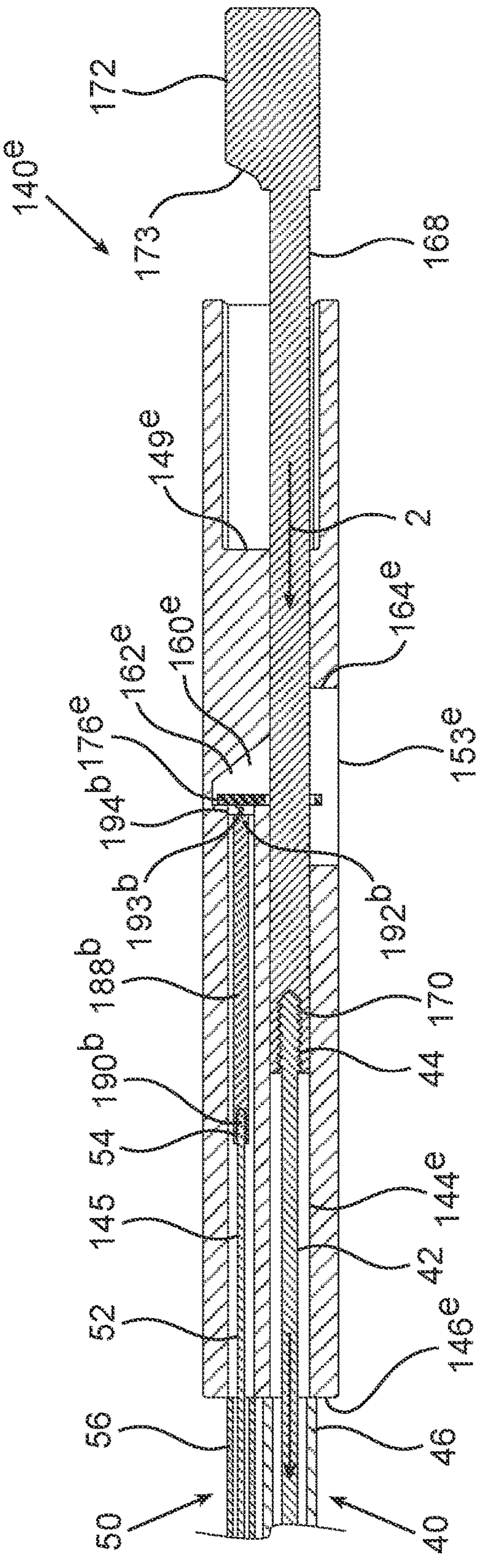
FIGS. 18A-18D show cross-sectional view of an expansion and locking assembly in different operational states thereof, according to other embodiments.

FIG. 18A shows an initial state in which the actuation member distal end portion 44 is threaded into a threaded bore of the inner member proximal end portion 170, and the release arm distal end portion 54 is threaded into a threaded bore of the release member proximal end portion 190$^{b}$. The inner member 168 extends through the primary channel 144$^{e}$ and the chamber 152$^{e}$ of the outer member 142$^{e}$, such that the inner member fastener (174) is distanced from the outer member fastener (150$^{e}$) at a distance that may be associated with a compressed, or a partially compressed, configuration of the valve (100). In this state, the inner member 168 may extend distally from the outer member 142$^{e}$ such that the inner member fastener 174 is distanced distally away from the outer member distal end 147$^{e}$. The release member 188$^{a}$ extends through the release channel 145$^{e}$, and may partially extend into the chamber 152$^{d}$, wherein the release member distal end portion 192$^{b}$ is coupled to the plate 176$^{e}$.

In the actuation state shown in FIG. 18A, the actuation member 42 may be pulled in a proximally oriented direction 2, while the actuation support sleeve 46 is held firmly against the outer member 142$^{e}$ so as to prevent the outflow end 103 of the frame 106 from moving relative to the actuation support sleeve 46. As such, movement of the actuation member 42 in a proximally oriented direction 2 causes movement of the inner member 168 in the same direction, thereby causing the frame 106 to foreshorten axially and expand radially. Pulling the inner member 168 in a proximally oriented direction 2 (as shown in FIG. 18A) may pull the plate 176$^{e}$ there-along, optionally (but not necessarily) until the plate 176$^{e}$ is pressed against the proximal chamber wall 158$^{e}$.

In some embodiments, the release arm 52 may be pulled in the proximal direction 2, simultaneously with the pulling of the actuation member 42, thereby pulling the release member 188$^{b}$ therewith in the proximal direction 2. Alternatively, the release arm 52 may remain free or even pushed in the distal direction 4, thereby either retaining the release member 188$^{b}$ in an axially movable free state, or pushed distally toward the distal chamber wall 160$^{e}$, respectively, during actuation of the actuation assembly 40, enabling free movement of the inner member 168 through the primary aperture 178$^{e}$, without hindering such relative movement by the release member 188$^{b}$.

Figure 18B:
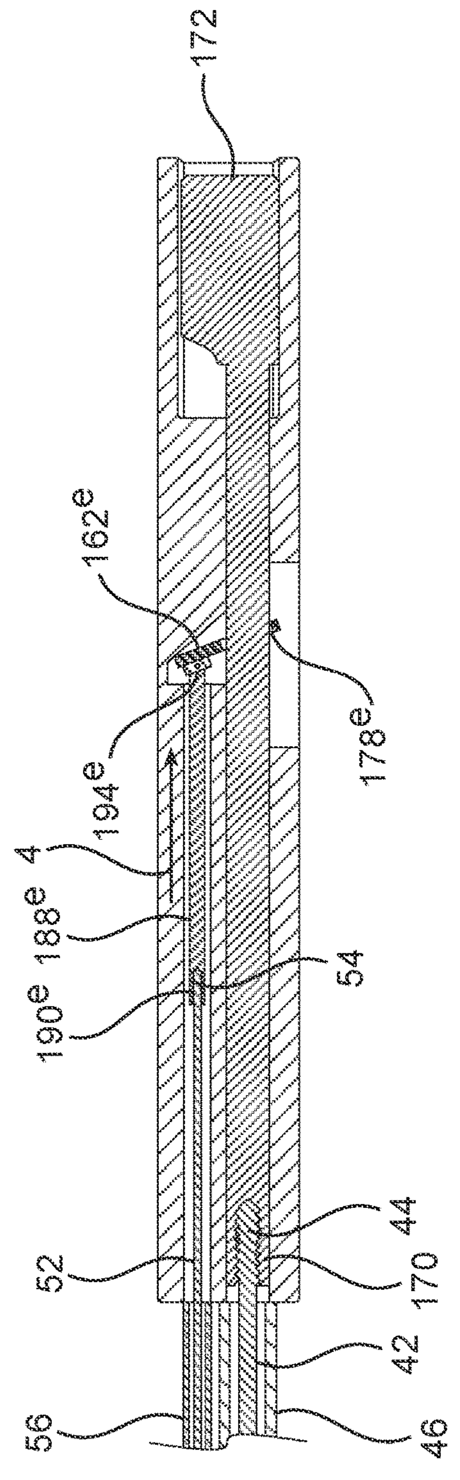

FIG. 18B shows the inner member 168 positioned at a more proximal position relative to its position within the outer member 142$^{e}$ shown in FIG. 18A. In the illustrated state, pulling force in the proximal direction is no longer applied to the inner member (168). When an external force (e.g., applied by the surrounding anatomy) strives to re-compress the valve 100, thereby distancing the proximal and distal junctions away from each other, the plate 176$^{e}$ assumes an angled locking orientation which serves to lock the expansion and locking assembly 140$^{e}$ and retain the valve (100) in the expanded configuration, for example by being pushed against the distal chamber wall 160$^{e}$.

Figure 18C:
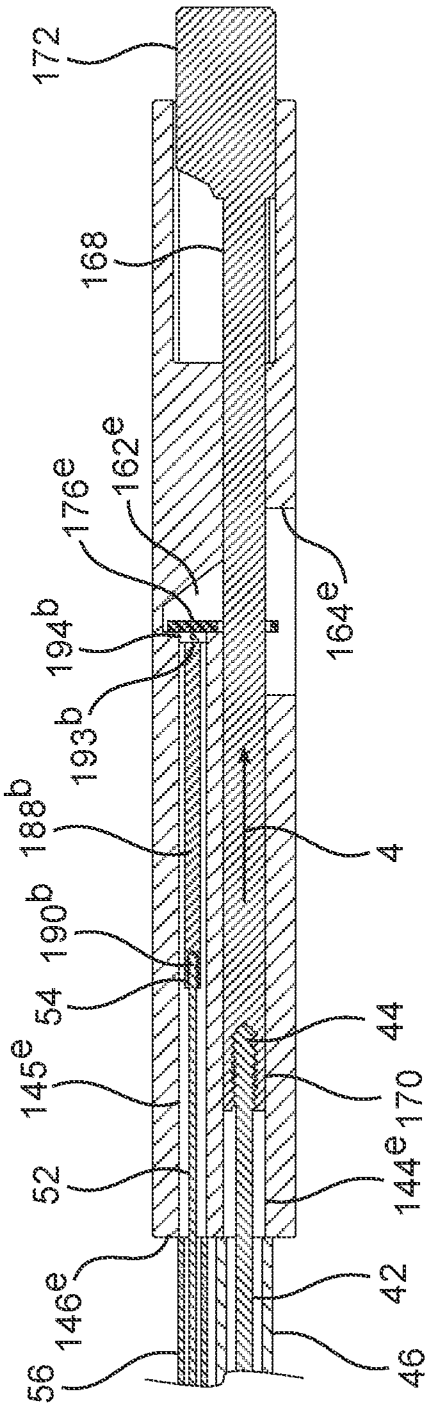
Figure 18D:
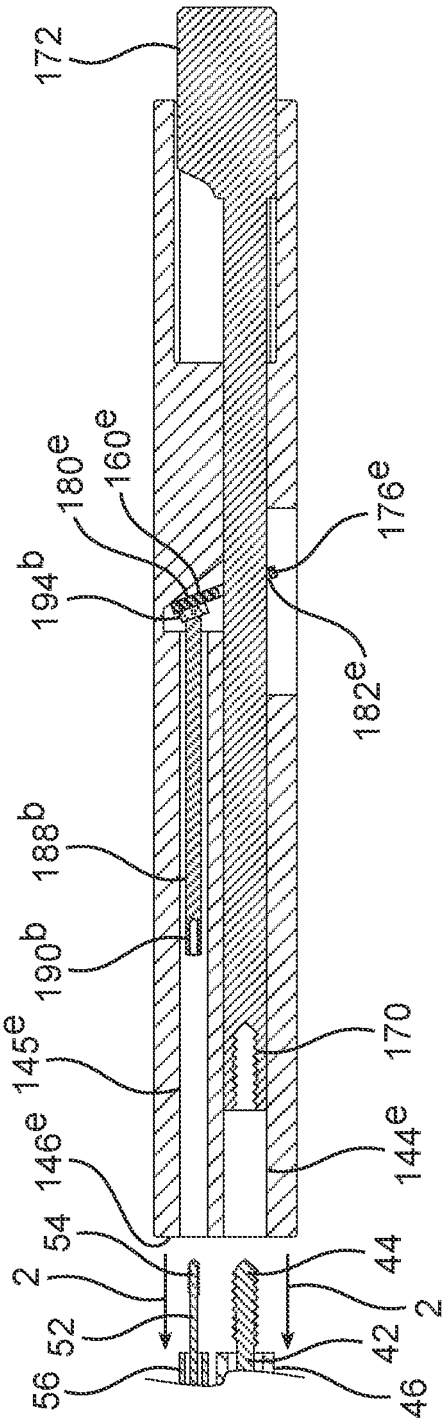
Figure 19A:
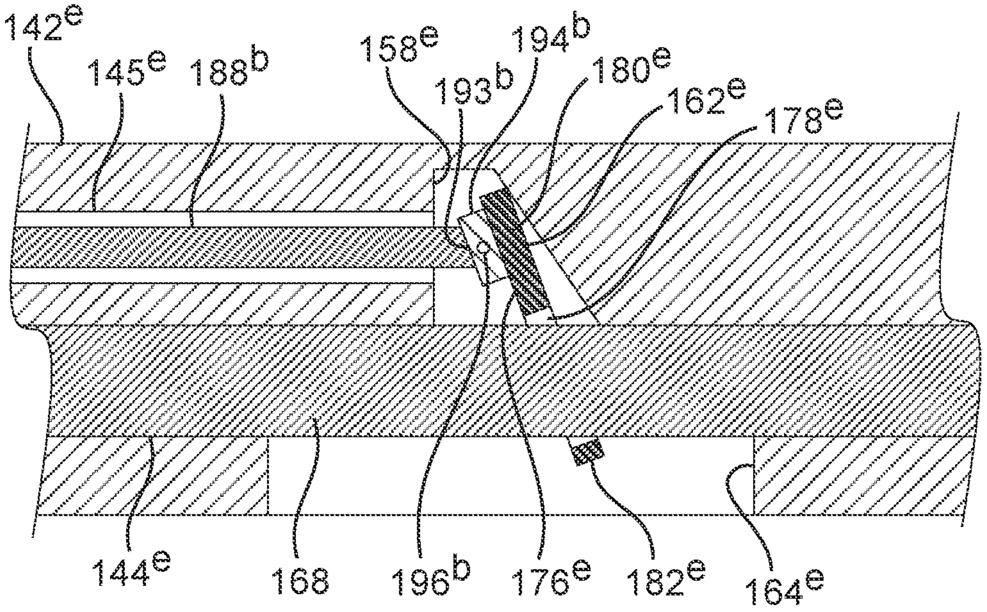
FIG. 19A shows an enlarged cross-sectional view of a portion of an expansion and locking assembly containing the chamber, corresponding to the state shown in FIG. 18B or 18D.
Figure 19B:
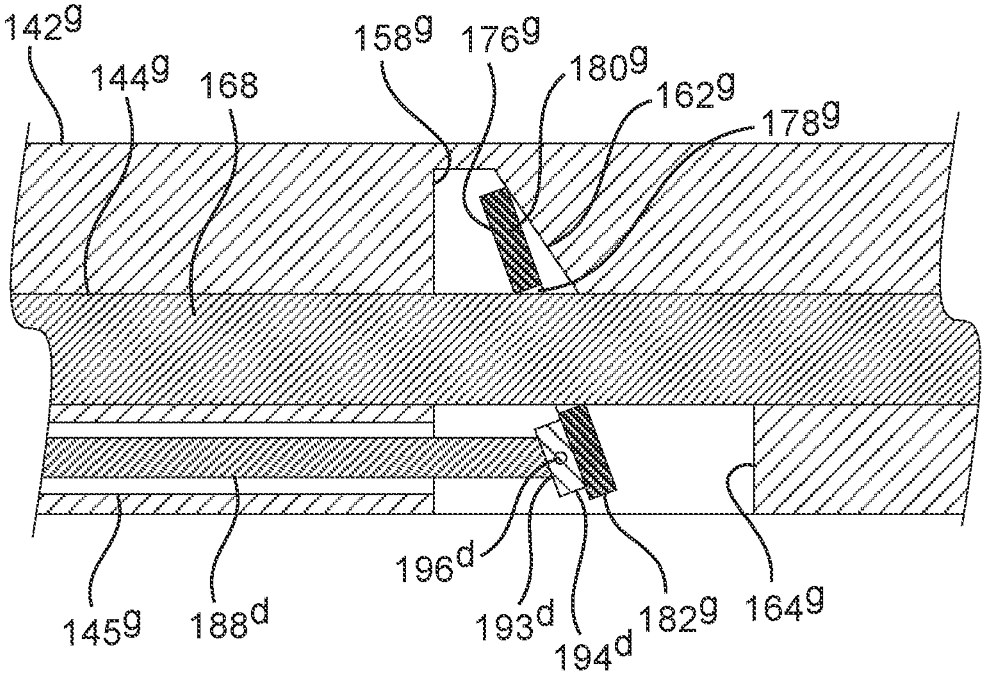
FIG. 19B shows an enlarged cross-sectional view of a portion of another embodiment of an expansion and locking assembly.

FIG. 19A shows an enlarged partial view of the expansion and locking assembly 140$^{e}$ around the chamber 152$^{e}$, which may correspond to the state shown in FIG. 18B. Unlike the embodiments illustrated in FIGS. 16A-17A, the plate 176$^{e}$ shown in FIGS. 18A-19A does not include release aperture (179). As shown, a retention feature 194$^{b}$ may be pivotably attached to the release member distal end 193$^{b}$ via release member distal hinge 196$^{b}$, allowing the retention feature 194$^{b}$ to pivot about the axis defined by the hinge 196$^{b}$ (an axis which may be orthogonal to the cross-sectional plane shown in FIG. 16A-17A). The retention feature 194$^{b}$ may be rigidly attached to the plate 176$^{e}$. For example, the distal surface of the retention feature 194$^{b}$ may be affixed to the proximal surface of the plate first side 180$^{e}$. Since the retention feature 194$^{b}$ is not positioned distal to the plate 176$^{e}$, the distal chamber wall 160 may be provided without a niche (163).

In alternative embodiments, the release member distal end portion 192 is directly attached to the plate 176 in a pivotable manner, allowing the plate 176 to pivot about a release member distal hinge 196, without the use of an intermediate retention feature (194).

FIG. 18C shows a state in which the release assembly 50 is actuated so as to allow valve re-expansion. The release support sleeve 56 surrounds the release arm 52 and may be connected to the handle 30. The release support sleeve 56 and the outer member 142$^{d}$ are sized such that the distal lip of the release support sleeve 56 can abut or engage the outer member proximal end 146$^{e}$, such that the outer member 142$^{e}$ is prevented from moving proximally beyond the release support sleeve 56.

In order to re-compress the frame 106, and therefore the valve 100, the release support sleeve 56 can be held firmly against the outer member 142$^{e}$, while the release arm 52 is pulled in a proximally oriented direction 2. Since the release support sleeve 56 is being held against the outer member 142$^{e}$, which is connected to an outflow apex (132), the outflow end (103) of the frame (106) is prevented from moving relative to the release support sleeve 56. As such, movement of the release arm 52 in a proximally oriented direction 2 can cause movement of the release member 188$^{b}$ in the same direction.

As Further shown in FIG. 18C, the retention feature 194$^{b}$, which is pivotably attached to the release member distal end 193$^{b}$ and rigidly attached to the plate 176$^{d}$, moves along with the release member 188$^{b}$ and pulls the plate first side 180$^{e}$ in the same proximal direction, resulting in transitioning of the plate 176$^{e}$ from an angled locked orientation to a non-locking orientation, potentially pressing the 176$^{e}$ against the proximal chamber wall 160$^{e}$ to assume a substantially orthogonal orientation relative to the longitudinal axis of the inner member 168.

Once the plate 176$^{e}$ assumes the non-locking orientation, the inner member 168 is free to axially move through the primary aperture 178$^{e}$ in any direction. In some embodiments, to facilitate valve re-compression in the state shown in FIG. 18C, the actuation member 42 may be pushed in a distally oriented direction 4, pushing the inner member 168 therewith, thereby causing radial re-compression of the frame 106. FIG. 18C shows the inner member proximal end portion 170 positioned distal to its position in FIG. 18B, as a result of simultaneous pushing of the actuation member 42 in a distal direction 4, while pulling the release arm 52 in the proximal direction 2.

In alternative embodiments, valve re-compression is not facilitated by directly applying a pushing force on the actuation members 42, but rather by utilization of a re-compression mechanism of the type disclosed, for example, in International Application Publication No. WO 2020/081893, and U.S. application No. 62/928,320, which basically includes a loop circumscribing the valve (100), wherein loop tensioning or contraction, for example operable via handle (30), facilitates valve contraction there-along, during which the inner member 168 may passively translate in the distal direction 4 as shown in FIG. 18C.

Once the valve 100 is re-compressed, the release assembly 50 can be either released by not applying any pulling forces thereto, or alternatively by pushing it in a distal direction 4, allowing the plate 176$^e$ to re-assume the angled locking orientation as shown in FIG. 18B. The valve (100) can be repositioned and re-expanded in the new position, by pulling the actuation member 42 in the proximal direction 2 as described in relation to FIG. 18A. Thus, numerous cycles of valve expansion and compression can be executed by transitioning between the states shown in FIGS. 18A, 18B and/or 18C described above.

As shown in FIG. 18D, once the valve 100 assumes a final desired expansion diameter at the proper position within the site of implantation, the actuation member 42 and the release arm 52 may be rotated about their respective axes to unscrew them from the inner member 168 and the release member 188$^b$, respectively, enabling the actuation assemblies 40 and the release assemblies 50 to be pulled away and retracted, together with the delivery apparatus 12$^b$, from the patient's body, leaving the prosthetic valve 100 implanted in the patient. In some embodiments, the actuation member 42 and the release arm 52 may be rotated may be rotated simultaneously, while in other embodiments, one may be rotated and release first, followed by rotation and releasing of the other.

FIG. 18A-19A illustrate a specific arrangement of a release member 188 coupled to a plate first side 180, configured to transition the plate 176 to the non-locking orientation by pulling the plate first side 180 in the proximal direction, in a similar manner to that shown in FIGS. 16A-17A. FIG. 19B shows an embodiment of a release member 188 coupled to a plate second side 182, instead of to the plate first side 180, in a manner similar to that described herein above with respect to FIG. 17B. The outer member 142$^g$ shown in FIG. 19B can be similar to the outer member 142$^e$ (shown, for example, in FIG. 19A), wherein the difference lies in the position of the release channel 145$^g$ with respect to the primary channel 144$^g$, configured to enable the release member 188$^d$ to extend into the second zone 156 of the chamber 152$^g$. The plate 176$^g$ shown in FIG. 19B can be similar to the plate 176$^e$ (shown, for example, in FIG. 19A), except that while the release aperture 179$^e$ is disposed within the plate first side 180$^e$, the release aperture 179$^g$ is disposed within the plate second side 182$^g$.

The release member 188$^d$ can be identical to the release member 188$^b$, comprising a release member proximal end portion (190$^d$) and a release member distal end portion 192$^d$, terminating at a release member distal end 193$^d$. The retention feature 194$^d$, which may be identical to retention feature 194$^b$, may be pivotably attached to the release member distal end 193$^d$ via release member distal hinge 196$^d$, allowing the retention feature 194$^d$ to pivot about the axis defined by the hinge 196$^d$ (an axis which may be orthogonal to the cross-sectional plane shown in FIG. 18A-17). The retention feature 194$^d$ may be rigidly attached to the plate 176$^g$. For example, the distal surface of the retention feature 194$^d$ may be affixed to the proximal surface of the plate second side 180$^g$.

The release member 188$^d$ can be releasably attached to a release assembly 50, and operable to pull the re-orient the plate 176$^g$ to the non-locking orientation, in the same manner described for release member 188$^b$ and plate 176$^e$ herein above and throughout FIG. 18A-19A, mutatis mutandis.

While a threaded engagement is described throughout the current disclosure, serving as an optional reversible-attachment mechanism between the actuation assemblies 40 and the inner members 168, or between the release assemblies 50 and the release members 188, it is to be understood that in alternative implementations, other reversible attachment mechanisms may be utilized, configured to enable the inner member 168 and/or the release members 188 (when present) to be pulled or pushed by the actuation assemblies 40 and/or the release assemblies 50, respectively, while enabling disconnection there-between in any suitable manner, potentially controllable by the handle 30, so as to allow retraction of the delivery apparatus 12 from the patient's body at the end of the implantation procedure.

Figure 20A:
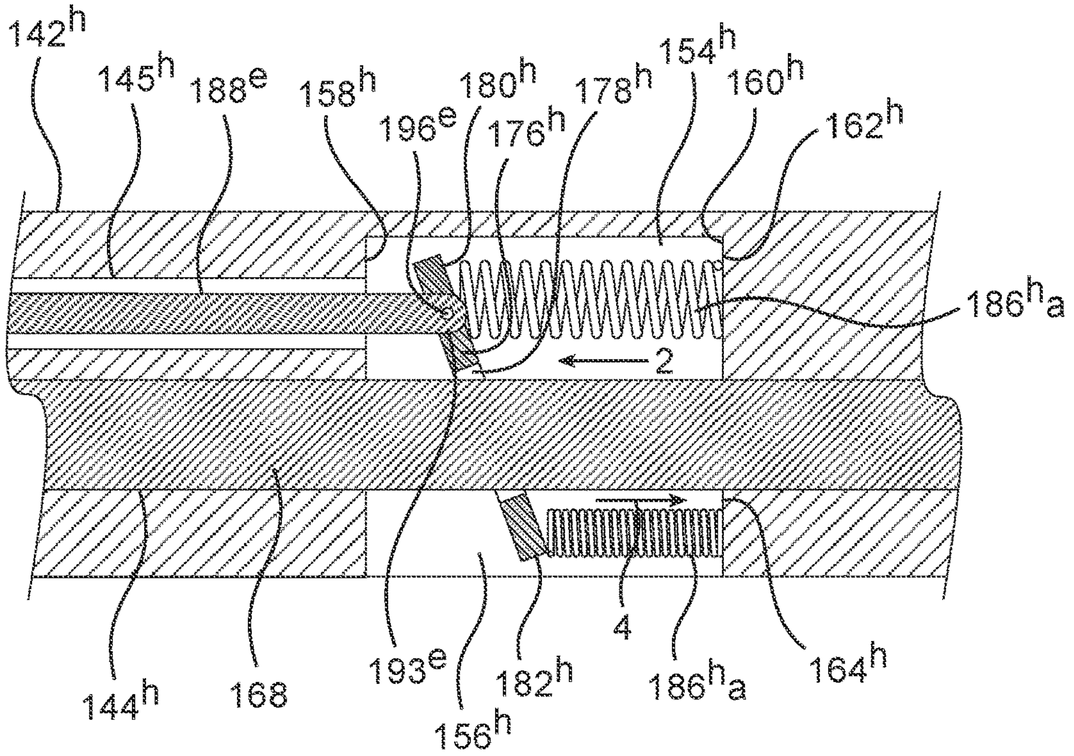
FIG. 20A shows an enlarged cross-sectional view of an expansion and locking assembly, comprising two springs residing within the chamber, in a free state of the springs, according to some embodiments.
Figure 20B:
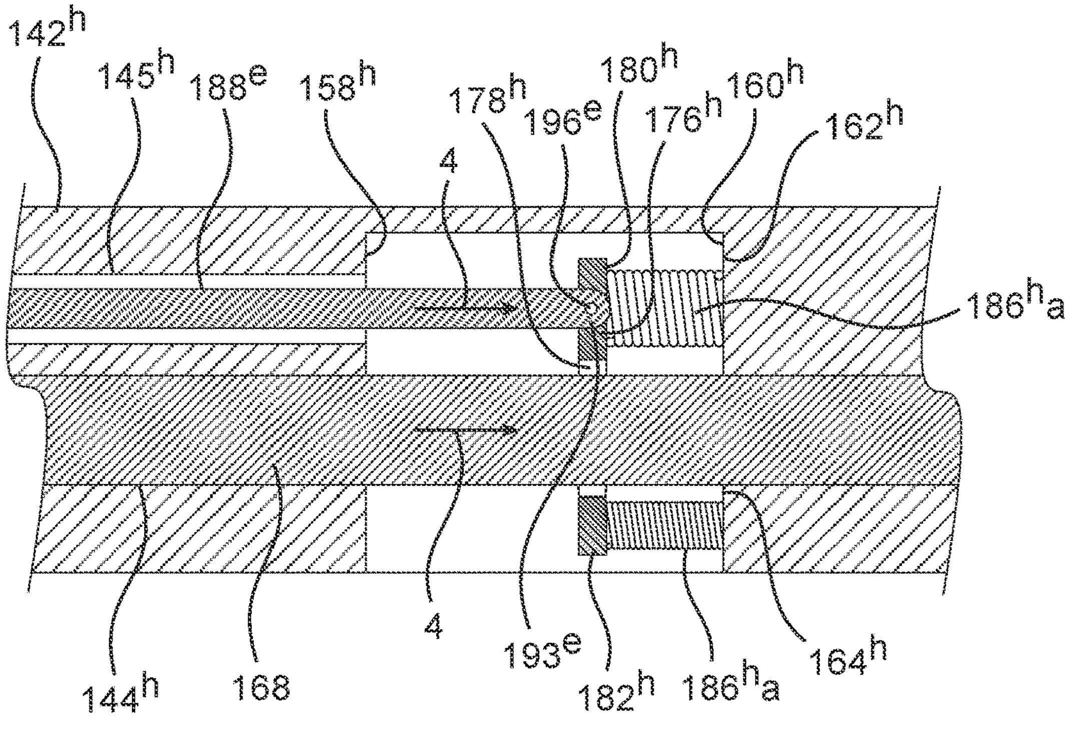
FIG. 20B shows an enlarged cross-sectional view of the expansion and locking assembly of FIG. 20A, in a released state of the plate.

FIGS. 20A-20B show another embodiment of an expansion and locking assembly (140), comprising release member 188$^e$ extending through a release channel 145$h$ of an outer member 142$^h$, and a plate 176$^h$ coupled to the chamber 152$^h$ via two springs 186$^h$ disposed at opposite sides of the inner member 168, and configured to bias each side of the plate 176$^h$ in an opposite direction, in their free states, so as to bias the plate 176$^h$ to the angled locking orientation in their free state.

The outer member 142$^h$ can be similar to any other type of outer member (142) that includes a release channel 145$^h$ for a release member 188$^h$, except that the distal chamber wall 158$^h$ does not need to have an inclined or angled portion. As shown in the illustrated embodiment, both the distal wall first side 162$^h$ and the distal wall second side 164$^h$ may be provided as flat walls, oriented substantially perpendicularly with respect to the longitudinal axis of the inner member 168.

The plate 176$^h$ comprises a primary aperture 178$^h$ through which the inner member extends, and may further engage the release member 188$^h$ at one of its sides, such as the plate first side 180$^h$ in the illustrated example. As shown, the release member distal end portion 192$^e$ may be coupled to the plate 176$^h$ (e.g., to the plate first side 180$^h$) via a release member distal hinge 196$^e$, enabling the plate 176$^h$ to pivot about the hinge 196$^e$ with respect to the release member 188$^h$. It is to be understood the other coupling means between the release member 188$^h$ and the plate 176$^h$ may be applicable, such as via retention features 194$^a$, 194$^b$, 194$^c$ or 194$^d$ as described hereinabove with respect to FIGS. 16A-19B, and that a direct connection between a release member end portion (192) and a plate (176) via a hinge, such as the release member distal hinge 196 illustrated in FIG. 20A-20B, may be used with other embodiments, such as those described hereinabove for release members 188$^b$ or 188$^d$ (i.e., without the utilization of an intermediary retention feature such as retention feature 194$^b$ or 194$^d$).

The outer member 142$^h$ may comprise a first spring 186$^h$$a$, configured to bias the plate first side 180$^h$ in a proximal direction 2, toward the proximal chamber wall 158$^h$, and a second spring 186$^h$$b$, configured to bias the plate second side 182$^h$ in a distal direction 4, toward the distal chamber wall 160$^h$. The first spring 186$^h$$a$ can be a compression spring, disposed within the first zone (154) between the plate first side 180$^h$ and the distal wall first side 162$^h$.

One end of the first spring 186$^h$*a* can be attached to the plate first side 180$^h$, and the other to the distal wall first side 162$^h$. The second spring 186$^h$*b* can be an extension spring, disposed within the first zone (156) between the plate second side 182$^h$ and the distal wall second side 164$^h$. One end of the second spring 186$^h$*b* can be attached to the plate second side 182$^h$, and the other to the distal wall second side 164$^h$.

In some implementations, the first spring 186$^h$*a* is configured to exert a proximally oriented biasing force which is greater in magnitude than the distally oriented biasing force exerted by the second spring 186$^h$*b* on the plate 176$^h$. In some implementations, the spring constant of the first spring 186$^h$*a* is higher than the spring constant of the second spring 186$^h$*b*.

FIG. 20A shows both the first spring 186$^h$*a* and the second spring 186$^h$*b* in a free state thereof, without any external force applied to either one of the springs. In this free state, the plate first side 180$^h$ is biased in a first direction (e.g., the proximal direction 2) by the first spring 186$^h$*a*, while the plate second side 182$^h$ is biased in a second direction (e.g., in a distal direction 4) by the second spring 186$^h$*b*, resulting in the plate 176$^h$ being biased to the angled locking orientation, so as to prevent unintentional axial movement of the inner member 168 in the second direction (e.g., the distal direction 4), thereby locking it in position and preventing spontaneous re-compression of the valve (!00).

It is to be understood that the force exerted by the first spring 186$^h$*a* and the second spring 186$^h$*b* on the plate 176$^h$ are configured to be high enough to bias the plate 176$^h$ to the angled locking orientation in a free state, yet allow the plate 176$^h$ to assume a non-locking orientation when the inner member 168 is pulled in the first direction (e.g., the proximal direction). For example, the spring constants and/or spring dimensions, for both first and second springs 186$^h$*a*, 186$^h$*b*, can be chosen to enable the inner member 168 to be pulled in a proximal direction 2, when expansion of the valve (100) is desired.

FIG. 20B shows a release member 188$^e$ actuated to release the plate 176$^h$ from the angled locking orientation, so as to allow movement of the inner member 168 in a distal direction 4 to re-compress the valve (100). The release member 188$^e$ may be releasably attached to a release assembly 50, for example, in the same manner illustrated and described hereinabove in conjunction with FIGS. 16A-18D. In the state shown in FIG. 20B, the release member 188$^e$ is pushed in the second direction (e.g., the distal direction 4), for example—via the release arm 52 attached to its proximal end portion (190), thereby pushing the plate 176$^h$, and more specifically, the plate second side 182$^h$, therewith, against the first spring 186$^h$*a*. This serves to compress the first spring 186$^h$*a*, allowing the plate 176$^h$ to assume a non-locking orientation, which in turn allows axial translation of the inner member 168 in the second direction (e.g., the distal direction 4) relative to the outer member 142$^h$.

In some embodiments, to facilitate valve re-compression in the state shown in FIG. 20B, an actuation member (42) may be pushed in a distally oriented direction 4, pushing the inner member 168 therewith, thereby causing radial re-compression of the frame 106. In alternative embodiments, valve re-compression is not facilitated by directly applying a pushing force on the actuation members (42), but rather by utilization of a re-compression mechanism of the type disclosed, for example, in International Application Publication No. WO 2020/081893, and U.S. application No. 62/928,320, which basically includes a loop circumscribing the valve (100), wherein loop tensioning or contraction, for example operable via handle (30), facilitates valve contraction there-along, during which the inner member 168 may passively translate in the distal direction 4 as shown in FIG. 20B.

While FIGS. 20A-20B show a release member 188$^h$ attached to the plate 176$^h$, for example via a hinged connection, in other implementation a release member 188 may not be attached to the plate 176, but may be rather spaced away from the plate 176, or may contact the plate 176 but without applying any force thereto, in a free state such as the state shown in FIG. 20A, and may be pushed distally against the plate 176, such that its distal end (193) may press against the plate 176 and push it in the same manner shown in FIG. 20B.

While the first spring 186$^h$*a* is illustrated in FIGS. 20A-20B as a compression spring, disposed between the plate 176$^h$ and the distal chamber wall 160$^h$, in alternative implementations, the first spring 186*a* may be implemented as an extension spring disposed between the plate 176$^h$ and the proximal chamber wall 158$^h$, configured to bias the plate first side 180$^h$ in the same proxi mal direction 2 as shown in FIG. 20A. Similarly, while the second spring 186$^h$*b* is illustrated in FIGS. 20A-20B as an extension spring, disposed between the plate 176$^h$ and the distal chamber wall 160$^h$, in alternative implementations, the second spring 186*b* may be implemented as a compression spring disposed between the plate 176$^h$ and the proximal chamber wall 158$^h$, configured to bias the plate second side 182$^h$ in the same distal direction 4 as shown in FIG. 20A.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A prosthetic valve, comprising:

a frame movable between a radially compressed and a radially expanded configuration;

at least one expansion and locking mechanism, comprising:

- an outer member, coupled to the frame at a first location;
- an inner member, coupled to the frame at a second location spaced apart from the first location, the inner member extending at least partially into the outer member; and
- at least one plate comprising a primary aperture, disposed around the inner member, the at least one plate configured to transition between an angled locking orientation and a non-locking orientation;

wherein movement of the inner member in a first direction, relative to the outer member, causes the frame to foreshorten axially and expand radially in a non-locking orientation of the at least one plate;

wherein in the absence of a force applied to the plate in the first direction, movement of the inner member in a second direction, relative to the outer member, causes the at least one plate to assume the angled locking orientation; and wherein the at least one plate is configured to inhibit advancement of the inner member in the second direction relative to the outer member, when oriented in the angled locking orientation.

Example 2. The prosthetic valve of any example herein, particularly example 1, wherein the outer member further comprises a chamber comprising a proximal chamber wall and a distal chamber wall, and wherein the at least one plate is disposed within the chamber.

Example 3. The prosthetic valve of any example herein, particularly example 2, wherein the outer member further comprises a lateral opening exposing at least a portion of the chamber.

Example 4. The prosthetic valve of any example herein, particularly any one of examples 1 to 3, wherein the at least one plate has a disc-like circular or elliptic shape.

Example 5. The prosthetic valve of any example herein, particularly any one of examples 1 to 3, wherein the at least one plate has a rectangular shape.

Example 6. The prosthetic valve of any example herein, particularly any one of examples 1 to 5, wherein the at least one plate comprises a rigid material.

Example 7. The prosthetic valve of any example herein, particularly any one of examples 1 to 6, wherein the at least one plate comprises a plurality of plates.

Example 8. The prosthetic valve of any example herein, particularly example 2, wherein the distal chamber wall comprises at least one angled portion.

Example 9. The prosthetic valve of any example herein, particularly example 8, wherein the angle formed between the angled portion and the inner member is more acute than the angle formed between the plate and the inner member in the angled locking orientation.

Example 10. The prosthetic valve of any example herein, particularly any one of examples 2 to 9, wherein the diameter of the primary aperture is closely matched with the outer diameter of the inner member extending therethrough, such that axial movement of the inner member frictionally engages with the primary aperture.

Example 11. The prosthetic valve of any example herein, particularly example 10, wherein the diameter of the primary aperture is no more than 5 percent larger than the diameter of the inner member at the portion extending therethrough.

Example 12. The prosthetic valve of any example herein, particularly example 2, wherein at least a portion of the proximal chamber wall is substantially orthogonal to a longitudinal axis of the inner member.

Example 13. The prosthetic valve of any example herein, particularly any one of examples 2 to 12, wherein the outer member comprises a primary channel, configured to accommodate at least a portion of the inner member therein.

Example 14. The prosthetic valve of any example herein, particularly example 2, wherein the outer member further comprises a spring disposed within the chamber, configured to urge the at least one plate in the second direction.

Example 15. The prosthetic valve of any example herein, particularly example 14, wherein the spring is a helical spring coiled around the inner member.

Example 16. The prosthetic valve of any example herein, particularly example 14, wherein the spring is a helical spring disposed adjacent the inner member.

Example 17. The prosthetic valve of any example herein, particularly example 14, wherein the spring is a leaf spring.

Example 18. The prosthetic valve of any example herein, particularly example 2, wherein the plate is coupled to the proximal chamber wall via a plate hinge, and wherein the plate is configured to pivot about the plate hinge between the angled locking orientation and the non-locking orientation.

Example 19. The prosthetic valve of any example herein, particularly example 2, wherein the distal chamber wall comprises a proximally oriented protrusion.

Example 20. The prosthetic valve of any example herein, particularly any one of examples 2 to 13, wherein the at least one expansion and locking mechanism further comprises a release member, extending at least partially into the outer member, the release member coupled to the at least one plate, and configured to transition the at least one plate to the non-locking orientation, and/or retain the at least one plate in the non-locking orientation, when the release member is pulled in the second direction relative to the outer member.

Example 21. The prosthetic valve of any example herein, particularly example 20, wherein the outer member further comprises a release channel, configured to accommodate the release member therein.

Example 22. The prosthetic valve of any example herein, particularly any one of examples 20 to 21, wherein the plate further comprises a release aperture, wherein a distal end portion of the release member extends through the release aperture, and wherein a distal end of the release member comprises a retention feature distal to the release aperture.

Example 23. The prosthetic valve of any example herein, particularly example 22, wherein the distal chamber wall comprises a niche dimensioned to accommodate the retention feature.

Example 24. The prosthetic valve of any example herein, particularly any one of examples 20 to 21, wherein a distal end of the release member is pivotably coupled to the at least one plate via a release member distal hinge.

Example 25. The prosthetic valve of any example herein, particularly any one of examples 19 to 20, wherein the outer member further comprises a first spring and a second spring, disposed within the chamber at opposite sides of the inner member, wherein the first spring is configured to bias one side of the at least one plate in a first direction, and the second spring is configured to bias an opposite second side of the at least one plate in a second direction, thereby biasing the plate to the angled locking orientation in a free state of the first and second springs.

Example 26. The prosthetic valve of any example herein, particularly example 25, wherein the first spring is a compression spring, disposed between the at least one plate and the distal chamber wall, and wherein the second spring is an extension spring disposed between the at least one plate and the distal chamber wall.

Example 27. The prosthetic valve of any example herein, particularly any one of examples 1 to 26, wherein the outer member further comprises an outer member fastener extending radially outward, and wherein the outer member is coupled to the frame at the first location via the outer member fastener.

Example 28. The prosthetic valve of any example herein, particularly any one of examples 1 to 27, wherein the inner member further comprises an inner member fastener extending radially outward, and wherein the inner member is coupled to the frame at the second location via the inner member fastener.

Example 29. The prosthetic valve of any example herein, particularly any one of examples 1 to 28, wherein the frame comprises intersecting struts.

Example 30. A prosthetic valve, comprising:

a frame movable between a radially compressed and a radially expanded configuration;

at least one expansion and locking mechanism, comprising:

an outer member, coupled to the frame at a first location;

at least one expansion and locking mechanism, comprising:

an inner member, coupled to the frame at a second location spaced apart from the first location, the inner member extending at least partially into the outer member;

at least one plate comprising a primary aperture, disposed around the inner member, the at least one plate configured to transition between an angled locking orientation and a non-locking orientation; and at least one spring disposed between the outer member and the at least one plate;

wherein movement of the inner member in a first direction, relative to the outer member, causes the frame to foreshorten axially and expand radially in a non-locking orientation of the at least one plate;

wherein in the absence of a force applied to the plate in the first direction, the at least one spring is configured to bias the at least one plate to the angled locking orientation; and wherein the at least one plate is configured to inhibit advancement of the inner member in the second direction relative to the outer member, when oriented in the angled locking orientation.

Example 31. The prosthetic valve of any example herein, particularly example 30, wherein the at least one plate has a disc-like circular or elliptic shape.

Example 32. The prosthetic valve of any example herein, particularly any one of examples 30 to 31, wherein the at least one plate has a rectangular shape.

Example 33. The prosthetic valve of any example herein, particularly any one of examples 30 to 32, wherein the at least one plate comprises a rigid material.

Example 34. The prosthetic valve of any example herein, particularly any one of examples 30 to 33, wherein the at least one plate comprises a plurality of plates.

Example 35. The prosthetic valve of any example herein, particularly any one of examples 30 to 34, wherein the diameter of the primary aperture is no more than 5 percent larger than the diameter of the inner member at the portion extending therethrough.

Example 36. The prosthetic valve of any example herein, particularly any one of examples 30 to 35, wherein the outer member comprises a primary channel, configured to accommodate at least a portion of the inner member therein.

Example 37. The prosthetic valve of any example herein, particularly any one of examples 30 to 36, wherein the outer member further comprises a chamber comprising a proximal chamber wall and a distal chamber wall, and wherein the at least one plate and the at least one spring are disposed within the chamber.

Example 38. The prosthetic valve of any example herein, particularly example 37, wherein the distal chamber wall comprises a proximally oriented protrusion.

Example 39. The prosthetic valve of any example herein, particularly example 37, wherein the distal chamber wall comprises at least one angled portion.

Example 40. The prosthetic valve of any example herein, particularly example 39, wherein the angle formed between the angled portion and the inner member is more acute than the angle formed between the plate and the inner member in the angled locking orientation.

Example 41. The prosthetic valve of any example herein, particularly any one of examples 37 to 40, wherein at least a portion of the proximal chamber wall is substantially orthogonal to a longitudinal axis of the inner member.

Example 42. The prosthetic valve of any example herein, particularly any one of examples 37 to 40, wherein the at least one spring comprises a helical spring coiled around the inner member.

Example 43. The prosthetic valve of any example herein, particularly example 42, wherein the coiled spring is a compression spring disposed between the proximal chamber wall and the at least one plate.

Example 44. The prosthetic valve of any example herein, particularly any one of examples 37 to 41, wherein the at least one spring comprises at least one helical spring disposed adjacent the inner member.

Example 45. The prosthetic valve of any example herein, particularly example 44, wherein the at least one helical spring is a compression spring disposed between the proximal chamber wall and the at least one plate.

Example 46. The prosthetic valve of any example herein, particularly example 44, wherein the at least one helical spring is an extension spring disposed between the distal chamber wall and the at least one plate.

Example 47. The prosthetic valve of any example herein, particularly any one of examples 37 to 44, wherein the at least one spring is a leaf spring.

Example 48. The prosthetic valve of any example herein, particularly any one of examples 37 to 40, wherein the at least one expansion and locking mechanism further comprises a release member, extending at least partially into the outer member, the release member coupled to the at least one plate, and configured to transition the at least one plate to the non-locking orientation, and/or retain the at least one plate in the non-locking orientation, when the release member is pulled in the second direction relative to the outer member.

Example 49. The prosthetic valve of any example herein, particularly example 48, wherein the outer member further comprises a release channel, configured to accommodate the release member therein.

Example 50. The prosthetic valve of any example herein, particularly any one of examples 48 to 49, wherein the at least one plate further comprises a release aperture, wherein a distal end portion of the release member extends through the release aperture, and wherein a distal end of the release member comprises a retention feature distal to the release aperture.

Example 51. The prosthetic valve of any example herein, particularly example 50, wherein the distal chamber wall comprises a niche dimensioned to accommodate the retention feature.

Example 52. The prosthetic valve of any example herein, particularly any one of examples 48 to 49, wherein a distal end of the release member is pivotably coupled to the at least one plate via a release member distal hinge.

Example 53. The prosthetic valve of any example herein, particularly example 48, wherein the at least one spring comprises a first spring and a second spring, both of which are disposed within the chamber at opposite sides of the inner member, wherein the first spring is configured to bias one side of the at least one plate in a first direction, and the second spring is configured to bias an opposite second side of the at least one plate in a second direction, thereby biasing the plate to the angled locking orientation in a free state of the first and second springs.

Example 54. The prosthetic valve of any example herein, particularly example 53, wherein the first spring is a compression spring, disposed between the at least one plate and the distal chamber wall, and wherein the second spring is an extension spring disposed between the at least one plate and the distal chamber wall.

Example 55. A delivery assembly, comprising:

a prosthetic valve comprising:

a frame movable between a radially compressed and a radially expanded configuration;

at least one expansion and locking mechanism comprising:

an outer member having an outer member first end and an outer member second end, wherein the outer member is coupled to the frame at a first location;

an inner member having an inner member first end and an inner member second end, wherein the inner member is coupled to the frame at a second location spaced apart from the first location, and wherein the inner member extends at least partially into the outer member; and at least one plate comprising a primary aperture, disposed around the inner member, the at least one plate configured to transition between an angled locking orientation and a non-locking orientation;

a delivery apparatus comprising:

a handle;

a delivery shaft extending distally from the handle; and at least one actuation assembly extending from the handle through the delivery shaft, and detachably coupled to the at least one expansion and locking assembly;

wherein the frame is movable from the radially compressed configuration to the radially expanded configuration upon actuating the at least one expansion and locking assembly by the at least one actuation assembly;

wherein movement of the inner member in a first direction, relative to the outer member, causes the frame to foreshorten axially and expand radially in a non-locking orientation of the at least one plate;

wherein in the absence of a force applied to the plate in the first direction, movement of the inner member in a second direction, relative to the outer member, causes the at least one plate to assume the angled locking orientation; and wherein the at least one plate is configured to inhibit advancement of the inner member in the second direction relative to the outer member, when oriented in the angled locking orientation.

Example 56. The delivery assembly of any example herein, particularly example 55, wherein the at least one actuation assembly comprises an actuation member and an actuation support sleeve disposed around the actuation member, and wherein the actuation member and the actuation support sleeve are movable longitudinally relative to each other in a telescoping manner.

Example 57. The delivery assembly of any example herein, particularly example 56, wherein the at least one actuation member is chosen from: a wire, a cable, a rod, or a tube.

Example 58. The delivery assembly of any example herein, particularly any one of examples 56 to 57, wherein the actuation support sleeve is a tube or a sheath having sufficient rigidity, such that the actuation support sleeve can apply an axial force against the outer member without bending or buckling.

Example 59. The delivery assembly of any example herein, particularly any one of examples 56 to 58, wherein the at least one actuation member is threadedly engaged with the corresponding inner member.

Example 60. The delivery assembly of any example herein, particularly any one of examples 56 to 59, wherein the handle comprises a plurality of knobs.

Example 61. The delivery assembly of any example herein, particularly example 60, wherein at least one of the plurality of knobs is configured to axially move each actuation member relative to the respective actuation support sleeve.

Example 62. The delivery assembly of any example herein, particularly example 60, wherein at least one of the plurality of knobs is configured to disengage each actuation assembly from the respective expansion and locking assembly.

Example 63. The delivery assembly of any example herein, particularly any one of examples 55 to 62, wherein the outer member further comprises a chamber comprising a proximal chamber wall and a distal chamber wall, and wherein the at least one plate is disposed within the chamber.

Example 64. The delivery assembly of any example herein, particularly any one of examples 55 to 63, wherein the at least one plate has a disc-like circular or elliptic shape.

Example 65. The delivery assembly of any example herein, particularly any one of examples 55 to 63, wherein the at least one plate has a rectangular shape.

Example 66. The delivery assembly of any example herein, particularly any one of examples 55 to 65, wherein the at least one plate comprises a rigid material.

Example 67. The delivery assembly of any example herein, particularly any one of examples 55 to 66, wherein the at least one plate comprises a plurality of plates.

Example 68. The delivery assembly of any example herein, particularly example 63, wherein the distal chamber wall comprises at least one angled portion.

Example 69. The delivery assembly of any example herein, particularly example 68, wherein the angle formed between the angled portion and the inner member is more acute than the angle formed between the plate and the inner member in the angled locking orientation.

Example 70. The delivery assembly of any example herein, particularly any one of examples 55 to 69, wherein the diameter of the primary aperture is closely matched with the outer diameter of the inner member extending therethrough, such that axial movement of the inner member frictionally engages with the primary aperture.

Example 71. The delivery assembly of any example herein, particularly example 70, wherein the diameter of the primary aperture is no more than 5 percent larger than the diameter of the inner member at the portion extending therethrough.

Example 72. The delivery assembly of any example herein, particularly example 63, wherein at least a portion of the proximal chamber wall is substantially orthogonal to a longitudinal axis of the inner member.

Example 73. The delivery assembly of any example herein, particularly any one of examples 56 to 62, wherein the outer member comprises a primary channel, configured to accommodate at least a portion of the inner member and at least a portion of the actuation member therein.

Example 74. The delivery assembly of any example herein, particularly example 63, wherein the outer member further comprises a spring disposed within the chamber, configured to urge the at least one plate in the second direction.

Example 75. The delivery assembly of any example herein, particularly example 74, wherein the spring is a helical spring coiled around the inner member.

Example 76. The delivery assembly of any example herein, particularly example 74, wherein the spring is a helical spring disposed adjacent the inner member.

Example 77. The delivery assembly of any example herein, particularly example 74, wherein the spring is a leaf spring.

Example 78. The delivery assembly of any example herein, particularly example 63, wherein the plate is coupled to the proximal chamber wall via a plate hinge, and wherein the plate is configured to pivot about the plate hinge between the angled locking orientation and the non-locking orientation.

Example 79. The delivery assembly of any example herein, particularly example 63, wherein the distal chamber wall comprises a proximally oriented protrusion.

Example 80. A delivery assembly, comprising:

a prosthetic valve comprising:

a frame movable between a radially compressed and a radially expanded configuration;

at least one expansion and locking mechanism comprising:

an outer member having an outer member first end and an outer member second end, wherein the outer member is coupled to the frame at a first location;

an inner member having an inner member first end and an inner member second end, wherein the inner member is coupled to the frame at a second location spaced apart from the first location, and wherein the inner member extends at least partially into the outer member;

at least one plate comprising a primary aperture, disposed around the inner member, the at least one plate configured to transition between an angled locking orientation and a non-locking orientation; and a release member extending at least partially into the outer member, the release member coupled to the at least one plate;

a delivery apparatus comprising:

a handle;

a delivery shaft extending distally from the handle;

at least one actuation assembly extending from the handle through the delivery shaft, and detachably coupled to the at least one expansion and locking assembly; and at least one release assembly extending from the handle through the delivery shaft, and detachably coupled to the at least one release member;

wherein the frame is movable from the radially compressed configuration to the radially expanded configuration upon actuating the at least one expansion and locking assembly by the at least one actuation assembly;

wherein movement of the inner member in a first direction, relative to the outer member, causes the frame to foreshorten axially and expand radially in a non-locking orientation of the at least one plate;

wherein in the absence of a force applied to the plate in the first direction, movement of the inner member in a second direction, relative to the outer member, causes the at least one plate to assume an angled locking orientation;

wherein the at least one plate is configured to inhibit advancement of the inner member in the second direction relative to the outer member, when oriented in the angled locking orientation; and wherein the release member is configured to transition the at least one plate to the non-locking orientation, and/or retain the at least one plate in the non-locking orientation, when the release member is pulled by the release assembly in the first direction relative to the outer member.

Example 81. The delivery assembly of any example herein, particularly example 80, wherein the at least one actuation assembly comprises an actuation member and an actuation support sleeve disposed around the actuation member, and wherein the actuation member and the support sleeve are movable longitudinally relative to each other in a telescoping manner.

Example 82. The delivery assembly of any example herein, particularly example 81, wherein the at least one actuation member is chosen from: a wire, a cable, a rod, or a tube.

Example 83. The delivery assembly of any example herein, particularly any one of examples 81 to 82, wherein the support sleeve is a tube or a sheath having sufficient rigidity, such that the support sleeve can apply an axial force against the frame without bending or buckling.

Example 84. The delivery assembly of any example herein, particularly any one of examples 81 to 83, wherein the at least one actuation member is threadedly engaged with the corresponding inner member.

Example 85. The delivery assembly of any example herein, particularly any one of examples 81 to 84, wherein the at least one release assembly comprises a release arm and a release support sleeve disposed around the release arm, and wherein the release arm and the release support sleeve are movable longitudinally relative to each other in a telescoping manner.

Example 86. The delivery assembly of any example herein, particularly example 85, wherein the at least one release arm is chosen from: a wire, a cable, a rod, or a tube.

Example 87. The delivery assembly of any example herein, particularly any one of examples 85 to 86, wherein the release support sleeve is a tube or a sheath having sufficient rigidity, such that the release support sleeve can apply an axial force against the outer member without bending or buckling.

Example 88. The delivery assembly of any example herein, particularly any one of examples 85 to 87, wherein the at least one release arm is threadedly engaged with the corresponding release member.

Example 89. The delivery assembly of any example herein, particularly any one of examples 81 to 88, wherein the handle comprises a plurality of knobs.

Example 90. The delivery assembly of any example herein, particularly example 89, wherein at least one of the plurality of knobs is configured to axially move each actuation member relative to the respective actuation support sleeve.

Example 91. The delivery assembly of any example herein, particularly example 89, wherein at least one of the plurality of knobs is configured to axially move each release arm relative to the respective release support sleeve.

Example 92. The delivery assembly of any example herein, particularly example 89, wherein at least one of the plurality of knobs is configured to disengage each actuation assembly from the respective expansion and locking assembly.

Example 93. The delivery assembly of any example herein, particularly example 89, wherein at least one of the plurality of knobs is configured to disengage each release assembly from the respective expansion and locking assembly.

Example 94. The delivery assembly of any example herein, particularly any one of examples 80 to 93, wherein the outer member further comprises a chamber comprising a proximal chamber wall and a distal chamber wall, and wherein the at least one plate is disposed within the chamber.

Example 95. The delivery assembly of any example herein, particularly any one of examples 80 to 94, wherein the at least one plate has a disc-like circular or elliptic shape.

Example 96. The delivery assembly of any example herein, particularly any one of examples 80 to 95, wherein the at least one plate has a rectangular shape.

Example 97. The delivery assembly of any example herein, particularly any one of examples 80 to 96, wherein the at least one plate comprises a rigid material.

Example 98. The delivery assembly of any example herein, particularly any one of examples 80 to 97, wherein the at least one plate comprises a plurality of plates.

Example 99. The delivery assembly of any example herein, particularly example 94, wherein the distal chamber wall comprises at least one angled portion.

Example 100. The delivery assembly of any example herein, particularly example 99, wherein the angle formed between the angled portion and the inner member is more acute than the angle formed between the plate and the inner member in the angled locking orientation.

Example 101. The delivery assembly of any example herein, particularly any one of examples 80 to 100, wherein the diameter of the primary aperture is closely matched with the outer diameter of the inner member extending therethrough, such that axial movement of the inner member frictionally engages with the primary aperture.

Example 102. The delivery assembly of any example herein, particularly example 101, wherein the diameter of the primary aperture is no more than 5 percent larger than the diameter of the inner member at the portion extending therethrough.

Example 103. The delivery assembly of any example herein, particularly example 94, wherein at least a portion of the proximal chamber wall is substantially orthogonal to a longitudinal axis of the inner member.

Example 104. The delivery assembly of any example herein, particularly any one of examples 81 to 84, wherein the outer member comprises a primary channel, configured to accommodate at least a portion of the inner member and at least a portion of the actuation member therein.

Example 105. The delivery assembly of any example herein, particularly any one of examples 85 to 88, wherein the outer member comprises a release channel, configured to accommodate at least a portion of the release member and at least a portion of the release arm therein.

Example 106. The delivery assembly of any example herein, particularly example 94, wherein the outer member further comprises a spring disposed within the chamber, configured to urge the at least one plate in the second direction.

Example 107. The delivery assembly of any example herein, particularly example 106, wherein the spring is a helical spring coiled around the inner member.

Example 108. The delivery assembly of any example herein, particularly example 106, wherein the spring is a helical spring disposed adjacent the inner member.

Example 109. The delivery assembly of any example herein, particularly example 106, wherein the spring is a leaf spring.

Example 110. The delivery assembly of any example herein, particularly example 94, wherein the plate is coupled to the proximal chamber wall via a plate hinge, and wherein the plate is configured to pivot about the plate hinge between the angled locking orientation and the non-locking orientation.

Example 111. The delivery assembly of any example herein, particularly example 94, wherein the distal chamber wall comprises a proximally oriented protrusion.

Example 112. The delivery assembly of any example herein, particularly any one of examples 80 to 111, wherein the at least one plate further comprises a release aperture, wherein a distal end portion of the release member extends through the release aperture, and wherein a distal end of the release member comprises a retention feature distal to the release aperture.

Example 113. The delivery assembly of any example herein, particularly example 94, wherein the at least one plate further comprises a release aperture, wherein a distal end portion of the release member extends through the release aperture, wherein a distal end of the release member comprises a retention feature distal to the release aperture, and wherein the distal chamber wall comprises a niche dimensioned to accommodate the retention feature.

Example 114. The delivery assembly of any example herein, particularly any one of examples 80 to 111, wherein a distal end of the release member is pivotably coupled to the at least one plate via a release member distal hinge.

Example 115. The delivery assembly of any example herein, particularly any one of examples 80 to 105, wherein the outer member further comprises a first spring and a second spring, disposed within the chamber at opposite sides of the inner member, wherein the first spring is configured to bias one side of the at least one plate in a first direction, and the second spring is configured to bias an opposite second side of the at least one plate in a second direction, thereby biasing the plate to the angled locking orientation in a free state of the first and second springs.

Example 116. The delivery assembly of any example herein, particularly example 94, wherein the outer member further comprises a first spring and a second spring, disposed within the chamber at opposite sides of the inner member, wherein the first spring is configured to bias one side of the at least one plate in a first direction, and the second spring is configured to bias an opposite second side of the at least one plate in a second direction, thereby biasing the plate to the angled locking orientation in a free state of the first and second springs, wherein the first spring is a compression spring, disposed between the at least one plate and the distal chamber wall, and wherein the second spring is an extension spring disposed between the at least one plate and the distal chamber wall.

Example 117. A method of implanting a prosthetic valve, the method comprising:

positioning a prosthetic valve at a target site in a patient's body using a delivery apparatus, wherein the prosthetic valve comprises at least one expansion and locking assembly, the expansion and locking assembly comprising an outer member, an inner member partially disposed within, and movable axially relative to, the outer member, and at least one plate dispose within the outer member and around the inner member, and wherein the delivery apparatus comprises at least one actuation assembly, detachably coupled to the at least one expansion and locking assembly;

radially expanding the prosthetic valve from a radially compressed configuration to a radially expanded configuration, by applying, via the at least one actuation assembly, a pull force on the inner member, configured to axially move the inner member in a first direction relative to the outer member; and locking the expansion and locking assembly by releasing the pull force exerted on the inner member by the actuation assembly, thereby allowing the at least one plate to assume an angled locking orientation.

Example 118. The method of any example herein, particularly example 117, wherein the radially expanded configuration comprises partially expanded configurations and/or a fully expanded configuration, and wherein the step of radially expanding the prosthetic valve is executed again after the locking step, so as to reorient the at least one plate from the angled locking orientation to a non-locking orientation, allowing further expansion of the prosthetic valve from a partially expanded configuration to another partially expanded configuration or to a fully expanded configuration.

Example 119. The method of any example herein, particularly any one of examples 117 to 118, wherein the at least one actuation assembly comprises an actuation member detachably coupled to the inner member, and an actuation support sleeve disposed around the actuation member, and wherein the step of radially expanding the prosthetic valve comprises exerting a pull force to move the actuation member in a first direction relative to the actuation support sleeve, while keeping the actuation support sleeve stationary or moved in an opposite second direction, so as to apply a counter force against the outer member.

Example 120. The method of any example herein, particularly example 119, further comprising a step of detaching the at least one actuation member from the at least one inner member, and retrieving the delivery apparatus from the patient's body.

Example 121. The method of any example herein, particularly example 120, wherein the at least one actuation member is threadedly engaged with the at least one inner member, and wherein detaching the at least one actuation member comprises rotating the at least one actuation member around a longitudinal axis thereof.

Example 122. A method of implanting a prosthetic valve, the method comprising:

- positioning a prosthetic valve at a target site in a patient's body using a delivery apparatus, wherein the prosthetic valve comprises at least one expansion and locking assembly, the expansion and locking assembly comprising an outer member, an inner member partially disposed within, and movable axially relative to, the outer member, at least one plate dispose within the outer member and around the inner member, and a release member disposed within the outer member and axially movable relative thereto, the release member coupled to the at least one plate, and wherein the expansion and locking assembly comprises at least one actuation assembly detachably coupled to the at least one expansion and locking assembly, and at least one release assembly detachably coupled to the release member;
- radially expanding the prosthetic valve from a radially compressed configuration to a radially expanded configuration, by applying, via the at least one actuation assembly, a pull force on the inner member, configured to axially move the inner member in a first direction relative to the outer member;
- locking the expansion and locking assembly by releasing the pull force exerted on the inner member by the actuation assembly, thereby allowing the at least one plate to assume an angled locking orientation;
- unlocking the expansion and locking assembly by applying, via the at least one release assembly, a pull force on the release member, configured to transition the at least one plate from the angled locking orientation to a non-locking orientation; and
- re-compressing the prosthetic valve such that the at least one inner member is moved in a second direction relative to the at least one outer member.

Example 123. The method of any example herein, particularly example 122, wherein any of the steps of radially expanding the prosthetic valve, locking, unlocking, and re-compressing the prosthetic valve, are repeated for any desired number of times and in any order, so as to reach a final desired expansion diameter of the prosthetic valve.

Example 124. The method of any example herein, particularly any one of examples 122 to 123, further comprising a step of re-positioning the prosthetic valve using the delivery apparatus, after the step of re-compressing the prosthetic valve.

Example 125. The method of any example herein, particularly any one of examples 122 to 124, wherein the at least one actuation assembly comprises an actuation member detachably coupled to the inner member, and an actuation support sleeve disposed around the actuation member, wherein the at least one release assembly comprises a release arm detachably coupled to the release member, and a release support sleeve disposed around the release arm, wherein the step of radially expanding the prosthetic valve comprises exerting a pull force to move the actuation member in a first direction relative to the actuation support sleeve, while keeping the actuation support sleeve stationary or moved in an opposite second direction, so as to apply a counter force against the outer member, and wherein the step of unlocking the prosthetic valve comprises exerting a pull force to move the release arm in a first direction relative to the release support sleeve, while keeping the release support sleeve stationary or moved in an opposite second direction, so as to apply a counter force against the outer member.

Example 126. The method of any example herein, particularly example 125, further comprising steps of detaching the at least one actuation member from the at least one inner member, detaching the at least one release arm from the release member, and retrieving the delivery apparatus from the patient's body.

Example 127. The method of any example herein, particularly example 126, wherein the at least one actuation member is threadedly engaged with the at least one inner member, wherein the at least one release arm is threadedly engaged with the at least one release member, wherein detaching the at least one actuation member comprises rotating the at least one actuation member around a longitudinal axis thereof, and wherein detaching the at least one release arm comprises rotating the at least one release arm around a longitudinal axis thereof.

Example 128. A method for assembling an expansion and locking mechanism, comprising the steps of:

providing an outer member comprising a chamber and a lateral opening exposing at least a portion of the chamber;

inserting at least one plate, comprising a primary aperture, into the chamber through the lateral opening;

orienting the at least one plate in a substantially orthogonal orientation, relative to a longitudinal axis of the outer member; and inserting the inner member into the outer member, through the primary aperture of the at least one plate.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

In view of the many possible embodiments to which the principles of the disclosure may be applied, it should be recognized that the illustrated embodiments are only preferred examples and should not be taken as limiting the scope. Rather, the scope is defined by the following claims. We therefore claim all that comes within the scope and spirit of these claims.

The invention claimed is:

1. A prosthetic valve, comprising:

a frame movable between a radially compressed and a radially expanded configuration;

at least one expansion and locking mechanism, comprising:

an outer member, coupled to the frame at a first location;

an inner member, coupled to the frame at a second location spaced apart from the first location, the inner member extending at least partially into the outer member; and at least one plate comprising a primary aperture, disposed around the inner member, the at least one plate configured to transition between an angled locking orientation and a non-locking orientation;

wherein movement of the inner member in a first direction, relative to the outer member, causes the frame to foreshorten axially and expand radially in a non-locking orientation of the at least one plate;

wherein in the absence of a force applied to the plate in the first direction, movement of the inner member in a second direction, relative to the outer member, causes the at least one plate to assume the angled locking orientation; and wherein the at least one plate is configured to inhibit advancement of the inner member in the second direction relative to the outer member, when oriented in the angled locking orientation.

2. The prosthetic valve of claim 1, wherein the outer member further comprises a chamber comprising a proximal chamber wall and a distal chamber wall, and wherein the at least one plate is disposed within the chamber.

3. The prosthetic valve of claim 1, wherein the at least one plate comprises a plurality of plates.

4. The prosthetic valve of claim 2, wherein the distal chamber wall comprises at least one angled portion.

5. The prosthetic valve of claim 4, wherein the angle formed between the angled portion and the inner member is more acute than the angle formed between the plate and the inner member in the angled locking orientation.

6. The prosthetic valve of claim 2, wherein the diameter of the primary aperture is closely matched with the outer diameter of the inner member extending therethrough, such that axial movement of the inner member frictionally engages with the primary aperture.

7. The prosthetic valve of claim 2, wherein the outer member further comprises a spring disposed within the chamber, configured to urge the at least one plate in the second direction.

8. The prosthetic valve of claim 2, wherein the at least one expansion and locking mechanism further comprises a release member, extending at least partially into the outer member, the release member coupled to the at least one plate, and configured to transition the at least one plate to the non-locking orientation, and/or retain the at least one plate in the non-locking orientation, when the release member is pulled in the second direction relative to the outer member.

9. A delivery assembly, comprising:

a prosthetic valve comprising:

a frame movable between a radially compressed and a radially expanded configuration;

at least one expansion and locking mechanism comprising:

an outer member having an outer member first end and an outer member second end, wherein the outer member is coupled to the frame at a first location;

an inner member having an inner member first end and an inner member second end, wherein the inner member is coupled to the frame at a second location spaced apart from the first location, and wherein the inner member extends at least partially into the outer member; and at least one plate comprising a primary aperture, disposed around the inner member, the at least one plate configured to transition between an angled locking orientation and a non-locking orientation;

a delivery apparatus comprising:

a handle;

a delivery shaft extending distally from the handle; and at least one actuation assembly extending from the handle through the delivery shaft, and detachably coupled to the at least one expansion and locking assembly;

wherein the frame is movable from the radially compressed configuration to the radially expanded configuration upon actuating the at least one expansion and locking assembly by the at least one actuation assembly;

wherein movement of the inner member in a first direction, relative to the outer member, causes the frame to foreshorten axially and expand radially in a non-locking orientation of the at least one plate;

wherein in the absence of a force applied to the plate in the first direction, movement of the inner member in a second direction, relative to the outer member, causes the at least one plate to assume the angled locking orientation; and wherein the at least one plate is configured to inhibit advancement of the inner member in the second direction relative to the outer member, when oriented in the angled locking orientation.

10. The delivery assembly of claim 9, wherein the at least one actuation assembly comprises an actuation member and an actuation support sleeve disposed around the actuation member, and wherein the actuation member and the actuation support sleeve are movable longitudinally relative to each other in a telescoping manner.

11. The delivery assembly of claim 9, wherein the outer member further comprises a chamber comprising a proximal chamber wall and a distal chamber wall, and wherein the at least one plate is disposed within the chamber.

12. The delivery assembly of claim 9, wherein the at least one plate comprises a plurality of plates.

13. The delivery assembly of claim 11, wherein the distal chamber wall comprises at least one angled portion.

14. The delivery assembly of claim 13, wherein the angle formed between the angled portion and the inner member is more acute than the angle formed between the plate and the inner member in the angled locking orientation.

15. The delivery assembly of claim 9, wherein the diameter of the primary aperture is closely matched with the outer diameter of the inner member extending therethrough, such that axial movement of the inner member frictionally engages with the primary aperture.

16. A delivery assembly, comprising:

a prosthetic valve comprising:

a frame movable between a radially compressed and a radially expanded configuration;

at least one expansion and locking mechanism comprising:
an outer member having an outer member first end and an outer member second end, wherein the outer member is coupled to the frame at a first location;
an inner member having an inner member first end and an inner member second end, wherein the inner member is coupled to the frame at a second location spaced apart from the first location, and wherein the inner member extends at least partially into the outer member;
at least one plate comprising a primary aperture, disposed around the inner member, the at least one plate configured to transition between an angled locking orientation and a non-locking orientation; and
a release member extending at least partially into the outer member, the release member coupled to the at least one plate;
a delivery apparatus comprising:
a handle;
a delivery shaft extending distally from the handle;
at least one actuation assembly extending from the handle through the delivery shaft, and detachably coupled to the at least one expansion and locking assembly; and
at least one release assembly extending from the handle through the delivery shaft, and detachably coupled to the at least one release member;
wherein the frame is movable from the radially compressed configuration to the radially expanded configuration upon actuating the at least one expansion and locking assembly by the at least one actuation assembly;
wherein movement of the inner member in a first direction, relative to the outer member, causes the frame to foreshorten axially and expand radially in a non-locking orientation of the at least one plate;
wherein in the absence of a force applied to the plate in the first direction, movement of the inner member in a second direction, relative to the outer member, causes the at least one plate to assume an angled locking orientation;
wherein the at least one plate is configured to inhibit advancement of the inner member in the second direction relative to the outer member, when oriented in the angled locking orientation; and
wherein the release member is configured to transition the at least one plate to the non-locking orientation, and/or retain the at least one plate in the non-locking orientation, when the release member is pulled by the release assembly in the first direction relative to the outer member.

17. The delivery assembly of claim 16, wherein the at least one actuation assembly comprises an actuation member and an actuation support sleeve disposed around the actuation member, and wherein the actuation member and the support sleeve are movable longitudinally relative to each other in a telescoping manner.

* * * * *